US011883378B2

(12) United States Patent
Roth et al.

(10) Patent No.: US 11,883,378 B2
(45) Date of Patent: Jan. 30, 2024

(54) HYDROGEL FORMULATIONS AND METHODS AND DEVICES FOR FOCAL ADMINISTRATION OF THE SAME

(71) Applicant: Pykus Therapeutics, Inc., Cambridge, MA (US)

(72) Inventors: Laurence A. Roth, Windham, NH (US); Charles Sidoti, Cambridge, MA (US); James Anthony Stefater, III, Boston, MA (US); Tomasz Pawel Stryjewski, Somerville, MA (US)

(73) Assignee: PYKUS THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 17/992,275

(22) Filed: Nov. 22, 2022

(65) Prior Publication Data

US 2023/0157988 A1 May 25, 2023

Related U.S. Application Data

(60) Provisional application No. 63/283,020, filed on Nov. 24, 2021.

(51) Int. Cl.
| | |
|---|---|
| A61K 31/25 | (2006.01) |
| A61K 31/795 | (2006.01) |
| A61K 47/54 | (2017.01) |
| A61K 9/06 | (2006.01) |
| A61K 9/00 | (2006.01) |

(52) U.S. Cl.
CPC ............ *A61K 31/25* (2013.01); *A61K 9/0048* (2013.01); *A61K 9/06* (2013.01); *A61K 31/795* (2013.01); *A61K 47/548* (2017.08)

(58) Field of Classification Search
CPC ..................................................... A61K 31/25
See application file for complete search history.

(56) References Cited

U.S. PATENT DOCUMENTS

| | | | |
|---|---|---|---|
| 5,654,349 A | 8/1997 | Feingold et al. | |
| 6,149,931 A | 11/2000 | Schwartz | |
| 6,828,401 B2 | 12/2004 | Nho | |
| 7,115,417 B1 | 10/2006 | Chancellor et al. | |
| 7,659,260 B2 | 2/2010 | Kadrmas | |
| 7,833,206 B1 | 11/2010 | Lumpkin et al. | |
| 9,072,809 B2 | 7/2015 | Askari | |
| 9,125,807 B2 | 9/2015 | Sawhney et al. | |
| 9,623,144 B2 | 4/2017 | Askari | |
| 9,873,769 B2 | 1/2018 | Braithwaite et al. | |
| 10,874,767 B2 * | 12/2020 | Stefater, III | A61L 27/58 |
| 10,973,954 B2 * | 4/2021 | Stefater, III | A61L 27/58 |
| 10,973,955 B2 * | 4/2021 | Stefater, III | A61P 27/02 |
| 11,077,232 B2 * | 8/2021 | Stefater, III | A61L 27/58 |
| 11,547,779 B2 * | 1/2023 | Stefater, III | A61L 27/26 |
| 2006/0141049 A1 | 6/2006 | Lyons et al. | |
| 2006/0292190 A1 | 12/2006 | Matier et al. | |
| 2008/0107694 A1 | 5/2008 | Trogden | |
| 2009/0017097 A1 | 1/2009 | Sawhney et al. | |
| 2011/0082221 A1 | 4/2011 | Haug | |
| 2012/0082730 A1 | 4/2012 | Banerjee et al. | |
| 2012/0100103 A1 | 4/2012 | Park | |
| 2012/0189708 A1 | 7/2012 | Van Epps et al. | |
| 2014/0248231 A1 | 9/2014 | Askari et al. | |
| 2015/0273108 A1 | 10/2015 | Askari et al. | |
| 2016/0009872 A1 | 1/2016 | Braithwait | |
| 2017/0175791 A1 | 6/2017 | Baur et al. | |
| 2019/0175791 A1 | 6/2019 | Stefater, III et al. | |
| 2019/0216982 A1 | 7/2019 | Roth et al. | |
| 2019/0224375 A1 | 7/2019 | Stefater, III et al. | |
| 2020/0338233 A1 | 10/2020 | Roth et al. | |

(Continued)

FOREIGN PATENT DOCUMENTS

| | | |
|---|---|---|
| CN | 101338036 B | 11/2010 |
| CN | 101934089 A | 1/2011 |

(Continued)

OTHER PUBLICATIONS

Xiao et al. Biomacromolecules, 2009, 10(7): 1939-1946 (i.e., abstract).*
"Bioworld: molecular tools and laboratory essentials: PBS 5X with Saponin", https://www.bio-world.com/elisa-buffer/pbs-5x-with-saponin-p-40120364, 2020 (2 pages).
International Search Report and Written Opinion issued by the U.S. Patent and Trademark Office as International Searching Authority in International Application No. PCT/US22/80314 dated Mar. 22, 2023 (17 pages).
"Two Deans' Challenges garner 90 proposals", Harvard Gazette, https://news.harvard.edu/gazette/story/2016/03/two-deans-challenges-garner-90-proposals/, Mar. 9, 2016, accessed Jan. 8, 2019 (6 pages).

(Continued)

*Primary Examiner* — Rei Tsang Shiao
(74) *Attorney, Agent, or Firm* — Wilmer Cutler Pickering Hale and Dorr LLP

(57) ABSTRACT

Provided are formulations, methods, and devices for providing a hydrogel. The formulations and resulting hydrogels may be used for treating various disorders, including ocular disorders. In certain embodiments, the hydrogel is formed from formulations comprising (a) a nucleo-functional polymer that is a biocompatible polyalkylene polymer substituted by (i) a plurality of —OH groups, (ii) a plurality of thio-functional groups —$R^1$—SH wherein $R^1$ is an ester-containing linker, and (iii) optionally one or more —OC(O)—($C_1$-$C_6$ alkyl) groups, such as a thiolated poly(vinyl alcohol) polymer; (b) an electro-functional polymer that is a biocompatible polymer containing at least one thiol-reactive group, such as a poly(ethylene glycol) polymer containing alpha-beta unsaturated ester groups; and (c) one or more pharmaceutically active agents. In certain embodiments, the hydrogel is formed at a targeted sited using methods and/or devices for focal administration of the formulations and/or hydrogels described herein.

15 Claims, 11 Drawing Sheets

(56) References Cited

U.S. PATENT DOCUMENTS

| | | |
|---|---|---|
| 2021/0007762 A1 | 1/2021 | Chang et al. |
| 2021/0077663 A1 | 3/2021 | Stefater, III et al. |
| 2021/0077664 A1 | 3/2021 | Stefater, III et al. |
| 2021/0187168 A1 | 6/2021 | Stefater, III et al. |

FOREIGN PATENT DOCUMENTS

| | | | |
|---|---|---|---|
| CN | 102911493 | | 2/2013 |
| CN | 111741776 | | 10/2020 |
| WO | WO-2005072768 A1 | | 8/2005 |
| WO | WO-2006078458 | | 7/2006 |
| WO | WO-2008008859 | | 1/2008 |
| WO | WO-2008066787 | | 6/2008 |
| WO | WO-2009006780 | | 1/2009 |
| WO | WO-2013086015 | | 6/2013 |
| WO | WO-2013170195 A1 | | 11/2013 |
| WO | WO-2016049791 A1 | | 4/2016 |
| WO | WO-2016197005 A1 | | 12/2016 |
| WO | WO 2018/013819 | * | 1/2018 |
| WO | WO-2018/013819 A1 | | 1/2018 |
| WO | WO-2019/140184 A1 | | 7/2019 |
| WO | WO-2019/140212 A1 | | 7/2019 |
| WO | WO-2022150497 A1 | | 7/2022 |

OTHER PUBLICATIONS

Alarake, N.Z. et al., "Mechanical properties and biocompatibility of in situ enzymatically cross-linked gelatin hydrogels", Int. J Artif Organs, 40(4):159-168. published online Mar. 18, 2017 (10 pages).

Almany, L. et al., "Biosynthetic hydrogel scaffolds made from fibrinogen and polyethylene glycol for 3D cell cultures", Biomaterials, 26:2467-2477, May 2005, available online Aug. 20, 2004 (11 pages).

Artzi, N. et al., "Characterization of Star Adhesive Sealants Based on PEG/Dextran Hydrogels", Macromol Biosci, 9:754-765, 2009 (12 pages).

Bai, X. et al., "Dual crosslinked chondroitin sulfate injectable hydrogel formed via continuous Diels-Alder (DA) click chemistry for bone repair", Carbohydrate Polymers, 166:123-130, available online Feb. 20, 2017 (8 pages).

Baino, F., "The Use of Polymers in the Treatment of Retinal Detachment: Current Trends and Future Perspectives", Polymers, 2:286-322, Sep. 9, 2010 (37 pages).

Bang, S. et al., "Injectable pullulan hydrogel for the prevention of postoperative tissue adhesion", International Journal of Biological Macromolecules, 87:155-162, Jun. 2016, published online Feb. 12, 2016 (8 pages).

Barth, H. et al., "A cross-linked hyaluronic acid hydrogel (Healaflow®) as a novel vitreous substitute", Graefes Arch Clin Exp Ophthalmol 254(4):697-703, published online Jan. 8, 2016 (7 pages).

Barth, H. et al., "A new model for in vitro testing of vitreous substitute candidates", Graefes Arch Clin Exp Ophthalmol 252:1581-1592, published online Jul. 25, 2014 (12 pages).

Bernkop-Schnürch, A., "Thiomers: A new generation of mucoadhesive polymers", Advanced Drug Delivery Reviews, 57:1569-1582, available online Sep. 19, 2005 (14 pages).

Boyd, S. et al., Management of Complications in Ophthalmic Surgery, Boyd and Wu, Eds., Jaypee-Highlights Medical Publishers, Inc., Panama, pp. 85-87, 2009 (5 pages).

Chang, J. et al., "An in situ-forming zwitterionic hydrogel as vitreous substitute", J. Mater. Chem. B, 3:1097-1105 (2015), first published Dec. 4, 2014 (9 pages).

Chang, S. et al., "Giant Retinal Tears—Surgical Techniques and Results Using Perfluorocarbon Liquids", Arch Ophthalmology, 107:761-766, May 1989, accessed Jan. 8, 2019 (6 pages).

Chen, X. et al., "Chitosan-based thermosensitive hydrogel as a promising ocular drug delivery system: Preparation, characterization, and in vivo evaluation", Journal of Biomaterials Applications, 27(4):391-402, 2011 (12 pages).

Chien, H-W. et al., "An in situ poly(carboxybetaine) hydrogel for tissue engineering applications", Biomater Sci, 5:322-330, published online Jan. 4, 2017 (9 pages).

Chien, Y. et al., "Corneal repair by human corneal keratocyte-reprogrammed iPSCs and amphiphatic carboxymethyl-hexanoyl chitosan hydrogel", Biomaterials, 33:8003-8016, available online Jul. 31, 2012 (14 pages).

Chirila, T.V. et al., "Synthetic Polymers as Materials for Artificial Vitreous Body: Review and Recent Advances", Journal of Biomaterials Applications, 9(2):121-37, Oct. 1994 (17 pages).

Chirila, T.V. et al., "The Use of Hydrophilic Polymers as Artificial Vitreous", Prog. Polym. Sci., 23:475-508, 1998 (34 pages).

Cho, E. et al., "Formulation and characterization of poloxamine-based hydrogels as tissue sealants", Acta Biomaterialia, 8(6):2223-2232, Mar. 8, 2012 (10 pages).

Cho, S-H. et al., "An injectable collagen/poly(γ-glutamic acid) hydrogel as a scaffold of stem cells and a-lipoic acid for enhanced protection against renal dysfunction", Biomater Sci., 5:285-294, 2017, published online Dec. 15, 2016 (10 pages).

Coseal® Surgical Sealant, Instructions for Use, Baxter Healthcare Corporation, Hayward, California, http://www.coseal.com/us/pdf/COSEAL_IFU.pdf, dated Mar. 2009 (2 pages).

Crafoord, S. et al., "Experimental vitreous tamponade using polyalkylimide hydrogel", Graefes Arch Clin Exp Ophthalmol, 249(8):1167-1174, published online Mar. 31, 2011 (8 pages).

D'Souza, A. et al., "Polyethylene glycol (PEG): a versatile polymer for pharmaceutical applications", Expert Opinion on Drug Delivery, 13(9):1257-1275, Published online May 17, 2016 (20 pages).

Daniele, S. et al., "Glyceryl Methacrylate Hydrogel as a Vitreous Implant: An Experimental Study", Arch of Ophthal, 80(1):120-127, Jul. 1968, accessed Jan. 8, 2019 (7 pages).

Davidorf, F.H. et al., "Ocular Toxicity of Vitreal Pluronic Polyol F-127", Retina, 10(4):297-300, 1990 (4 pages).

De Jong, et al., "ADCON®-L Hydrogel as a Vitreous Substitute: Preliminary Results", Bulletin de la Société Belge d'Ophtalmologie, 278:71-75, 2000 (5 pages).

Deerenberg, E.B. et al., "Polyvinyl Alcohol Hydrogel Decreases Formation of Adhesions in a Rat Model of Peritonitis", Surgical Infections, 13(5):321-325, 2012 (5 pages).

Donati, S. et al., "Vitreous Substitutes: The Present and the Future", BioMed Research International, vol. 2014, Article 351804, pp. 1-12, May 4, 2014 (13 pages).

Dong, D. et al., "In Situ "Clickable" Zwitterionic Starch-Based Hydrogel for 3D Cell Encapsulation", ACS Applied Materials & Interfaces, 8:4442-4455, Jan. 28, 2016 (14 pages).

Dong, Y. et al., "Performance of an in situ formed bioactive hydrogel dressing from a PEG-based hyperbranched multifunctional copolymer", Acta Biomaterialia, 10:2076-2085, May 2014, available online Dec. 31, 2013 (10 pages).

Du, H. et al., "Injectable in situ Physically and Chemically Crosslinkable Gellan Hydrogel", Author Manuscript published in final edited form as Macromol Biosci., 12(7):952-961, Jul. 2012 (24 pages).

Duker, J., "Chapter 6.30: Macular Hole", Ophthalmology, Third Edition, Yanoff, et al., Eds., Mosby Elsevier, pp. 682-685, 2009 (6 pages).

DuraSeal Product Information, Integra LifeSciences Corporation, Plainsboro, New Jersey, www.integralife.com, dated Jun. 2014 (2 pages).

Emoto, S. et al., "Intraperitoneal administration of cisplatin via an in situ cross-linkable hyaluronic acid-based hydrogel for peritoneal dissemination of gastric cancer", Surg Today, 44(5):919-926, 2014, published online Jul. 26, 2013 (8 pages).

Engelbert, M. et al., "Chapter 6.6, Vitrectomy", Ophthalmology, Third Edition, Yanoff, et al., Eds., Mosby Elsevier, pp. 530-533, 2009 (6 pages).

European Extended Search Report issued in European Application No. 19738225.2, dated Sep. 23, 2021 (10 pages).

European Supplemental Search Report issued in EP17828468.3 dated Feb. 18, 2020 (8 pages).

Examination Report No. 1 for standard patent application, dated Mar. 18, 2021, for Australian Patent Application No. 2017295715 (5 pages).

(56) References Cited

OTHER PUBLICATIONS

Falabella, C.A. et al., "Novel Macromolecular Crosslinking Hydrogel to Reduce Intra-Abdominal Adhesions", Journal of Surgical Research, 159(2):772-778, Apr. 2010 (7 pages).

Fathalla, Z. M.A. et al., "Poloxamer-based thermoresponsive ketorolac tromethamine in situ gel preparations: Design, characterisation, toxicity and transcorneal permeation studies", Eur J. Pharm Biopharm, 114:119-134, published online Jan. 24, 2017 (16 pages).

FDA, Medical Devices Databases, Product Classification, Device: Fluid, Intraocular, Mar. 31, 2016, Advisory Committee/Panel Meetings—CDRH, last updated Jan. 7, 2019 (2 pages).

Fernández-Ferreiro, A. et al., "In vitro and in vivo ocular safety and eye surface permanence determination by direct and Magnetic Resonance Imaging of ion-sensitive hydrogels based on gellan gum and kappa-carrageenan", Eur J. Pharm Biopharm, 94:342-351, published online Jun. 14, 2015 (10 pages).

First Office Action, dated Feb. 10, 2021, for Chinese Patent Application No. 201780043404.0 (12 pages)—English Summary.

Foster, W.J. et al., "Internal Osmotic Pressure as a Mechanism of Retinal Attachment in a Vitreous Substitute", Journal of Bioactive and Compatible Polymers, 21:221-235, May 1, 2006 (15 pages).

Gao, Y. et al., "PLGA-PEG-PLGA hydrogel for ocular drug delivery of dexamethasone acetate", Drug Dev Ind Pharm, 36(10):1131-1138, 2010 (9 pages).

Ghobril, C. et al., "A Dendritic Thioester Hydrogel Based on Thiol-Thioester Exchange as a Dissolvable Sealant System for Wound Closure", Angew. Chem. Int. Ed, 52:14070-14074, 2013 (5 pages).

Ghosh, S. et al., "Strong poly(ethylene oxide) based gel adhesives via oxime cross-linking", Acta Biomaterialia, 29:206-214, Jan. 1, 2016, published online Oct. 22, 2015 (9 pages).

Gupta, H. et al., "Physiologically active hydrogel (in situ gel) of sparfloxacin and its evaluation for ocular retention using gamma scintigraphy", J Pharm Bioallied Sci., 7(3):195-200, Jul.-Sep. 2015 (8 pages).

Hahn, et al., "Influence of hydrogel mechanical properties and mesh size on vocal fold fibroblast extracellular matrix production and phenotype," Author Manuscript published in final edited form as *Acta Biomaterialia* 4(5):1161-1171, Sep. 2008 (19 pages).

Hassan, W. et al., "Encapsulation and 3D culture of human adipose-derived stem cells in an in-situ crosslinked hybrid hydrogel composed of PEG-based hyperbranched copolymer and hyaluronic acid", Stem Cell Research & Therapy, 4(2):32, Mar. 21, 2013 (11 pages).

Healaflow, Product Information, Aptissen S.A., Geneva, Switzerland, http://www.aptissen.com/wp-content/uploads/2016/02/healaflow_brochure.pdf, accessed Jan. 29, 2019 (12 pages).

Hermann, C.D. et al., "Rapidly polymerizing injectable click hydrogel therapy to delay bone growth in a murine re-synostosis model", Biomaterials, 35(36):9698-9708, Dec. 2014, available online Aug. 28, 2014 (11 pages).

Hogen-Esch, T.E. et al., "Development of Injectable Poly(glyceryl Methacrylate) Hydrogels for Vitreous Prosthesis" Journal of Biomedical Materials Research, 10(6):975-976, 1976 (2 pages).

Hombrebueno, et al., "Intravitreal Injection of Normal Saline Induces Retinal Degeneration in the C57BL/6J Mouse," Transl Vis Sci Technol. 3(2):Article 3, Mar. 2014 (10 pages).

Hong, J.H. et al., "Injectable Polypeptide Thermogel as a Tissue Engineering System for Hepatogenic Differentiation of Tonsil-Derived Mesenchymal Stem Cells", Applied Materials & Interfaces, 9:11568-11576, Mar. 14, 2017 (9 pages).

Hong, Y. et al., "Biodegradation in vitro and retention in the rabbit eye of crosslinked poly(1-vinyl-2-pyrrolidinone) hydrogel as a vitreous substitute", Journal of Biomedical Materials Research, 39(4):650-659, 1998 (10 pages).

Hoshi, S. et al., "In Vivo and In Vitro Feasibility Studies of Intraocular Use of Polyethylene Glycol- Based Synthetic Sealant to Close Retinal Breaks in Porcine and Rabbit Eyes", Invest Ophthalmol Vis Sci, 56(8):4705-4711, Jul. 2015 (7 pages).

Hoshi, S. et al., "Polyethylene Glycol-Based Synthetic Hydrogel Sealant for Closing Vitrectomy Wounds: An In Vivo and Histological Study", Transl Vis Sci Technol, 5(3):Article 7, May 2016 (8 pages).

Huang, W. et al., "Preparation, pharmacokinetics and pharmacodynamics of ophthalmic thermosensitive in situ hydrogel of betaxolol hydrochloride", Biomed Pharmaco, 83:107-113, Oct. 2016 (7 pages).

Huynh, C.T. et al., "Synthesis, Characteristics and Potential Application of Poly(ß-Amino Ester Urethane)-Based Multiblock Co-Polymers as an Injectable, Biodegradable and pH/Temperature-Sensitive Hydrogel System", Journal of Biomaterials Science 23:1091-1106, 2012 (17 pages).

International Search Report and Written Opinion as issued by U.S. Patent and Trademark Office as International Search Authority, in International Application PCT/US19/13223, dated Apr. 12, 2019 (9 pages).

International Search Report and Written Opinion issued by the Australian Patent Office in International Application No. PCT/US17/41947 dated Aug. 21, 2017 (8 pages).

International Search Report and Written Opinion issued by the U.S. Patent and Trademark Office as International Searching Authority, issued in PCT/US19/13185, dated Apr. 15, 2019 (9 pages).

International Search Report and Written Opinion issued by U.S. Patent and Trademark Office as International Searching Authority in International Application No. PCT/US22/11469, dated Mar. 22, 2022 (11 pages).

Ishiyama, N. et al., "The prevention of peritendinous adhesions by a phospholipid polymer hydrogel formed in situ by spontaneous intermolecular interactions", Biomaterials, 31(14):4009-4016, May 2010, published online Feb. 10, 2010 (8 pages).

Kang, W. et al., "Photocrosslinked methacrylated carboxymethyl chitin hydrogels with tunable degradation and mechanical behavior", Carbohydrate Polymers, 160:18-25, 2017, published online Dec. 19, 2016 (8 pages).

Katagiri, Y. et al., "Application of Thermo-setting Gel as Artificial Vitreous", Japanese Journal of Ophthalmology, 49(6):491-96, 2005 (6 pages).

Kim, et al., "Dual Enzyme-Triggered In Situ Crosslinkable Gelatin Hydrogels for Artificial Cellular Microenvironments", Macromol Biosci, 16(11):1570-1576, 2016 (7 pages).

Kim, K.D. et al., "Polyethylene Glycol Hydrogel Spinal Sealant (DuraSeal Spinal Sealant) as an Adjunct to Sutured Dural Repair in the Spine: Results of a Prospective, Multicenter, Randomized Controlled Study", Spine, 36(23):1906-1912, Nov. 1, 2011 (7 pages).

Kleinberg, T.T. et al., "Vitreous Substitutes: A Comprehensive Review", Survey of Ophthalmology, 56(4):300-323, Jul.-Aug. 2011 (24 pages).

Kumar, D. et al., "Three-dimensional hypoxic culture of human mesenchymal stem cells encapsulated in a photocurable, biodegradable polymer hydrogel: A potential injectable cellular product for nucleus pulposus regeneration", Acta Biomater, 10:3463-3474, published online May 2, 2014 (12 pages).

Kwon, J.W. et al., "Biocompatibility of poloxamer hydrogel as an injectable intraocular lens: A pilot study", J Cataract Refract Surg, 31:607-613, 2005 (7 pages).

Lee, H. et al., "Fast in situ enzymatic gelation of PPO-PEO block copolymer for injectable intraocular lens in vivo", J Biomater Appl, 28(8):1247-1263, 2014 (17 pages).

Li, C. et al., "Enhancement in bioavailability of ketorolac tromethamine via intranasal in situ hydrogel based on poloxamer 407 and carrageenan", Int J Pharm, 474(1-2):123-133, published online Aug. 17, 2014 (11 pages).

Li, et al., "Engineering In Situ Cross-Linkable and Neurocompatible Hydrogels", J Neurotrauma, 31:1431-1438, Aug. 15, 2014 (8 pages).

Li, L. et al., "Biodegradable and injectable in situ cross-linking chitosan-hyaluronic acid based hydrogels for postoperative adhesion prevention", Biomaterials, 35(12):3903-3917, available online Feb. 4, 2014 (15 pages).

(56) References Cited

OTHER PUBLICATIONS

Li, L. et al., "Injectable and Biodegradable pH-Responsive Hydrogels for Localized and Sustained Treatment of Human Fibrosarcoma", Applied Materials & Interfaces, 7:8033-8040, Apr. 2, 2015 (8 pages).

Li, Q. et al., "Biodegradable and photocrosslinkable polyphosphoester hydrogel", Biomaterials, 27:1027-1034, Mar. 2006, available online Aug. 24, 2005 (8 pages).

Li, S. et al., "Injectable PAMAM/ODex double-crosslinked hydrogels with high mechanical strength", Biomed. Mater, 12:015012, 2017, published online Dec. 9, 2016 (12 pages).

Li, X. et al., "A covalently crosslinked polysaccharide hydrogel for potential applications in drug delivery and tissue engineering", J Mater Sci: Mater Med, 23:2857-2865, published online Oct. 4, 2012 (9 pages).

Li, X. et al., "In situ gel-forming AP-57 peptide delivery system for cutaneous wound healing", Int J Pharm, 495(1):560-571, available online Sep. 9, 2015 (12 pages).

Liang, Y. et al., "An in situ formed biodegradable hydrogel for reconstruction of the corneal endothelium", Colloids Surf B: Biointerfaces, 82(1):1-7, 2011, available online Jul. 30, 2010 (7 pages).

Lin, C-Y. et al., "In situ forming hydrogel composed of hyaluronate and polygalacturonic acid for prevention of peridural fibrosis", J Mater Sci: Mater Med, 26:168, published online Mar. 20, 2015 (12 pages).

Linh, N.T.B. et al., "Enzymatic in situ formed hydrogel from gelatin-tyramine and chitosan-4-hydroxylphenyl acetamide for the co-delivery of human adipose-derived stem cells and platelet-derived growth factor towards vascularization", Biomed. Mater., 12:015026, Feb. 24, 2017 (12 pages).

Liu, H. et al., "Thermosensitive injectable in-situ forming carboxymethyl chitin hydrogel for three-dimensional cell culture", Acta Biomaterialia, 35:228-237, published online Feb. 18, 2016 (10 pages).

Luo, Z. et al., "Thermosensitive Peg-Pcl-Peg (Pece) hydrogel as an in situ gelling system for ocular drug delivery of diclofenac sodium", Drug Delivery, 23(1):63-68, 2016, published online Apr. 24, 2014 (7 pages).

Lutolf, et al., "Synthetic matrix metalloproteinase-sensitive hydrogels for the conduction of tissue regeneration: Engineering cell-invasion characteristics," PNAS, 100(9):5413-5418, Apr. 29, 2003 (6 pages).

Lv, Z., et al., "Thermosensitive in situ hydrogel based on the hybrid of hyaluronic acid and modified PCL/PEG triblock copolymer", Carbohydrate Polymers, 108:26-33, published online Mar. 21, 2014 (8 pages).

Mah, F.S. "Effect on Gel Formation Time of Adding Topical Ophthalmic Medications to ReSure Sealant, an In Situ Hydrogel", J Ocul Pharmacol Ther, 32(6):396-399, 2016 (5 pages).

Marmor, "Retinal detachment from hyperosmotic intravitreal injection", Investigative Ophthalmology & Visual Science, 18(12):1237-1244, Dec. 1979 (8 pages).

Marticorena, et al., "Sterile Endophthalmitis after Intravitreal Injections," Mediators Inflamm., vol. 2012, Article ID 928123, 2012 (6 pages).

Maruoka, S. et al., "Biocompatibility of Polyvinylalcohol Gel as a Vitreous Substitute", Current Eye Research, 31(7-8):599-606, 2006 (9 pages).

Masket, S. et al., "Hydrogel sealant versus sutures to prevent fluid egress after cataract surgery", J Cataract Refract Surg, 40:2057-2066, 2014 (10 pages).

Mazza, E. et al., "Mechanical biocompatibility of highly deformable biomedical materials", J Mech Behav Biomed Mater, 48:100-124, available online Apr. 1, 2015 (25 pages).

McKay, C.A. et al., "An Injectable, Calcium Responsive Composite Hydrogel for the Treatment of Acute Spinal Cord Injury", ACS Applied Materials & Interfaces, 6(3):1424-1438, Jan. 3, 2014 (15 pages).

Migliavacca, et al., "Experimental short-term tolerance to perfluorodecalin in the rabbit eye: a histopathological study", Current Eye Research, 17(8):828-835, Jul. 2, 1998 (9 pages).

Miki, D. et al., "A Photopolymerized Sealant for Corneal Lacerations", Cornea, 21(4):393-399, May 2002 (7 pages).

Miles, D.E. et al., "Peptide: glycosaminoglycan hybrid hydrogels as an injectable intervention for spinal disc degeneration", J Materials Chemistry B, Materials for Biology and Medicine, 4(19):3225-3231, May 11, 2016 (8 pages).

Morelli, A. et al., "Design, preparation and characterization of ulvan based thermosensitive hydrogels", Carbohydrate Polymers, 136:1108-1117, 2016, available online Oct. 13, 2015 (10 pages).

Na, S.Y. et al., "Hyaluronic acid/mildly crosslinked alginate hydrogel as an injectable tissue adhesion barrier", J Mater Sci: Mater Med, 23:2303-2313, published online Jun. 3, 2012 (11 pages).

Naderi-Meshkin, H. et al., "Chitosan-based injectable hydrogel as a promising in situ forming scaffold for cartilage tissue engineering", Cell Biol Int, 38(1):72-84, Jan. 2014, published online Oct. 15, 2013 (14 pages).

Nam, K. et al., "Modeling of swelling and drug release behavior of spontaneously forming hydrogels composed of phospholipid polymers", Int J. Pharm, 275(1-2):259-269, May 2004 (11 pages).

Nam, K. et al., "pH-modulated release of insulin entrapped in a spontaneously formed hydrogel system composed of two water-soluble phospholipid polymers", J Biomater. Sci. Polym Edn., 13(11):1259-1269, 2002 (12 pages).

Nie, W. et al., "Rapidly in situ forming chitosan/e-polylysine hydrogels for adhesive sealants and hemostatic materials", Carbohydrate Polymers, 96:342-348, available online Apr. 15, 2013 (7 pages).

Notice of Grounds for Rejection, dated Jul. 13, 2021, for Japanese Patent Application No. 2019-500823 (6 pages).

Ossipov, D.A. et al., "Poly(vinyl alcohol) Cross-Linkers for in Vivo Injectable Hydrogels", Macromolecules, 41(11):3971-3982, 2008, accessed Jan. 8, 2019 (12 pages).

Parel, J-M. et al., "Chapter 129: Silicone Oils: Physicochemical Properties", Retina: vol. I, Fourth Edition, Ryan, Editor, Mosby Elsevier, pp. 2191-2210, 2006 (22 pages).

Patel, S.P. et al., "Novel Thermosensitive Pentablock Copolymers for Sustained Delivery of Proteins in the Treatment of Posterior Segment Diseases", Author Manuscript published in final edited form as Protein Pept Lett, 21(11):1185-1200, 2014 (34 pages).

Peyman, G.A. et al., "Diagnostic and Surgical Techniques: Perfluorocarbon Liquids in Ophthalmology", Kramer, et al., eds., Survey of Ophthalmology, 39(5):375-395, 1995 (21 pages).

Preliminary Office Action, dated May 11, 2021, for Brazilian Application No. BR112019000504-8 (5 pages).

Quinteros, D.A. et al., "Evaluation of the Performance of an Ophthalmic Thermosensitive Hydrogel Containing Combination of Suramin and Bevacizumab", Current Pharmaceutical Design, 22:1-9, 2016 (9 pages).

Ramakumar, S. et al., "Local Hemostasis during Laparoscopic Partial Nephrectomy Using Biodegradable Hydrogels: Initial Porcine Results", Journal of Endourology, 16(7):489-494, Sep. 2002 (6 pages).

Ren, et al., "Patching Retinal Breaks with Healaflow in 27-Gauge Vitrectomy for the Treatment of Rhegmatogenous Retinal Detachment", Publish Ahead of Print. http://doi.org/10.1097/IAE.0000000000002701, Retina, 40(10):1900-1908, 2020 (9 pages).

ReSure® Sealant Product Information, Instructions for Use, Ocular Therapeutix, Bedford, Massachusetts, https://www.resuresealant.com/wp-content/uploads/2017/05/LCN-80-1004-011-Rev-C-ReSure-Sealant-Instructions-for-Use.pdf, accessed Jan. 29, 2019 (2 pages).

Sakai, S. et al., "Peritoneal adhesion prevention by a biodegradable hyaluronic acid-based hydrogel formed in situ through a cascade enzyme reaction initiated by contact with body fluid on tissue surfaces", Acta Biomaterialia, 24:152-158, available online Jun. 20, 2015 (7 pages).

Sanders, L. et al., "Mechanical Characterization of a Bi-functional Tetronic Hydrogel Adhesive for Soft Tissues", Author Manuscript published in final edited form as J Biomed Mater Res A., 103(3):861-868, Mar. 2015 (19 pages).

Santhanam, S. et al., "Biomimetic hydrogel with tunable mechanical properties for vitreous substitutes", Acta Biomaterialia, 43:327-337, published online Jul. 29, 2016 (11 pages).

(56) References Cited

OTHER PUBLICATIONS

Second Office Action, dated Oct. 26, 2021, for Chinese Patent Application No. 201780043404.0 (20 pages).
Shazly, T.M. et al., "Augmentation of postswelling surgical sealant potential of adhesive hydrogels", Journal of Biomedical Materials Research A, 95A(4):1159-1169, published online Sep. 28, 2010 (11 pages).
Sinapis, et al., "Pharmacokinetics of intravitreal bevacizumab (Avastin®) in rabbits", *Clin Ophthalmol.*, 5:697-704, May 23, 2011 (8 pages).
Steffensen, S.L. et al., "Soft hydrogels interpenetrating silicone—A polymer network for drug-releasing medical devices", J Biomed Mater Res Part B, 104B:402-410, 2016, published online Apr. 17, 2015 (9 pages).
Suchaoin, W. et al., "Mucoadhesive polymers: Synthesis and in vitro characterization of thiolated poly(vinyl alcohol)," International Journal of Pharmaceutics, 503(1):141-149, DOI: 10.1016/j.ijpharm.2016.03.006, published online Mar. 7, 2016 (9 pages).
Supplementary European Search Report and Search Opinion, dated Sep. 23, 2021, for EP Application No. 19738225.2 (10 pages).
Svirkin, Y. et al., "Biodegradable thiol-modified poly(vinyl alcohol) hydrogels", Materials Research Society, MRS 2013, Cambridge Polymer Group, Presentation 7-17, Oct. 1, 2010 (14 pages).
Swindle, K. et al., "Recent advances in polymeric vitreous substitutes", Expert Review of Ophthalmology, 2(2):255-265, 2007 (11 pages).
Swindle-Reilly, K.E. et al., "Chapter 13: Designing hydrogels as vitreous substitutes in ophthalmic surgery", Biomaterials and Regenerative Medicine in Ophthalmology, Traian Chirila, Ed., Woodhead Publishing, Sawston, Cambridge, Great Britain, pp. 339-373, 2010 (36 pages).
Swindle-Reilly, K.E. et al., "Rabbit Study of an In Situ Forming Hydrogel Vitreous Substitute", Investigative Ophthalmology & Visual Science, 50(10):4840-4846, Oct. 2009 (7 pages).
Taich, P. et al., "Sustained-release hydrogels of topotecan for retinoblastoma", Colloids and Surfaces B: Biointerfaces, 146:624-631, published online Jul. 2, 2016 (8 pages).
Takahashi, A. et al., "In Situ Cross-Linkable Hydrogel of Hyaluronan Produced via Copper-Free Click Chemistry", Biomacromolecules, 14:3581-3588, Sep. 4, 2013 (8 pages).
Tan, J. et al., "Improved cell adhesion and proliferation on synthetic phosphonic acid-containing hydrogels", Biomaterials, 26:3663-3671, Jun. 2005 (9 pages).
Tao, Y. et al., "Evaluation of an in situ chemically crosslinked hydrogel as a long-term vitreous substitute material", Acta Biomaterialia, 9:5022-5030, Feb. 2013, available online Sep. 27, 2012 (9 pages).
Teruya, et al., "Patching retinal breaks with Seprafilm® in experimental rhegmatogenous retinal detachment of rabbit eyes", Eye, 23:2256-2259, published online Jan. 23, 2009 (4 pages).
Tortora, M. et al., "Michael-Type Addition Reactions for the In Situ Formation of Poly(vinyl alcohol)-Based Hydrogels", Biomacromolecules, 8(1):209-214, 2007 (6 pages).
Transparency Market Research, "Vitreous Tamponades Market: (By Types: Gases, Silicone Oil and Perfluorocarbons)—Global Industry Analysis, Size, Growth, Trends and Forecast, 2014-2020", 2015 (73 pages).
Vaziri, K. et al., "Tamponade in the surgical management of retinal detachment", Clinical Ophthalmology, 10:471-476, 2016 (6 pages).
Vijayasekaran, S. et al., "Poly(1-Vinyl-2-Pyrrolidinone) Hydrogels as Vitreous Substitutes: Histopathological Evaluation in the Animal Eye", Journal of Biomaterials Science, Polymer Edition, 7(8):685-696, 1996 (13 pages).
Villa-Camacho, J.C. et al., "The efficacy of a lysine-based dendritic hydrogel does not differ from those of commercially available tissue sealants and adhesives: an ex vivo study", BMC Musculoskeletal Disorders, 16:116, May 2015 (6 pages).
Vulpe, R. et al., "Rheological study of in-situ crosslinkable hydrogels based on hyaluronanic acid, collagen and sericin", Materials Science and Engineering C, 69:388-397, published online Jul. 5, 2016 (10 pages).

Wallace, D.G. et al., "A Tissue Sealant Based on Reactive Multifunctional Polyethylene Glycol", J Biomed Mater Res (Appl Biomater), 58(5):545-555, 2001 (11 pages).
Wang, et al., "Acute Intraocular Inflammation Caused by Endotoxin after Intravitreal Injection of Counterfeit Bevacizumab in Shanghai, China," Ophthalmology 120(2):355-361, Feb. 2013 (7 pages).
Wang, J. et al., "In Situ-Forming Polyamidoamine Dendrimer Hydrogels with Tunable Properties Prepared via Aza-Michael Addition Reaction", Applied Materials & Interfaces, 9:10494-10503, Mar. 6, 2017 (10 pages).
Wang, R. et al., "Fast in situ generated e-polylysine-poly (ethylene glycol) hydrogels as tissue adhesives and hemostatic materials using an enzyme-catalyzed method", J Biomater Appl, 29(8):1167-1179, 2015 (13 pages).
Wang, T. et al., "Preparation and properties of a novel thermosensitive hydrogel based on chitosan/hydroxypropyl methylcellulose/glycerol", International Journal of Biological Macromolecules, 93:775-782, published online Sep. 14, 2016 (8 pages).
Wathier, M. et al., "Dendritic Macromers as in Situ Polymerizing Biomaterials for Securing Cataract Incisions", J Am Chem Soc, 126(40):12744-12745, published online Sep. 21, 2004 (9 pages).
Wei, C-Z. et al., "A thermosensitive chitosan-based hydrogel barrier for post-operative adhesions' prevention", Biomaterials, 30:5534-5540, published online Aug. 3, 2009 (7 pages).
Weng, L. et al., "An in situ forming biodegradable hydrogel-based embolic agent for interventional therapies", Acta Biomaterialia, 9:8182-8191, published online Jun. 19, 2013 (10 pages).
Wu, et al., "Novel self-assembled tacrolimus nanoparticles cross-linking thermosensitive hydrogels for local rheumatoid arthritis therapy", Colloids and Surfaces B: Biointerfaces, 149:97-104, published online Oct. 6, 2016 (8 pages).
Xia, Zhengnong et al., DaCihai, General knowledge evidence 1, vol. 37, Materials Science Volume, Shanghai Lexicographical Publishing House, p. 499, Dec. 31, 2015 (5 pages)—with English Translation.
Xu, Y. et al., "Spontaneous Packaging and Hypothermic Storage of Mammalian Cells with a Cell-Membrane-Mimetic Polymer Hydrogel in a Microchip", Applied Materials & Interfaces, 7:23089-23097, Oct. 5, 2015 (9 pages).
Xu, Y. et al., "Synthesis, characterization, biodegradability and biocompatibility of a temperature-sensitive PBLA-PEG-PBLA hydrogel as protein delivery system with low critical gelation concentration", Drug Development and Industrial Pharmacy, 40(9):1264-1275, 2014, published online Jul. 15, 2013 (13 pages).
Yin, H. et al., "Toxicity Evaluation of Biodegradable and Thermosensitive PEG-PCL-PEG Hydrogel as a Potential In Situ Sustained Ophthalmic Drug Delivery System", J Biomed Mater Res B: Appl Biomater, 92B(1):129-137, 2010, published online Oct. 2, 2009 (9 pages).
Yu, J. et al., "In situ covalently cross-linked PEG hydrogel for ocular drug delivery applications", International Journal of Pharmaceutics, 470(1-2):151-157, available online Apr. 23, 2014 (7 pages).
Yu, Y. et al., "Injectable Chemically Crosslinked Hydrogel for the Controlled Release of Bevacizumab in Vitreous: A 6-Month In Vivo Study", http://tvstjournal.org/doi/full/10.1167/tvst.4.2.5, Translational Vision Science & Technology, 4(2):Article 5, Mar. 2015 (11 pages).
Zarembinski, T.I. et al., "Thiolated hyaluronan-based hydrogels crosslinked using oxidized glutathione: An injectable matrix designed for ophthalmic applications", Acta Biomaterialia, 10:94-103, 2014, published online Oct. 1, 2013 (10 pages).
Zawaneh, P.N. et al., "Design of an injectable synthetic and biodegradable surgical biomaterial", PNAS, 107(24):11014-11019, Jun. 15, 2010 (6 pages).
Zhao, X. et al., "Photocrosslinkable Gelatin Hydrogel for Epidermal Tissue Engineering", Advanced Healthcare Materials, 5:108-118, 2016 (11 pages).
Zhou, Y. et al., "Rapid Gelling Chitosan/Polylysine Hydrogel with Enhanced Bulk Cohesive and Interfacial Adhesive Force: Mimick-

(56) References Cited

OTHER PUBLICATIONS ing Features of Epineurial Matrix for Peripheral Nerve Anastomosis", Biomacromolecules, 17(2):622-630, Jan. 18, 2016 (9 pages).

* cited by examiner

HYDROGEL FORMULATIONS AND METHODS AND DEVICES FOR FOCAL ADMINISTRATION OF THE SAME

CROSS REFERENCE TO RELATED APPLICATIONS

This application claims the benefit of priority to U.S. Provisional Patent Application Ser. No. 63/283,020, filed on Nov. 24, 2021, the disclosure of which is incorporated by reference herein in its entirety.

FIELD OF THE INVENTION

The invention is directed to formulations comprising polymers and polymer compositions that form hydrogels, including extended-release hydrogels, comprising a pharmaceutically active agent (e.g., a drug) and methods of using the hydrogels comprising a pharmaceutically active agent for providing targeted release of the pharmaceutically active agent to a site of interest in a subject for a variety of disorders. The invention is also directed to medical devices and methods for focal delivery of the hydrogel-forming polymer formulations and compositions comprising application of a low-viscosity polymer formulation or composition to a targeted site of interest.

BACKGROUND

Delivering a pharmaceutically active agent (e.g., a drug) to the body in an extended-release fashion provides many benefits to the subject, including more specific delivery, less off-site side-effects, more consistent and targeted control of drug dose over time, decreased frequency of drug administration, and better subject compliance. Importantly, a formulation for forming an extended-release hydrogel that can be injected through a cannula or needle, in particular a cannula or needle with a smaller diameter, could be directed into a wide variety of anatomical spaces, which would be clinically advantageous. For example, formulations for forming an extended-release hydrogel comprising a pharmaceutically active agent could be administered nearly anywhere in the body in a variety of ways, including but not limited to, topical, epidermal, subdermal, intra-adipose, intramuscular, intra-peritoneal, intravenous, intra-arterial, intracranial, intranasal, and/or intrauterine. In addition, targeted therapy through injection of a formulation that forms an extended-release hydrogel comprising a pharmaceutically active agent into an organ directly, the wall of an organ, or into the surrounding fascia or connective tissue of an organ would be desirable and beneficial.

Targeted extended release of a pharmaceutically active agent is particularly compelling when the target tissue is difficult to access clinically, a sensitive area, and/or where repeat access is invasive or burdensome to the subject. One compelling example is the eye. The structure of the mammalian eye is divided into two segments: the anterior and posterior. The anterior segment or anterior cavity is the front third of the eye and includes the cornea, iris, ciliary body, and lens. The posterior segment or posterior cavity is the back two-thirds of the eye and includes the choroid, retina, optic nerve, and vitreous humor. There are a number of disease conditions that affect the back of the eye and impact vision, including age-related macular degeneration (AMD), proliferative diabetic retinopathy, proliferative vitreoretinopathy, ocular malignancies, inherited retinal diseases, diabetic macular edema, macular edema from retinal vein occlusions, choroidal neovascularization, uveitis, amongst others.

Typical routes for administration of pharmaceutically active agents (e.g., drugs) to the eye include topical, systemic, subcutaneous, intravitreal, subretinal, intraocular, intracameral, suprachoroidal, subconjunctival, subtenon, intracanalicular, periobulbar and retrobulbar.

Effective delivery of pharmaceutically active agents for treatment of back-of-the-eye diseases remains a challenge. Delivery to the posterior segment of the eye is typically achieved via an intravitreal injection, the periocular route, implant, or by systemic administration. However, physiologic barriers to transport of the pharmaceutically active agents to the posterior segment from routes other than intravitreal injection often make their use impractical.

Intravitreal injection is often carried out with a 30 gauge or similar needle. While intravitreal injections offer high concentrations of pharmaceutically active agent to the vitreous chamber and retina, they can be associated with various short term complications such as retinal detachment, inflammation, elevated intraocular pressure, endophthalmitis and intravitreal hemorrhage. Injection of small particles within the vitreous may lead to wide dispersal of the particles which can obstruct vision (experienced by the patient as "floaters"). Additionally, many current formulations for administration of a pharmaceutically active agent to the eye often require frequent repeat injections (e.g., monthly), thus increasing the risk of complications and resulting in a substantial burden on both the patient and the healthcare system in general.

A profound need exists for targeted extended-release pharmaceutically active agent delivery formulations, in particular, formulations that can be injected into sensitive/delicate tissues, including the eye. Formulations that provide for in-situ formation of hydrogels that provide extended-release of pharmaceutically active agents within the body can provide for longer-lasting drug delivery, minimize the risks of repeated administrations, such as injections, deliver more consistent and targeted doses, limit side effects, and decrease the substantial burden placed on the patient by repeat drug administration.

SUMMARY OF THE INVENTION

Polymer-pharmaceutically active agent formulations for treating clinical disorders, wherein the polymer-pharmaceutically active agent formulations form an extended-release hydrogel containing a pharmaceutically active agent in the desired tissue of a subject, are provided. The extended-release hydrogel is formed by reaction of (a) a nucleo-functional polymer that is a biocompatible polymer containing (i) plurality of —OH groups and (ii) a plurality of thio-functional groups —$R^1$—SH wherein $R^1$ is an ester-containing linker and (b) an electro-functional polymer that is a biocompatible polymer containing at least one thiol-reactive group, such as an alpha-beta unsaturated ester. In certain embodiments, formulations are provided comprising a nucleo-functional polymer, an electro-functional polymer and a pharmaceutically active agent in a pharmaceutically acceptable carrier. In some embodiments, formulations are provided comprising a nucleo-functional polymer and a pharmaceutically active agent in a pharmaceutically acceptable carrier. In certain embodiments, formulations are provided comprising an electro-functional polymer and a pharmaceutically active agent in a pharmaceutically acceptable carrier. In some embodiments, the nucleo-functional polymer and electro-functional polymer formulations are desirably low-viscosity solutions that can be injected easily into the target tissue of a subject through a narrow-gauge needle, thereby permitting administration of the polymers while minimizing trauma to certain sensitive structures, like injection into the subject's eye. In certain embodiments, the nucleo-functional polymer and electro-functional polymer begin to react once mixed; the reaction between the nucleo-functional polymer and electro-functional polymer to create an extended-release hydrogel comprising a pharmaceutically active agent occurs when the polymers are mixed prior to delivery to the subject's target site, as they are delivered to the subject's target site, and/or within the target site of the subject thereby forming a hydrogel in situ in the target site of the subject that immobilizes the pharmaceutical agent from immediate dispersal and provides for extended-release of the pharmaceutical agent.

During degradation of the extended-release hydrogel, the pharmaceutically active agent diffuses out of the hydrogel and into the local environment over a period of time, i.e., extended-release, that provides for therapeutically effective longer-term therapy than what would be achieved by injection of the pharmaceutically active agent alone. In certain embodiments the pharmaceutically active agent may be dissolved in the extended-release hydrogel-forming formulation, suspended within the extended-release hydrogel-forming formulation and/or encapsulated within a particle and dispersed within the extended-release hydrogel-forming formulation. In certain embodiments, features of the extended-release hydrogel-forming formulation and/or extended-release hydrogel include: materials that are non-toxic, varying crosslink density or porosity, varying reaction kinetics and varying biodegradation rate, all of which are appropriate to the desired method of administration, the desired target site in the subject, and the timeframe desired for the extended-release of the pharmaceutical into the environment surrounding the target site.

The following embodiments recite non-limiting permutations of combinations of features of the inventions described. Other permutations of combinations of features are also contemplated and/or described throughout the disclosure. In particular, each of these numbered embodiments is contemplated as depending from or relating to every previous or subsequent numbered embodiment, independent of the listed order.

E1. A formulation for forming an extended-release hydrogel, the formulation comprising: a. a nucleo-functional polymer that is a biocompatible polymer containing a plurality of thio-functional groups —$R^1$—SH wherein $R^1$ is an ester-containing linker; b. an electro-functional polymer that is a biocompatible polymer containing at least one thiol-reactive group; c. a pharmaceutical agent; and d. a pharmaceutically acceptable carrier. E2. The formulation of embodiment E1, wherein the nucleo-functional polymer is a biocompatible polymer comprising poly(vinyl alcohol). E3. The formulation of embodiment E1 or E2, wherein the nucleo-functional polymer comprises a biocompatible poly(vinyl alcohol) polymer substituted by a plurality of thio-functional groups —$R^1$—SH. E4. The formulation of any of embodiments E1-E3, wherein the nucleo-functional polymer comprises a biocompatible, partially hydrolyzed poly(vinyl alcohol). E5. The formulation of embodiment E4, wherein the partially hydrolyzed poly(vinyl alcohol) polymer has a degree of hydrolysis in the range of about 75% to about 99.9%. E6. The formulation of any one of embodiments E1-E5, wherein the thio-functional group —$R^1$—SH is —OC(O)—($C_1$-$C_6$ alkylene)-SH. E7. The formulation of any one of embodiments E1-E6, wherein the thio-functional group —$R^1$—SH is —OC(O)—($CH_2CH_2$)—SH. E8. The formulation of embodiment 1, wherein the nucleo-functional polymer is a biocompatible poly(vinyl alcohol) polymer comprising:

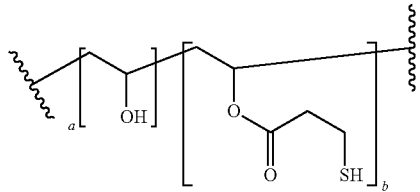

wherein a is an integer from 1 to about 20 and b is an integer from 1 to about 20. E9. The formulation of embodiment 1, wherein the nucleo-functional polymer is a biocompatible poly(vinyl alcohol) polymer comprising:

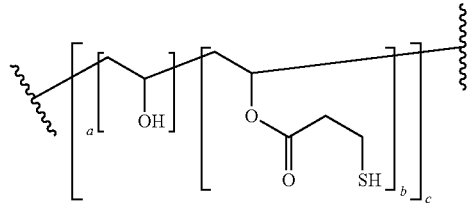

wherein a is an integer from 1 to about 20, b is an integer from 1 to about 20, and c is an integer from about 20 to about 500. E10. The formulation of any one of embodiments E1-E9, wherein the nucleo-functional polymer has a weight-average molecular weight in the range of from about 4,000 g/mol to about 100,000 g/mol. E11. The formulation of any one of embodiments E1-E10, wherein the nucleo-functional polymer has a weight-average molecular weight in the range of from about 15,000 g/mol to about 25,000 g/mol. E12. The formulation of any one of embodiments E1-E9, wherein the nucleo-functional polymer has a weight-average molecular weight of less than about 75,000 g/mol. E13. The formulation of any one of embodiments E1-E12, wherein the electro-functional polymer is a biocompatible polymer comprising poly(ethylene glycol). E14. The formulation of any one of embodiments E1-E13, wherein the electro-functional polymer is a biocompatible polymer comprising poly(ethylene glycol)polymer substituted by at least one thiol-reactive group. E15. The formulation of any one of embodiments E1-E14, wherein the thiol-reactive group is an alpha-beta unsaturated ester, maleimidyl, sulfone, or combinations thereof. E16. The formulation of embodiment E15, wherein the alpha-beta unsaturated ester, maleimidyl, or sulfone is optionally substituted by one or more occurrences of alkyl, aryl, or aralkyl. E17. The formulation of any one of embodiments E1-E16, wherein the thiol-reactive group is acrylate, maleimide, or vinylsulfone. E18. The formulation of any one of embodiments E1-E17, wherein the electro-functional polymer has a weight-average molecular weight in the range of from about 500 g/mol to about 100,000 g/mol. E19. The formulation of any one of embodiments E1-E18, wherein the electro-functional polymer has a weight-average molecular weight in the range of from about 1,000 g/mol to about 50,000 g/mol. E20. The formulation of any one of embodiments E1-E19, wherein the electro-functional polymer has a weight-average molecular weight in the range of from about 2,000 g/mol to about 20,000 g/mol. E21. The formulation of any one of embodiments E1-E20, wherein the electro-functional polymer has a weight-average molecular weight in the range of from about 2,700 g/mol to about 3,000 g/mol. E22. The formulation of any one of embodiments E1-E20, wherein the electro-functional polymer has a weight-average molecular weight in the range of from about 9,000 g/mol to about 11,000 g/mol. E23. The formulation of any one of embodiments E1-E19, wherein the electro-functional polymer has a weight-average molecular weight in the range of from about 18,000 g/mol to about 22,000 g/mol. E24. The formulation of any one of embodiments E1-E23, wherein the electro-functional polymer comprises a multi-arm polymer. E25. The formulation of embodiment E24, wherein the multi-arm polymer comprises as 4-arm polyethylene glycol maleimide, 4-arm polyethylene glycol acrylate, 4-arm polyethylene glycol vinyl sulfone, 8-arm polyethylene glycol maleimide, 8-arm polyethylene glycol acrylate, 8-arm polyethylene glycol vinyl sulfone, or combinations thereof. E26. The formulation of any one of embodiments E1-E25, wherein the mole ratio of (i) thio-functional groups —$R^1$—SH to (ii) thiol-reactive group is in the range of about 10:1 to about 1:10. E27. The formulation of any one of embodiments E1-E26, wherein the mole ratio of (i) thio-functional groups —$R^1$—SH to (ii) thiol-reactive groups is in the range of about 2:1 to about 1:2. E28. The formulation of any one of embodiments E1-E25, wherein the mole ratio of (i) thio-functional groups —$R^1$—SH to (ii) thiol-reactive groups is in the range of about 0.8:1 to about 1.2:1. E29. The formulation of any one of embodiments E1-E28, wherein the formulation comprises water, and the formulation has a pH in the range of about 7.1 to about 7.7. E30. The formulation of any one of embodiments E1-E28, wherein the formulation comprises water, and the formulation has a pH in the range of about 7.3 to about 7.5. E31. The formulation of any one of embodiments E1-E28, wherein the formulation comprises water, and the formulation has a pH of about 7.4. E32. The formulation of any one of embodiments E1-E31, further comprising an alkali metal salt. E33. The formulation of any one of embodiments E1-E32, further comprising an alkali metal halide salt, an alkaline earth metal halide salt, or a combination thereof. E34. The formulation of any one of embodiments E1-E33, further comprising sodium chloride, potassium chloride, calcium chloride, magnesium chloride, or a combination thereof. E35. The formulation of any one of embodiments E1-E34, wherein the formulation has an osmolality in the range of about 200 mOsm/kg to about 400 mOsm/kg. E36. The formulation of any one of embodiments E1-E35, wherein the formulation has an osmolality in the range of about 250 mOsm/kg to about 350 mOsm/kg. E37. The formulation of any one of embodiments E1-E36, wherein the formulation has an osmolality in the range of about 280 mOsm/kg to about 320 mOsm/kg. E38. The formulation of any one of embodiments E1-E37, wherein the formulation has an osmolality of about 300 mOsm/kg. E39. The formulation of any one of embodiments E1-E38, wherein the formulation has an endotoxin level of less than about 20 endotoxin units/ml, less than about 15 endotoxin units/ml, less than about 10 endotoxin units/ml, less than about 5 endotoxin units/ml, less than about 2.5 endotoxin units/ml, less than about 1.0 endotoxin units/ml, less than about 0.8 endotoxin units/ml, less than about 0.5 endotoxin units/ml, less than about 0.2 endotoxin units/ml, or less than about 0.1 endotoxin units/ml. E40. The formulation of any one of embodiments E1-E39, wherein the formulation has less than about 50 particles per mL with a size of $\geq 10$ μm. E41. The formulation of any one of embodiments E1-E39, wherein the formulation has less than about 5 particles per mL with a size of $\geq 25$ μm. E42. The formulation of any one of embodiments E1-E41, wherein the hydrogel formed by the formulation has a transparency of at least about 80% for light in the visible spectrum when measured through a hydrogel having a thickness of 2 cm. E43. The formulation of any one of embodiments E1-E42, wherein the hydrogel formed by the formulation has a transparency of at least about 85% for light in the visible spectrum when measured through a hydrogel having a thickness of 2 cm. E44. The formulation of any one of embodiments E1-E43, wherein the hydrogel formed by the formulation has a transparency or at least about 90% for light in the visible spectrum when measured through a hydrogel having a thickness of 2 cm. E45. The formulation of any one of embodiments E1-E44, wherein the hydrogel formed by the formulation has a crosslink time of less than about 10 minutes, less than about 7 minutes, less than about 5 minutes, less than about 3 minutes, less than about 1 minute, less than about 20 seconds, less than about 10 seconds, less than about 5 seconds, or less than about 1 second when measured at 37° C. E46. The formulation of any one of embodiments E1-E45, wherein the hydrogel formed by the formulation has a degradation time that is greater than or equal to about 3, about 5, about 8, about 10, about 13, about 14, about 15, about 19, or about 32 days at 60° C. E47. The formulation of any one of embodiments E1-E45, wherein the hydrogel formed by the formulation has a degradation time that is greater than or equal to about 20, about 40, about 60, about 69, about 80, about 94, about 100, or about 158 days at 37° C. E48. The formulation of any one of embodiments E1-E47, wherein the hydrogel formed by the formulation acts as a depot for the pharmaceutical agent. E49. The formulation of any one of embodiments E1-E48, wherein the hydrogel formed by the formulation provides for extended-release of the pharmaceutical agent. E50. The formulation of any one of embodiments E1-E49, wherein the hydrogel formed by the formulation releases the pharmaceutical agent over a period of at least about 5, about 10, about 20, about 30, about 40, about 50, about 60, about 70, about 80, about 90, about 100, or about 120 days. E51. The formulation of any one of embodiments E1-E50, wherein complete release of the pharmaceutical agent from the hydrogel formed by the formulation is achieved after at least about 10, about 20, about 30, about 40, about 50, about 60, about 70, about 80, about 90, about 100, about 110, about 120, about 130 days. E52. The formulation of any one of embodiments E1-E51, where the hydrogel formed by the formulation comprises a nearly first-order release of the pharmaceutical agent. E53. The formulation of any one of embodiments E1-E52, wherein the formulation has a viscosity of less than about 4000 cP, about 2000 cP, about 1000 cP, about 800 cP, about 600 cP, about 500 cP, about 400 cP, about 200 cP, about 100 cP, about 80 cP, about 60 cP, about 50 cP, about 40 cP, about 20 cP, about 10 cP, about 8 cP, about 6 cP, about 5 cP, about 4 cP, about 3 cP, about 2 cP about 1 cP prior to formation of the hydrogel. E54. The formulation of any one of embodiments E1-E53, wherein the pharmaceutical agent comprises an anti-inflammatory agent, a steroid, an NSAID, an intraocular pressure lowering drug, an antibiotic, a pain reliever, an inhibitor of vascular endothelial growth factor (VEGF), an inhibitor of abnormal vascular growth or vascular leakage, an inhibitor or modifier of the complement pathway, a neuroprotectant, an inhibitor of abnormal cell proliferation, a chemotherapeutic, an antiviral drug, a gene therapy viral vector, or a combination thereof. E55. The formulation of any one of embodiments E1-E54, wherein the pharmaceutical agent comprises a small molecule, a protein, a DNA or RNA fragment, a glycosaminoglycan, a carbohydrate, a nucleic acid, an inorganic and organic biologically active compound, an active portion of any of the proceeding, or a combination thereof. E56. The formulation of any one of embodiments E1-E55, wherein the pharmaceutical agent comprises an antibody, a bi-specific antibody, a single-chain variable fragment (scFv), an active portion of any of the proceeding, or a combination thereof. E57. The formulation of any one of embodiments E1-E56, wherein the pharmaceutical agent comprises an anti-cancer agent. E58. The formulation of any one of embodiments E1-E57, wherein the pharmaceutical agent comprises bevacizumab. E59. The formulation of any one of embodiments E1-E58, wherein the pharmaceutically acceptable carrier comprises water. E60. The formulation of any one of embodiments E1-E59, wherein the pharmaceutically acceptable carrier comprises PBS. E61. The formulation of embodiment 60, wherein the PBS comprises one or more of sodium chloride, potassium chloride, sodium phosphate and potassium phosphate. E62. The formulation of any one of embodiments E1-E61, wherein the formulation is an ocular formulation.

E63. A formulation for use in forming an extended-release hydrogel, the formulation comprising: a. a nucleo-functional polymer that is a biocompatible polymer containing a plurality of thio-functional groups —R$^1$—SH wherein R$^1$ is an ester-containing linker; b. a pharmaceutical agent; and c. a pharmaceutically acceptable carrier. E64. The formulation of embodiment 63, wherein the nucleo-functional polymer is a biocompatible polymer comprising poly(vinyl alcohol). E65. The formulation of embodiment 63 or 64, wherein the nucleo-functional polymer comprises a biocompatible poly (vinyl alcohol) polymer substituted by a plurality of thio-functional groups —R$^1$—SH. E66. The formulation of any one of embodiments E63-E65, wherein the nucleo-functional polymer comprises a biocompatible, partially hydrolyzed poly(vinyl alcohol). E67. The formulation of embodiment 66, wherein the partially hydrolyzed poly(vinyl alcohol) polymer has a degree of hydrolysis in the range of about 75% to about 99.9%. E68. The formulation of any one of embodiments E63-E67, wherein the thio-functional group —R$^1$—SH is —OC(O)—(C$_1$-C$_6$ alkylene)-SH. E69. The formulation of any one of embodiments E63-E68, wherein the thio-functional group —R$^1$—SH is —OC(O)—(CH$_2$CH$_2$)—SH. E70. The formulation of embodiment 63, wherein the nucleo-functional polymer is a biocompatible poly(vinyl alcohol) polymer comprising:

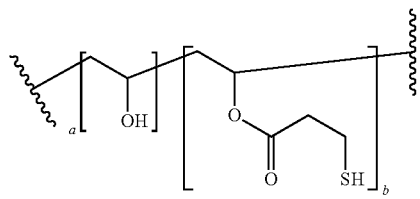

wherein a is an integer from 1 to about 20 and b is an integer from 1 to about 20. E71. The formulation of embodiment 63, wherein the nucleo-functional polymer is a biocompatible poly(vinyl alcohol) polymer comprising:

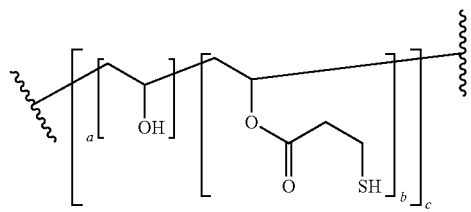

wherein a is an integer from 1 to about 20, b is an integer from 1 to about 20, and c is an integer from about 20 to about 500. E72. The formulation of any one of embodiments E63-E71, wherein the nucleo-functional polymer has a weight-average molecular weight in the range of from about 4,000 g/mol to about 100,000 g/mol. E73. The formulation of any one of embodiments E63-E72, wherein the nucleo-functional polymer has a weight-average molecular weight in the range of from about 15,000 g/mol to about 25,000 g/mol. E74. The formulation of any one of embodiments E63-E71, wherein the nucleo-functional polymer has a weight-average molecular weight of less than about 75,000 g/mol. E75. The formulation of any one of embodiments E63-E74, wherein the formulation comprises water, and the formulation has a pH in the range of about 7.1 to about 7.7. E76. The formulation of any one of embodiments E63-E75, wherein the formulation comprises water, and the formulation has a pH in the range of about 7.3 to about 7.5. E77. The formulation of any one of embodiments E63-E76, wherein the formulation comprises water, and the formulation has a pH of about 7.4. E78. The formulation of any one of embodiments E63-E77, further comprising an alkali metal salt. E79. The formulation of any one of embodiments E63-E78, further comprising an alkali metal halide salt, an alkaline earth metal halide salt, or a combination thereof. E80. The formulation of any one of embodiments E63-E79, further comprising sodium chloride, potassium chloride, calcium chloride, magnesium chloride, or a combination thereof. E81. The formulation of any one of embodiments E63-E80, wherein the formulation has an osmolality in the range of about 200 mOsm/kg to about 400 mOsm/kg. E82. The formulation of any one of embodiments E63-E81, wherein the formulation has an osmolality in the range of about 250 mOsm/kg to about 350 mOsm/kg. E83. The formulation of any one of embodiments E63-E82, wherein the formulation has an osmolality in the range of about 280 mOsm/kg to about 320 mOsm/kg. E84. The formulation of any one of embodiments E63-E83, wherein the formulation has an osmolality of about 300 mOsm/kg. E85. The formulation of any one of embodiments E63-E84, wherein the formulation has an endotoxin level of less than about 20 endotoxin units/ml, less than about 15 endotoxin units/ml, less than about 10 endotoxin units/ml, less than about 5 endotoxin units/ml, less than about 2.5 endotoxin units/ml, less than about 1.0 endotoxin units/ml, less than about 0.8 endotoxin units/ml, less than about 0.5 endotoxin units/ml, less than about 0.2 endotoxin units/ml, or less than about 0.1 endotoxin units/ml. E86. The formulation of any one of embodiments E63-E85, wherein the formulation has less than about 50 particles per mL with a size of ≥10 μm. E87. The formulation of any one of embodiments E63-E86, wherein the formulation has less than about 5 particles per mL with a size of ≥25 μm. E88. The formulation of any one of embodiments E63-E87, wherein the formulation has a viscosity of less than about 4000 cP, about 2000 cP, about 1000 cP, about 800 cP, about 600 cP, about 500 cP, about 400 cP, about 200 cP, about 100 cP, about 80 cP, about 60 cP, about 50 cP, about 40 cP, about 20 cP, about 10 cP, about 8 cP, about 6 cP, about 5 cP, about 4 cP, about 3 cP, about 2 cP about 1 cP prior to formation of the hydrogel. E89. The formulation of any one of embodiments E63-E88, wherein the pharmaceutical agent comprises an anti-inflammatory agent, a steroid, an NSAID, an intraocular pressure lowering drug, an antibiotic, a pain reliever, an inhibitor of vascular endothelial growth factor (VEGF), an inhibitor of abnormal vascular growth or vascular leakage, an inhibitor of abnormal cell proliferation, a chemotherapeutic, an anti-viral drug, a gene therapy viral vector, or a combination thereof. E90. The formulation of any one of embodiments E63-E89, wherein the pharmaceutical agent comprises a small molecule, a protein, a DNA or RNA fragment, a glycosaminoglycan, a carbohydrate, a nucleic acid, an inorganic and organic biologically active compound, an active portion of any of the proceeding, or a combination thereof. E91. The formulation of any one of embodiments E63-E90, wherein the pharmaceutical agent comprises an antibody, a bi-specific antibody, a single-chain variable fragment (scFv), an active portion of any of the proceeding, or a combination thereof. E92. The formulation of any one of embodiments E63-E91, wherein the pharmaceutical agent comprises an anti-cancer agent. E93. The formulation of any one of embodiments E63-E92, wherein the pharmaceutical agent comprises bevacizumab. E94. The formulation of any one of embodiments E63-E93, wherein the pharmaceutically acceptable carrier comprises water. E95. The formulation of any one of embodiments E63-E94, wherein the pharmaceutically acceptable carrier comprises PBS. E96. The formulation of embodiment 95, wherein the PBS comprises one or more of sodium chloride, potassium chloride, sodium phosphate and potassium phosphate. E97. The formulation of any one of embodiments E63-E96, wherein the formulation is an ocular formulation.

E98. A formulation for forming an extended-release hydrogel, the formulation comprising: a. an electro-functional polymer that is a biocompatible polymer containing at least one thiol-reactive group; b. a pharmaceutical agent; and c. a pharmaceutically acceptable carrier. E99. The formulation of embodiment 98, wherein the electro-functional polymer is a biocompatible polymer comprising poly(ethylene glycol). E100. The formulation of embodiment 98 or 99, wherein the electro-functional polymer is a biocompatible polymer comprising poly(ethylene glycol)polymer substituted by at least one thiol-reactive group. E101. The formulation of any one of embodiments E98-E100, wherein the thiol-reactive group is an alpha-beta unsaturated ester, maleimidyl, sulfone, or combinations thereof. E102. The formulation of embodiment 101, wherein the alpha-beta unsaturated ester, maleimidyl, or sulfone is optionally substituted by one or more occurrences of alkyl, aryl, or aralkyl. E103. The formulation of any one of embodiments E98-E102, wherein the thiol-reactive group is acrylate, maleimide, or vinylsulfone. E104. The formulation of any one of embodiments E98-E103, wherein the electro-functional polymer has a weight-average molecular weight in the range of from about 500 g/mol to about 100,000 g/mol. E105. The formulation of any one of embodiments E98-E104, wherein the electro-functional polymer has a weight-average molecular weight in the range of from about 1,000 g/mol to about 50,000 g/mol. E106. The formulation of any one of embodiments E98-E105, wherein the electro-functional polymer has a weight-average molecular weight in the range of from about 2,000 g/mol to about 20,000 g/mol. E107. The formulation of any one of embodiments E98-E106, wherein the electro-functional polymer has a weight-average molecular weight in the range of from about 2,700 g/mol to about 3,000 g/mol. E108. The formulation of any one of embodiments E98-E107, wherein the electro-functional polymer has a weight-average molecular weight in the range of from about 9,000 g/mol to about 11,000 g/mol. E109. The formulation of any one of embodiments E98-E108, wherein the electro-functional polymer has a weight-average molecular weight in the range of from about 18,000 g/mol to about 22,000 g/mol. E110. The formulation of any one of embodiments E98-E109, wherein the electro-functional polymer comprises a multi-arm polymer. E111. The formulation of embodiment 110, wherein the multi-arm polymer comprises as 4-arm polyethylene glycol maleimide, 4-arm polyethylene glycol acrylate, 4-arm polyethylene glycol vinyl sulfone, 8-arm polyethylene glycol maleimide, 8-arm polyethylene glycol acrylate, 8-arm polyethylene glycol vinyl sulfone, or combinations thereof. E112. The formulation of any one of embodiments E98-E111, wherein the formulation comprises water, and the formulation has a pH in the range of about 7.1 to about 7.7. E113. The formulation of any one of embodiments E98-E112, wherein the formulation comprises water, and the formulation has a pH in the range of about 7.3 to about 7.5. E114. The formulation of any one of embodiments E98-E113, wherein the formulation comprises water, and the formulation has a pH of about 7.4. E115. The formulation of any one of embodiments E98-E114, further comprising an alkali metal salt. E116. The formulation of any one of embodiments E98-E115, further comprising an alkali metal halide salt, an alkaline earth metal halide salt, or a combination thereof. E117. The formulation of any one of embodiments E98-E116, further comprising sodium chloride, potassium chloride, calcium chloride, magnesium chloride, or a combination thereof. E118. The formulation of any one of embodiments E98-E117, wherein the formulation has an osmolality in the range of about 200 mOsm/kg to about 400 mOsm/kg. E119. The formulation of any one of embodiments E98-E118, wherein the formulation has an osmolality in the range of about 250 mOsm/kg to about 350 mOsm/kg. E120. The formulation of any one of embodiments E98-E119, wherein the formulation has an osmolality in the range of about 280 mOsm/kg to about 320 mOsm/kg. E121. The formulation of any one of embodiments E98-E120, wherein the formulation has an osmolality of about 300 mOsm/kg. E122. The formulation of any one of embodiments E98-E121, wherein the formulation has an endotoxin level of less than about 20 endotoxin units/ml, less than about 15 endotoxin units/ml, less than about 10 endotoxin units/ml, less than about 5 endotoxin units/ml, less than about 2.5 endotoxin units/ml, less than about 1.0 endotoxin units/ml, less than about 0.8 endotoxin units/ml, less than about 0.5 endotoxin units/ml, less than about 0.2 endotoxin units/ml, or less than about 0.1 endotoxin units/ml. E123. The formulation of any one of embodiments E98-E122, wherein the formulation has less than about 50 particles per mL with a size of ≥10 μm. E124. The formulation of any one of embodiments E98-E123, wherein the formulation has less than about 5 particles per mL with a size of ≥25 μm. E125. The formulation of any one of embodiments E98-E124, wherein the formulation has a viscosity of less than about 4000 cP, about 2000 cP, about 1000 cP, about 800 cP, about 600 cP, about 500 cP, about 400 cP, about 200 cP, about 100 cP, about 80 cP, about 60 cP, about 50 cP, about 40 cP, about 20 cP, about 10 cP, about 8 cP, about 6 cP, about 5 cP, about 4 cP, about 3 cP, about 2 cP about 1 cP prior to formation of the hydrogel. E126. The formulation of any one of embodiments E98-E125, wherein the pharmaceutical agent comprises an anti-inflammatory agent, a steroid, an NSAID, an intraocular pressure lowering drug, an antibiotic, a pain reliever, an inhibitor of vascular endothelial growth factor (VEGF), an inhibitor of abnormal vascular growth or vascular leakage, an inhibitor of abnormal cell proliferation, a chemotherapeutic, an anti-viral drug, a gene therapy viral vector, or a combination thereof. E127. The formulation of any one of embodiments E98-E126, wherein the pharmaceutical agent comprises a small molecule, a protein, a DNA or RNA fragment, a glycosaminoglycan, a carbohydrate, a nucleic acid, an inorganic and organic biologically active compound, an active portion of any of the proceeding, or a combination thereof. E128. The formulation of any one of embodiments E98-E127, wherein the pharmaceutical agent comprises an antibody, a bi-specific antibody, a single-chain variable fragment (scFv), an active portion of any of the proceeding, or a combination thereof. E129. The formulation of any one of embodiments E98-E128, wherein the pharmaceutical agent comprises an anti-cancer agent. E130. The formulation of any one of embodiments E98-E129, wherein the pharmaceutical agent comprises bevacizumab. E131. The formulation of any one of embodiments E98-E130, wherein the pharmaceutically acceptable carrier comprises water. E132. The formulation of any one of embodiments E98-E131, wherein the pharmaceutically acceptable carrier comprises PBS. E133. The formulation of embodiment 132, wherein the PBS comprises one or more of sodium chloride, potassium chloride, sodium phosphate and potassium phosphate. E134. The formulation of any one of embodiments E98-E133, wherein the formulation is an ocular formulation.

E135. An extended-release hydrogel comprising: a. a nucleo-functional polymer that is a biocompatible polymer containing a plurality of thio-functional groups —R1—SH wherein R1 is an ester-containing linker; b. an electro-functional polymer that is a biocompatible polymer containing at least one thiol-reactive group; and c. a pharmaceutical agent. E136. The extended-release hydrogel of embodiment 135, further comprising a pharmaceutically acceptable carrier. E137. The extended-release hydrogel of embodiment 135 or 136, wherein the nucleo-functional polymer is a biocompatible polymer comprising poly(vinyl alcohol). E138. The extended-release hydrogel of any of embodiments E135-E137, wherein the nucleo-functional polymer comprises a biocompatible poly(vinyl alcohol) polymer substituted by a plurality of thio-functional groups —R$^1$—SH. E139. The extended-release hydrogel of any of embodiments E135-E138, wherein the nucleo-functional polymer comprises a biocompatible, partially hydrolyzed poly(vinyl alcohol). E140. The extended-release hydrogel of embodiment 139, wherein the partially hydrolyzed poly(vinyl alcohol) polymer has a degree of hydrolysis in the range of about 75% to about 99.9%. E141. The extended-release hydrogel of any one of embodiments E135-E140, wherein the thio-functional group —R$^1$—SH is —OC(O)—(C$_1$-C$_6$ alkylene)-SH. E142. The extended-release hydrogel of any one of embodiments E135-E141, wherein the thio-functional group —R$^1$—SH is —OC(O)—(CH$_2$CH$_2$)—SH. E143. The extended-release hydrogel of embodiment 135, wherein the nucleo-functional polymer is a biocompatible poly(vinyl alcohol) polymer comprising:

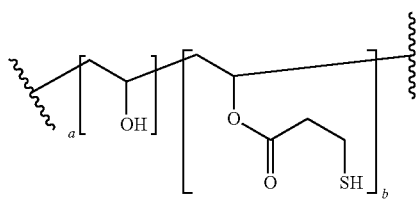

wherein a is an integer from 1 to about 20 and b is an integer from 1 to about 20. E144. The extended-release hydrogel of embodiment 135, wherein the nucleo-functional polymer is a biocompatible poly(vinyl alcohol) polymer comprising:

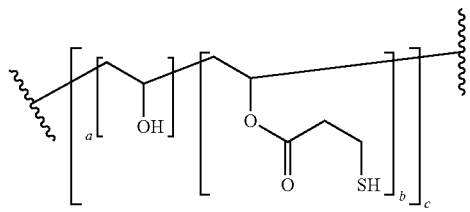

wherein a is an integer from 1 to about 20, b is an integer from 1 to about 20, and c is an integer from about 20 to about 500. E145. The extended-release hydrogel of any one of embodiments E135-E144, wherein the nucleo-functional polymer has a weight-average molecular weight in the range of from about 4,000 g/mol to about 100,000 g/mol. E146. The extended-release hydrogel of any one of embodiments E135-E145, wherein the nucleo-functional polymer has a weight-average molecular weight in the range of from about 15,000 g/mol to about 25,000 g/mol. E147. The extended-release hydrogel of any one of embodiments E135-E145, wherein the nucleo-functional polymer has a weight-average molecular weight of less than about 75,000 g/mol. E148. The extended-release hydrogel of any one of embodiments E135-E147, wherein the electro-functional polymer is a biocompatible polymer comprising poly(ethylene glycol). E149. The extended-release hydrogel of any one of embodiments E135-E148, wherein the electro-functional polymer is a biocompatible polymer comprising poly(ethylene glycol) polymer substituted by at least one thiol-reactive group. E150. The extended-release hydrogel of any one of embodiments E135-E149, wherein the thiol-reactive group is an alpha-beta unsaturated ester, maleimidyl, sulfone, or combinations thereof. E151. The extended-release hydrogel of embodiment 150, wherein the alpha-beta unsaturated ester, maleimidyl, or sulfone is optionally substituted by one or more occurrences of alkyl, aryl, or aralkyl. E152. The extended-release hydrogel of any one of embodiments E135-E151, wherein the thiol-reactive group is acrylate, maleimide, or vinylsulfone. E153. The extended-release hydrogel of any one of embodiments E135-E152, wherein the electro-functional polymer has a weight-average molecular weight in the range of from about 500 g/mol to about 100,000 g/mol. E154. The extended-release hydrogel of any one of embodiments E135-E153, wherein the electro-functional polymer has a weight-average molecular weight in the range of from about 1,000 g/mol to about 50,000 g/mol. E155. The extended-release hydrogel of any one of embodiments E135-E154, wherein the electro-functional polymer has a weight-average molecular weight in the range of from about 2,000 g/mol to about 20,000 g/mol. E156. The extended-release hydrogel of any one of embodiments E135-E155, wherein the electro-functional polymer has a weight-average molecular weight in the range of from about 2,700 g/mol to about 3,000 g/mol. E157. The extended-release hydrogel of any one of embodiments E135-E156, wherein the electro-functional polymer has a weight-average molecular weight in the range of from about 9,000 g/mol to about 11,000 g/mol. E158. The extended-release hydrogel of any one of embodiments E135-E157, wherein the electro-functional polymer has a weight-average molecular weight in the range of from about 18,000 g/mol to about 22,000 g/mol. E159. The extended-release hydrogel of any one of embodiments E135-E158, wherein the electro-functional polymer comprises a multi-arm polymer. E160. The extended-release hydrogel of embodiment 159, wherein the multi-arm polymer comprises as 4-arm polyethylene glycol maleimide, 4-arm polyethylene glycol acrylate, 4-arm polyethylene glycol vinyl sulfone, 8-arm polyethylene glycol maleimide, 8-arm polyethylene glycol acrylate, 8-arm polyethylene glycol vinyl sulfone, or combinations thereof. E161. The extended-release hydrogel of any one of embodiments E135-E160, wherein the mole ratio of (i) thio-functional groups —$R^1$—SH to (ii) thiol-reactive group is in the range of about 10:1 to about 1:10. E162. The extended-release hydrogel of any one of embodiments E135-E161, wherein the mole ratio of (i) thio-functional groups —$R^1$—SH to (ii) thiol-reactive groups is in the range of about 2:1 to about 1:2. E163. The extended-release hydrogel of any one of embodiments E135-E161, wherein the mole ratio of (i) thio-functional groups —$R^1$—SH to (ii) thiol-reactive groups is in the range of about 0.8:1 to about 1.2:1. E164. The extended-release hydrogel of any one of embodiments E135-E163, wherein the formulation comprises water, and the formulation has a pH in the range of about 7.1 to about 7.7. E165. The extended-release hydrogel of any one of embodiments E135-E163, wherein the formulation comprises water, and the formulation has a pH in the range of about 7.3 to about 7.5. E166. The extended-release hydrogel of any one of embodiments E135-E163, wherein the formulation comprises water, and the formulation has a pH of about 7.4. E167. The extended-release hydrogel of any one of embodiments E135-E166, further comprising an alkali metal salt. E168. The extended-release hydrogel of any one of embodiments E135-E167, further comprising an alkali metal halide salt, an alkaline earth metal halide salt, or a combination thereof. E169. The extended-release hydrogel of any one of embodiments E135-E168, further comprising sodium chloride, potassium chloride, calcium chloride, magnesium chloride, or a combination thereof. E170. The extended-release hydrogel of any one of embodiments E135-E161, wherein the extended-release hydrogel has a transparency of at least about 80% for light in the visible spectrum when measured through a hydrogel having a thickness of 2 cm. E171. The extended-release hydrogel of any one of embodiments E135-E170, wherein the extended-release hydrogel has a transparency of at least about 85% for light in the visible spectrum when measured through a hydrogel having a thickness of 2 cm. E172. The extended-release hydrogel of any one of embodiments E135-E171, wherein the extended-release hydrogel has a transparency or at least about 90% for light in the visible spectrum when measured through a hydrogel having a thickness of 2 cm. E173. The extended-release hydrogel of any one of embodiments E135-E172, wherein the extended-release hydrogel has a crosslink time of less than about 10 minutes, less than about 7 minutes, less than about 5 minutes, less than about 3 minutes, less than about 1 minute, less than about 20 seconds, less than about 10 seconds, less than about 5 seconds, or less than about 1 second after mixing the nucleo-functional polymer and the electro-functional polymer when measured at 37° C. E174. The extended-release hydrogel of any one of embodiments E135-E173, wherein the extended-release hydrogel has a degradation time that is greater than or equal to about 3, about 5, about 8, about 10, about 13, about 14, about 15, about 19, or about 32 days at 60° C. E175. The extended-release hydrogel of any one of embodiments E135-E174, wherein the extended-release hydrogel has a degradation time that is greater than or equal to about 20, about 40, about 60, about 69, about 80, about 94, about 100, or about 158 days at 37° C. E176. The extended-release hydrogel of any one of embodiments E135-E175, wherein the extended-release hydrogel acts as a depot for the pharmaceutical agent. E177. The extended-release hydrogel of any one of embodiments E135-E176, wherein the extended-release hydrogel provides for extended-release of the pharmaceutical agent. E178. The extended-release hydrogel of any one of embodiments E135-E177, wherein the extended-release hydrogel releases the pharmaceutical agent over a period of at least about 5, about 10, about 20, about 30, about 40, about 50, about 60, about 70, about 80, about 90, about 100, or about 120 days. E179. The extended-release hydrogel of any one of embodiments E135-E178, wherein complete release of the pharmaceutical agent from the extended-release hydrogel is achieved after at least about 10, about 20, about 30, about 40, about 50, about 60, about 70, about 80, about 90, about 100, about 110, about 120, about 130 days. E180. The extended-release hydrogel of any one of embodiments E135-E179, where the extended-release hydrogel comprises a nearly first-order release of the pharmaceutical agent. E181. The extended-release hydrogel of any one of embodiments E135-E180, wherein the pharmaceutical agent comprises an anti-inflammatory agent, a steroid, an NSAID, an intraocular pressure lowering drug, an antibiotic, a pain reliever, an inhibitor of vascular endothelial growth factor (VEGF), an inhibitor of abnormal vascular growth or vascular leakage, an inhibitor of abnormal cell proliferation, a chemotherapeutic, an anti-viral drug, a gene therapy viral vector, or a combination thereof. E182. The extended-release hydrogel of any one of embodiments E135-E181, wherein the pharmaceutical agent comprises a small molecule, a protein, a DNA or RNA fragment, a glycosaminoglycan, a carbohydrate, a nucleic acid, an inorganic and organic biologically active compound, an active portion of any of the proceeding, or a combination thereof. E183. The extended-release hydrogel of any one of embodiments E135-E182, wherein the pharmaceutical agent comprises an antibody, a bi-specific antibody, a single-chain variable fragment (scFv), an active portion of any of the proceeding, or a combination thereof. E184. The extended-release hydrogel of any one of embodiments E135-E183, wherein the pharmaceutical agent comprises an anti-cancer agent. E185. The extended-release hydrogel of any one of embodiments E135-E184, wherein the pharmaceutical agent comprises bevacizumab. E186. The extended-release hydrogel of any one of embodiments E136-E185, wherein the pharmaceutically acceptable carrier comprises water. E187. The extended-release hydrogel of any one of embodiments E136-E186, wherein the pharmaceutically acceptable carrier comprises PBS. E188. The extended-release hydrogel of embodiment 187, wherein the PBS comprises one or more of sodium chloride, potassium chloride, sodium phosphate and potassium phosphate. E189. The extended-release hydrogel of any one of embodiments E135-188, wherein the extended-release hydrogel is for use in the eye of a subject.

E190. A method for administering a pharmaceutical agent to a subject in need thereof, the method comprising: a. administering to the subject an effective amount of a nucleo-functional polymer, an electro-functional polymer, a pharmaceutical agent, and a pharmaceutically acceptable carrier; and b. allowing the nucleo-functional polymer and the electro-functional polymer to react to form an extended-release hydrogel in the subject; wherein the nucleo-functional polymer is a biocompatible polymer containing a plurality of thio-functional groups —$R^1$—SH wherein $R^1$ is an ester-containing linker, and the electro-functional polymer is a biocompatible polymer containing at least one thiol-reactive group. E191. The method of embodiment 190, wherein the nucleo-functional polymer, the electro-functional polymer, the pharmaceutical agent, and the pharmaceutically acceptable carrier are administered to the subject together in a single formulation. E192. The method of embodiment 190, wherein the nucleo-functional polymer and the electro-functional polymer are administered to the subject in separate formulations and following administration to the subject, the nucleo-functional polymer and the electro-functional polymer mix and react to form the extended-release hydrogel in the subject. E193. The method of embodiment 192, wherein the formulation comprising the nucleo-functional polymer comprises the pharmaceutical agent. E194. The method of embodiment 192 or 193, wherein the formulation comprising the electro-functional polymer comprises the pharmaceutical agent. E195. The method of any one of embodiments E192-E194, wherein the formulation comprising the nucleo-functional polymer comprises the pharmaceutically acceptable carrier. E196. The method of any one of embodiments E192-E195, wherein the formulation comprising the electro-functional polymer comprises the pharmaceutically acceptable carrier. E197. The method of any one of embodiments E190-E196, wherein the nucleo-functional polymer is a biocompatible polymer comprising poly(vinyl alcohol). E198. The method of any one of embodiments E190-E197, wherein the nucleo-functional polymer comprises a biocompatible poly(vinyl alcohol) polymer substituted by a plurality of thio-functional groups —$R^1$—SH. E199. The method of any of embodiments E190-E198, wherein the nucleo-functional polymer comprises a biocompatible, partially hydrolyzed poly(vinyl alcohol). E200. The method of embodiment 199, wherein the partially hydrolyzed poly(vinyl alcohol) polymer has a degree of hydrolysis in the range of about 75% to about 99.9%. E201. The method of any one of embodiments E190-E200, wherein the thio-functional group —$R^1$—SH is —OC(O)—($C_1$-$C_6$ alkylene)-SH. E202. The method of any one of embodiments E190-E201, wherein the thio-functional group —$R^1$—SH is —OC(O)—($CH_2CH_2$)—SH. E203. The method of any one of embodiments E190-E196, wherein the nucleo-functional polymer is a biocompatible poly(vinyl alcohol) polymer comprising:

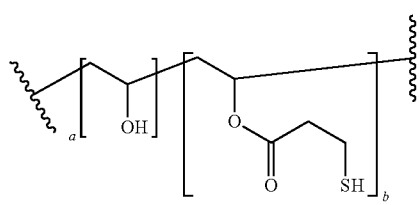

wherein a is an integer from 1 to about 20 and b is an integer from 1 to about 20. E204. The method of any one of embodiments E190-E196, wherein the nucleo-functional polymer is a biocompatible poly(vinyl alcohol) polymer comprising:

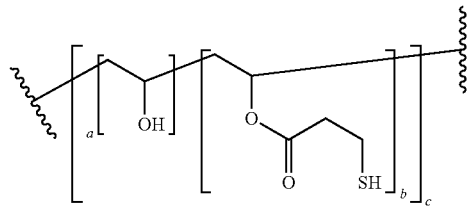

wherein a is an integer from 1 to about 20, b is an integer from 1 to about 20, and c is an integer from about 20 to about 500. E205. The method of any one of embodiments E190-E204, wherein the nucleo-functional polymer has a weight-average molecular weight in the range of from about 4,000 g/mol to about 100,000 g/mol. E206. The method of any one of embodiments E190-E205, wherein the nucleo-functional polymer has a weight-average molecular weight in the range of from about 15,000 g/mol to about 25,000 g/mol. E207. The method of any one of embodiments E190-E206, wherein the nucleo-functional polymer has a weight-average molecular weight of less than about 75,000 g/mol. E208. The method of any one of embodiments E190-E207, wherein the electro-functional polymer is a biocompatible polymer comprising poly(ethylene glycol). E209. The method of any one of embodiments E190-E208, wherein the electro-functional polymer is a biocompatible polymer comprising poly(ethylene glycol)polymer substituted by at least one thiol-reactive group. E210. The method of any one of embodiments E190-E209, wherein the thiol-reactive group is an alpha-beta unsaturated ester, maleimidyl, sulfone, or combinations thereof. E211. The method of embodiment 210, wherein the alpha-beta unsaturated ester, maleimidyl, or sulfone is optionally substituted by one or more occurrences of alkyl, aryl, or aralkyl. E212. The method of any one of embodiments E190-E211, wherein the thiol-reactive group is acrylate, maleimide, or vinylsulfone. E213. The method of any one of embodiments E190-E212, wherein the electro-functional polymer has a weight-average molecular weight in the range of from about 500 g/mol to about 100,000 g/mol. E214. The method of any one of embodiments E190-E213, wherein the electro-functional polymer has a weight-average molecular weight in the range of from about 1,000 g/mol to about 50,000 g/mol. E215. The method of any one of embodiments E190-E214, wherein the electro-functional polymer has a weight-average molecular weight in the range of from about 2,000 g/mol to about 20,000 g/mol. E216. The method of any one of embodiments E190-E215, wherein the electro-functional polymer has a weight-average molecular weight in the range of from about 2,700 g/mol to about 3,000 g/mol. E217. The method of any one of embodiments E190-E216, wherein the electro-functional polymer has a weight-average molecular weight in the range of from about 9,000 g/mol to about 11,000 g/mol. E218. The method of any one of embodiments E190-E217, wherein the electro-functional polymer has a weight-average molecular weight in the range of from about 18,000 g/mol to about 22,000 g/mol. E219. The method of any one of embodiments E190-E218, wherein the electro-functional polymer comprises a multi-arm polymer. E220. The method of embodiment 219, wherein the multi-arm polymer comprises as 4-arm polyethylene glycol maleimide, 4-arm polyethylene glycol acrylate, 4-arm polyethylene glycol vinyl sulfone, 8-arm polyethylene glycol maleimide, 8-arm polyethylene glycol acrylate, 8-arm polyethylene glycol vinyl sulfone, or combinations thereof. E221. The method of any one of embodiments E190-E220, wherein the mole ratio of (i) thio-functional groups —$R^1$—SH to (ii) thiol-reactive group is in the range of about 10:1 to about 1:10. E222. The method of any one of embodiments E190-E221, wherein the mole ratio of (i) thio-functional groups —$R^1$—SH to (ii) thiol-reactive groups is in the range of about 2:1 to about 1:2. E223. The method of any one of embodiments E190-E222, wherein the mole ratio of (i) thio-functional groups —$R^1$—SH to (ii) thiol-reactive groups is in the range of about 0.8:1 to about 1.2:1. E224. The method of any one of embodiments E191-E223, wherein the formulation comprises water, and the formulation has a pH in the range of about 7.1 to about 7.7. E225. The method of any one of embodiments E191-E224, wherein the formulation comprises water, and the formulation has a pH in the range of about 7.3 to about 7.5. E226. The method of any one of embodiments E191-E225, wherein the formulation comprises water, and the formulation has a pH of about 7.4. E227. The method of any one of embodiments E191-E226, where the formulation further comprises an alkali metal salt. E228. The method of any one of embodiments E191-E227, wherein the formulation further comprises an alkali metal halide salt, an alkaline earth metal halide salt, or a combination thereof. E229. The method of any one of embodiments E191-E228, wherein the formulation further comprises sodium chloride, potassium chloride, calcium chloride, magnesium chloride, or a combination thereof. E230. The method of any one of embodiments E191-E229, wherein the formulation has an osmolality in the range of about 200 mOsm/kg to about 400 mOsm/kg. E231. The method of any one of embodiments E191-E230, wherein the formulation has an osmolality in the range of about 250 mOsm/kg to about 350 mOsm/kg. E232. The method of any one of embodiments E191-E231, wherein the formulation has an osmolality in the range of about 280 mOsm/kg to about 320 mOsm/kg. E233. The method of any one of embodiments E191-E232, wherein the formulation has an osmolality of about 300 mOsm/kg. E234. The method of any one of embodiments E191-E233, wherein the formulation has an endotoxin level of less than about 20 endotoxin units/ml, less than about 15 endotoxin units/ml, less than about 10 endotoxin units/ml, less than about 5 endotoxin units/ml, less than about 2.5 endotoxin units/ml, less than about 1.0 endotoxin units/ml, less than about 0.8 endotoxin units/ml, less than about 0.5 endotoxin units/ml, less than about 0.2 endotoxin units/ml, or less than about 0.1 endotoxin units/ml. E235. The method of any one of embodiments E191-E234, wherein the formulation has less than about 50 particles per mL with a size of ≥10 μm. E236. The method of any one of embodiments E191-E235, wherein the formulation has less than about 5 particles per mL with a size of ≥25 μm. E237. The method of any one of embodiments E191-E236, wherein the extended-release hydrogel has a transparency of at least about 80% for light in the visible spectrum when measured through a hydrogel having a thickness of 2 cm. E238. The method of any one of embodiments E190-E237, wherein the extended-release hydrogel has a transparency of at least about 85% for light in the visible spectrum when measured through a hydrogel having a thickness of 2 cm. E239. The method of any one of embodiments E190-E238, wherein the extended-release hydrogel has a transparency or at least about 90% for light in the visible spectrum when measured through a hydrogel having a thickness of 2 cm. E240. The method of any one of embodiments E191-E239, wherein the extended-release hydrogel has a crosslink time of less than about 10 minutes, less than about 7 minutes, less than about 5 minutes, less than about 3 minutes, less than about 1 minute, less than about 20 seconds, less than about 10 seconds, less than about 5 seconds, or less than about 1 second when measured at 37° C. E241. The method of any one of embodiments E190-E240, wherein the extended-release hydrogel has a degradation time that is greater than or equal to about 3, about 5, about 8, about 10, about 13, about 14, about 15, about 19, or about 32 days at 60° C. E242. The method of any one of embodiments E190-E241, wherein the extended-release hydrogel has a degradation time that is greater than or equal to about 20, about 40, about 60, about 69, about 80, about 94, about 100, or about 158 days at 37° C. E243. The method of any one of embodiments E190-E242, wherein the extended-release hydrogel acts as a depot for the pharmaceutical agent. E244. The method of any one of embodiments E190-E243, wherein the extended-release hydrogel provides for extended-release of the pharmaceutical agent. E245. The method of any one of embodiments E190-E244, wherein the extended-release hydrogel releases the pharmaceutical agent over a period of at least about 5, about 10, about 20, about 30, about 40, about 50, about 60, about 70, about 80, about 90, about 100, or about 120 days. E246. The method of any one of embodiments E190-E245, wherein complete release of the pharmaceutical agent from the extended-release hydrogel is achieved after at least about 10, about 20, about 30, about 40, about 50, about 60, about 70, about 80, about 90, about 100, about 110, about 120, about 130 days. E247. The method of any one of embodiments E190-E246, where the extended-release hydrogel comprises a nearly first-order release of the pharmaceutical agent. E248. The method of any one of embodiments E190-E247, wherein the formulation has a viscosity of less than about 4000 cP, about 2000 cP, about 1000 cP, about 800 cP, about 600 cP, about 500 cP, about 400 cP, about 200 cP, about 100 cP, about 80 cP, about 60 cP, about 50 cP, about 40 cP, about 20 cP, about 10 cP, about 8 cP, about 6 cP, about 5 cP, about 4 cP, about 3 cP, about 2 cP about 1 cP prior to formation of the hydrogel. E249. The method of any one of embodiments E190-E248, wherein the pharmaceutical agent comprises an anti-inflammatory agent, a steroid, an NSAID, an intraocular pressure lowering drug, an antibiotic, a pain reliever, an inhibitor of vascular endothelial growth factor (VEGF), an inhibitor of abnormal vascular growth or vascular leakage, an inhibitor of abnormal cell proliferation, a chemotherapeutic, an anti-viral drug, a gene therapy viral vector, or a combination thereof. E250. The method of any one of embodiments E190-E249, wherein the pharmaceutical agent comprises a small molecule, a protein, a DNA or RNA fragment, a glycosaminoglycan, a carbohydrate, a nucleic acid, an inorganic and organic biologically active compound, an active portion of any of the proceeding, or a combination thereof. E251. The method of any one of embodiments E190-E250, wherein the pharmaceutical agent comprises an antibody, a bi-specific antibody, a single-chain variable fragment (scFv), an active portion of any of the proceeding, or a combination thereof. E252. The method of any one of embodiments E190-E251, wherein the pharmaceutical agent comprises an anti-cancer agent. E253. The method of any one of embodiments E190-E252, wherein the pharmaceutical agent comprises bevacizumab. E254. The method of any one of embodiments E190-E253, wherein the pharmaceutically acceptable carrier comprises water. E255. The method of any one of embodiments E190-E254, wherein the pharmaceutically acceptable carrier comprises PBS. E256. The method of embodiment 255, wherein the PBS comprises one or more of sodium chloride, potassium chloride, sodium phosphate and potassium phosphate. E257. The method of any one of embodiments E191-E256, wherein the formulation is an ocular formulation. E258. The method of any one of embodiments E190-E257, wherein the nucleo-functional polymer, the electro-functional polymer, the pharmaceutical agent, and the pharmaceutically acceptable carrier are administered to the eye of a subject. E259. The method of embodiment 258, wherein the nucleo-functional polymer, the electro-functional polymer, the pharmaceutical agent, and the pharmaceutically acceptable carrier are administered to the vitreous cavity. E260. The method of embodiment 259, wherein the vitreous cavity comprises vitreous. E261. The method of any one of embodiments E258-E260, wherein the nucleo-functional polymer, the electro-functional polymer, the pharmaceutical agent, and the pharmaceutically acceptable carrier are administered as an intravitreal injection. E261. The method of any one of embodiments E258-E261, wherein the subject has not undergone a vitrectomy. E262. The method of any one of embodiments E258-E261, wherein the subject has undergone a partial or complete vitrectomy. E263. The method of any one of embodiments E190-E263, wherein the subject suffers from age-related macular degeneration (AMD), proliferative diabetic retinopathy, proliferative vitreoretinopathy, ocular malignancies, inherited retinal diseases, diabetic macular edema, macular edema from retinal vein occlusions, choroidal neovascularization, uveitis, or a combination thereof.

E265. An injectable, ocular formulation for forming a hydrogel in an eye of a subject, the formulation comprising: a. a nucleo-functional polymer that is a biocompatible polymer comprising poly(vinyl alcohol) containing a plurality of thio-functional groups —R1-SH, wherein $R^1$ is an ester-containing linker; b. an electro-functional polymer that is a biocompatible polymer comprising poly(ethylene glycol) containing at least one thiol-reactive group; and c. a liquid pharmaceutically acceptable carrier comprising 5×phosphate buffered saline (PBS) that is suitable for administration of the ocular formulation to the eye of the subject; wherein the ocular formulation has an osmolality in the range of about 280 mOsm/kg to about 320 mOsm/kg and the formulation forms a hydrogel in the eye of the subject. E266. The formulation of embodiment E265, wherein a first solution comprising the nucleo-functional polymer and a second solution comprising the electro-functional polymer are mixed to form the formulation. E267. The formulation of embodiment E265 or embodiment E266, wherein the 5×PBS comprises about 50 mM to about 90 mM sodium chloride, about 2.5 mM to about 3 mM potassium, about 50 mM sodium phosphate, about 9 nM potassium phosphate, or combinations thereof. E268. The formulation of any one of embodiments E265-E267, wherein the formulation has an osmolality in the range of about 280 mOsm/kg to about 300 mOsm/kg. E269. The formulation of any one of embodiments E265-E268, wherein the formulation has an osmolality in the range of about 300 mOsm/kg to about 320 mOsm/kg. E270. The formulation of any one of embodiments E265-E269, wherein the formulation has a pH in the range of about 7.1 to about 7.7. E271. The formulation of anyone of embodiments E265-E270, wherein the formulation has a pH in the range of about 7.3 to about 7.5. E272. The formulation of any one of embodiments E266-E271, wherein the formulation has a viscosity of between about 550 cP and about 1350 cP at around 12-13 minutes after mixing the first and second solutions to form the formulation, or after about 30 seconds to about 120 seconds after mixing when heat is applied to the formulation. E273. The formulation of any one of claims 266-E272, wherein the formulation has a viscosity of between about 8900 cP and about 11,600 cP at around 17-18 minutes after mixing the first and second solutions to form the formulation, or after about 30 seconds to about 120 seconds after mixing when heat is applied to the formulation. E274. The formulation of any one of embodiments E266-E273, wherein the formulation has an initial, low viscosity after mixing the first and second solutions to form the formulation such that the formulation can be administered through a needle having a gauge of less than or equal to 23 using a force of no more than 5N. E275. The formulation of any one of embodiments E265-E274, wherein the formulation is formed following separate injection of the nucleo-functional polymer and the electro-functional polymer into the vitreous cavity of the eye of the subject. E276. The formulation of any one of embodiments E265-E275, wherein the nucleo-functional polymer, the electro-functional polymer, or both, are reconstituted in 5×PBS. E277. The formulation of embodiment E276, wherein the reconstituted nucleo-functional polymer, the reconstituted electro-functional polymer, or both, has a pH between about 7.1 to about 7.7. E278. The formulation of embodiment E276 or embodiment E277, wherein the reconstituted nucleo-functional polymer, the reconstituted electro-functional polymer, or both, has a pH between about 7.3 to about 7.5. E279. The formulation of any one of embodiments E276-E278, wherein the nucleo-functional polymer, the electro-functional polymer, or both, are reconstituted after having been stored for at least 1 week, at least 1 month, at least 2 months, at least 6 months, at least 12 months, at least 15 months, at least 18 months, at least 20 months, or at least 24 months. E280. The formulation of any one of embodiments E265-E279, wherein the nucleo-functional polymer has a weight-average molecular weight in the range of from about 500 g/mol to about 1,000,000 g/mol and the electro-functional polymer has a weight-average molecular weight in the range of from about 500 g/mol to about 1,000,000 g/mol. E281. The formulation of any one of embodiments E265-E280, wherein the mole ratio of the plurality of thio-functional groups-R1—SH to the at least one thiol-reactive group is in the range of 10:1 to 1:10, 5:1 to 1:1, or 2:1 to 1:1. E282. The formulation of any one of embodiments E265-281, wherein $R^1$—SH is —OC(O)—($C_1$-$C_6$ alkylene)-SH. E283. The formulation of any one of embodiments E265-E282, wherein the poly(ethylene glycol) is linear, branched, a dendrimer, or multi-armed. E284. The formulation of any one of embodiments E265-E283, wherein the hydrogel formed in the eye of the subject has a refractive index in the range of from about 1.2 to about 1.5. E285. The formulation of any one of embodiments E265-E284, wherein the hydrogel formed in the eye of the subject has a transparency of at least 90% for light in the visible spectrum when measured through the hydrogel having a thickness of 2 cm. E286. The formulation of any one of embodiments E265-E285, wherein the hydrogel formed in the eye of the subject has a gelation time of less than about 10 minutes. E287. The formulation of any one of embodiments E265-E286, wherein the hydrogel formed in the eye of the subject undergoes complete biodegradation from the eye of the subject within about 3 days to about 7 days, about 2 weeks to about 8 weeks, about 4 months to about 6 months, or within 12 months or 24 months. E288. The formulation of any one of embodiments E265-E287, wherein the hydrogel formed in the eye of the subject has a biodegradation half-life in the range of from about 1 week to about 3 weeks or from about 8 weeks to about 15 weeks when disposed within the vitreous cavity of an eye. E289. The formulation of any one of embodiments E265-E288, wherein the hydrogel formed in the eye of the subject results in a pressure within the eye of less than about 30 mmHg. E290. The formulation of any one of embodiments E265-E289, wherein the hydrogel formed in the eye of the subject results in a pressure within the eye of less than about 25 mmHg.

E291. A device for warming and mixing a solution, the device comprising: a. a heating chamber comprising an at least partially closed volume; b. a holding mechanism within the heating chamber that is configured to reversibly hold and secure a vial that is configured to hold a solution; c. a platform within the heating chamber that is capable of rotating and to which the holding mechanism is attached; d. a heater within the heating chamber; e. a fan within the heating chamber; f. one or more thermocouples within the heating chamber that is configured to measure a temperature within the heating chamber and/or monitors a temperature of the solution within the vial when the vial is present in the holding mechanism; and g. a display within the heating chamber; wherein the device is configured to heat the solution within the vial to a specified temperature over a specified time while continuously shaking the vial solution to provide mixing of and even distribution of temperature within the solution. E292. The device of embodiment 291, wherein the heating chamber further comprises a door. 293. The device of embodiment E291 or embodiment E292, wherein the heater is configured to automatically shut off when a desired temperature of the solution is reached. E294. The device of any one of embodiments E291-E293, wherein the display is configured to receive inputs from a user that control the function of the platform, the heater, the fan, and/or the one or more thermocouples. E295. The device of any one of embodiments E291-E294, wherein the display is configured to provide information on the status of a warming cycle, inform a user when warming cycle is completed, and/or inform a user when the vial is ready to be removed from the heating chamber.

E296. A method of providing a retinal tamponade in an eye of a subject, the method comprising: a. mixing a first solution comprising a nucleo-functional polymer and a second solution comprising an electro-functional polymer to form a hydrogel-forming formulation having an initial viscosity of less than about 550 cP; b. allowing the hydrogel-forming formulation to reach a viscosity of at least about 550 cP; c. applying the hydrogel-forming formulation having the viscosity of at least about 550 cP to a surface of the retina; wherein the hydrogel-forming formulation forms a hydrogel on the surface of the retina. E297. The method of embodiment 296, wherein the nucleo-functional polymer is a biocompatible polymer comprising poly(vinyl alcohol) containing a plurality of thio-functional groups —$R^1$—SH, wherein $R^1$ is an ester-containing linker, and the electro-functional polymer is a biocompatible polymer comprising poly(ethylene glycol) containing at least one thiol-reactive group. E298. The method of embodiment E296 or embodiment E297, wherein the hydrogel-forming formulation has a viscosity of between about 550 cP and about 1350 cP at around 12-13 minutes after mixing the first and second solutions to form the hydrogel-forming formulation, or after about 30 seconds to about 120 seconds after mixing when heat is applied to the hydrogel-forming formulation. E299. The method of any one of embodiments E296-E298, wherein the hydrogel-forming formulation has a viscosity of between about 8900 cP and about 11,600 cP at around 17-18 minutes after mixing the first and second solutions to form the hydrogel-forming formulation, or after about 30 seconds to about 120 seconds after mixing when heat is applied to the hydrogel-forming formulation. E300. The method of any one of embodiments E296-E299, wherein the hydrogel-forming formulation further comprises a liquid pharmaceutically acceptable carrier comprising 5×phosphate buffered saline (PBS) that is suitable for administration of the ocular formulation to the eye of the subject. E301. The method of embodiment E300, wherein the 5×PBS comprises about 50 mM to about 90 mM sodium chloride, about 2.5 mM to about 3 mM potassium, about 50 mM sodium phosphate, about 9 nM potassium phosphate, or combinations thereof. E302. The method of any one of embodiments E296-E301, wherein the hydrogel-forming formulation has an osmolality in the range of about 280 mOsm/kg to about 300 mOsm/kg. E303. The method of any one of embodiments E296-E302, wherein the hydrogel-forming formulation has an osmolality in the range of about 300 mOsm/kg to about 320 mOsm/kg. E304. The method of any one of embodiments E296-E303, wherein the hydrogel-forming formulation has a pH in the range of about 7.1 to about 7.7. E305. The method of anyone of embodiments E296-E304, wherein the hydrogel-forming formulation has a pH in the range of about 7.3 to about 7.5. E306. The method of any one of embodiments E296-E305, wherein the first solution comprising a nucleo-functional polymer is formed by reconstituting the nucleo-functional polymer after the nucleo-functional polymer has been stored for at least 1 week, at least 1 month, at least 2 months, at least 6 months, at least 12 months, at least 15 months, at least 18 months, at least 20 months, or at least 24 months. E307. The method of any one of embodiments E296-E306, wherein the second solution comprising an electro-functional polymer is formed by reconstituting the electro-functional polymer after the electro-functional polymer has been stored for at least 1 week, at least 1 month, at least 2 months, at least 6 months, at least 12 months, at least 15 months, at least 18 months, at least 20 months, or at least 24 months. E308. The method of any one of embodiments E296-E307, wherein the nucleo-functional polymer has a weight-average molecular weight in the range of from about 500 g/mol to about 1,000,000 g/mol and the electro-functional polymer has a weight-average molecular weight in the range of from about 500 g/mol to about 1,000,000 g/mol. E309. The method of any one of E296-E308, wherein the mole ratio of the plurality of thio-functional groups-$R^1$—SH to the at least one thiol-reactive group is in the range of 10:1 to 1:10, 5:1 to 1:1, or 2:1 to 1:1. E310. The method of any of embodiments E296-E309, wherein $R^1$—SH is —OC(O)—($C_1$-$C_6$ alkylene)-SH. E311. The method of any one of embodiments E296-E310, wherein the poly(ethylene glycol) is linear, branched, a dendrimer, or multi-armed. E312. The method of any one of embodiments E296-E311, wherein the hydrogel formed in the eye of the subject has a refractive index in the range of from about 1.2 to about 1.5. E313. The method of any one of embodiments E296-E312, wherein the hydrogel has a transparency of at least 90% for light in the visible spectrum when measured through the hydrogel having a thickness of 2 cm. E314. The method of any one of embodiments E296-E313, wherein the hydrogel has a gelation time of less than about 10 minutes. E315. The method of any one of embodiments E296-E314, wherein the hydrogel undergoes complete biodegradation from the eye of the subject within about 3 days to about 7 days, about 2 weeks to about 8 weeks, about 4 months to about 6 months, or within 12 months or 24 months. E316. The method of any one of embodiments E296-E315, wherein the hydrogel has a biodegradation half-life in the range of from about 1 week to about 3 weeks or from about 8 weeks to about 15 weeks when disposed within the vitreous cavity of an eye. E317. The method of any one of embodiments E296-E316, wherein the hydrogel results in a pressure within the eye of less than about 30 mmHg. E318. The method of any one of embodiments E296-E317, wherein the hydrogel results in a pressure within the eye of less than about 25 mmHg.

Various aspects and embodiments of the invention are described in further detail below, along with further description of multiple advantages provided by the invention.

DETAILED DESCRIPTION OF THE INVENTION

Figure 1:
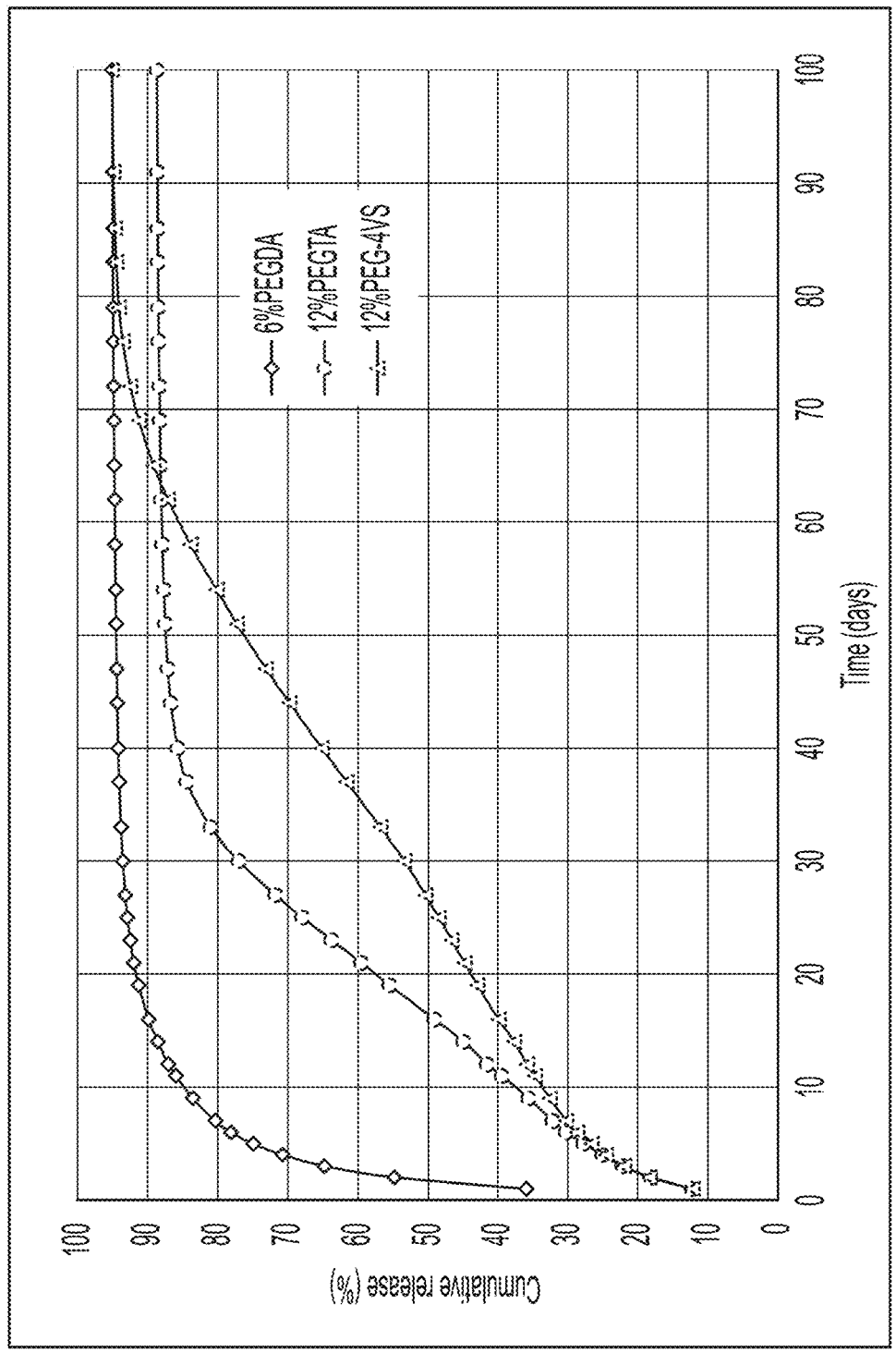
FIG. 1 shows the release of FITC-Dextran over time from exemplary extended-release hydrogels described herein.

Various aspects of the invention are set forth below in sections; however, aspects of the invention described in one particular section are not to be limited to any particular section and are applicable to other sections as appropriate and as would be understood by those of ordinary skill in the art.

Definitions

To facilitate an understanding of the present invention, a number of terms and phrases are defined below.

The terms "a" and "an" as used herein mean "one or more" and include the plural unless the context is inappropriate.

The term "about," when used to modify a numerical value herein, mean±10% of that numerical value. For example, "about 100" refers to any number between, and including, 90 to 110.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. In certain embodiments, the aromatic ring is substituted at one or more ring positions with halogen, alkyl, hydroxyl, or alkoxyl. In certain other embodiments, the aromatic ring is not substituted, i.e., it is unsubstituted.

The term "aralkyl" refers to an alkyl group substituted with an aryl group.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted.

The term "heteroaralkyl" refers to an alkyl group substituted with a heteroaryl group.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a $C_3$heterocyclyl is aziridinyl. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclcyl group is not substituted, i.e., it is unsubstituted.

The terms "amine" and "amino" are art-recognized and refer to both unsubstituted and substituted amines, e.g., a moiety represented by the general formula —N($R^{50}$)($R^{51}$), wherein $R^{50}$ and $R^{51}$ each independently represent hydrogen, alkyl, cycloalkyl, heterocyclyl, alkenyl, aryl, aralkyl, or —(CH$_2$)$_m$—$R^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—$R_{61}$, where m and $R_{61}$ are described above.

The term "amide" or "amido" as used herein refers to a radical of the form —$R_a$C(O)N($R_b$)—, —$R_a$C(O)N($R_b$)$R_c$—, —C(O)N$R_b$$R_c$, or —C(O)NH$_2$, wherein $R_a$, $R_b$ and $R_c$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, $R_b$, Re, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(+)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

As used herein, the terms "subject" and "patient" refer to organisms to be treated by the methods of the present invention. In certain embodiments, such organisms are mammals (e.g., murines, simians, equines, bovines, porcines, canines, felines, and the like), and in some embodiments, such organisms are humans.

As used herein, the term "effective amount" refers to the amount of a compound, composition, or formulation (e.g., a compound, composition, or formulation of the present invention) sufficient to effect beneficial or desired results. As used herein, the term "treating" includes any effect, e.g., lessening, reducing, modulating, ameliorating or eliminating, that results in the improvement of the condition, disease, disorder, and the like, or ameliorating a symptom thereof.

As used herein, the terms "pharmaceutical agent," "pharmaceutically active agent," and "drug" are used synonymously and refer to an active agent, making the composition or formulation especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. In certain embodiments, the pharmaceutically acceptable carrier is, or comprises, balanced salt solution. The compositions or formulations also can include stabilizers and preservatives. For examples of carriers, stabilizers and adjuvants/excipients, see, e.g., Martin, Remington's Pharmaceutical Sciences, 15th Ed., Mack Publ. Co., Easton, PA [1975], the disclosure of which is incorporated by reference herein in its entirety. The compositions or formulations may optionally contain a dye. Accordingly, in certain embodiments, the composition or formulation further comprises a dye.

Throughout the description, the molecular weight of a polymer is weight-average molecular weight unless the context clearly indicates otherwise, such as clearly indicating that the molecular weight of the polymer is the number-average molecular weight.

Throughout the description, where compositions or formulations and kits are described as having, including, or comprising specific components, or where processes and methods are described as having, including, or comprising specific steps, it is contemplated that, additionally, there are compositions or formulations and kits of the present invention that consist essentially of, or consist of, the recited components, and that there are processes and methods according to the present invention that consist essentially of, or consist of, the recited processing steps.

As a general matter, compositions or formulations specifying a percentage are by weight unless otherwise specified. Further, if a variable is not accompanied by a definition, then the previous definition of the variable controls.

Formulations for Forming Extended-Release Hydrogels Comprising a Pharmaceutically Active Agent One aspect of the invention provides an injectable formulation for forming an extended-release hydrogel and delivering a pharmaceutical agent over an extended period of time at the site of interest of a subject, the formulation comprising: (a) a nucleo-functional polymer that is a biocompatible polymer containing a plurality of thio-functional groups —$R^1$—SH wherein $R^1$ is an ester-containing linker; (b) an electro-functional polymer that is a biocompatible polymer containing at least one thiol-reactive group; (c) a pharmaceutical agent; and (d) a liquid pharmaceutically acceptable carrier for administration to the eye of a subject. The formulation can be further characterized by, for example, the identity and structure of the nucleo-functional polymer, the identity and structure of the electro-functional polymer, the identity of the pharmaceutical agent, physical characteristics of the hydrogel formed for controlling the delivery of the pharmaceutical agent, and other features described herein below. In certain embodiments, the site of interest of the subject is the eye and the formulation is an ocular formulation.

The extended-release hydrogel is formed by reaction of the nucleo-functional polymer and electro-functional polymer, and the subsequent uptake of water from the subject (e.g., the subject's eye or other tissue of interest). In the more specific embodiment of a thiolated poly(vinyl alcohol) polymer as the nucleo-functional polymer and a poly(ethylene glycol) (PEG) containing thiol-reactive groups as the electro-functional polymer, the hydrogel is formed by a cross-linking reaction of thiolated poly(vinyl alcohol) (TPVA) with poly(ethylene glycol) (PEG) containing thiol-reactive groups. The thiolated poly(vinyl alcohol) polymer can be prepared whereby thiol groups are incorporated into poly(vinyl alcohol) (PVA) by coupling thiol functionalities to the hydroxyl groups of the poly(vinyl alcohol), or through use of protected thiol functionalities with subsequent deprotection as described in the literature. Certain poly(ethylene glycol) polymers containing thiol-reactive groups (e.g., an acrylate, methacrylate, maleimidyl, or vinyl-sulfone) may be used in accordance with the invention. Crosslinking of the thiolated poly(vinyl alcohol) and the poly(ethylene glycol) containing thiol-reactive groups occurs through a Michael addition, without use of initiators or an external energy source (e.g., UV light).

Features of the Nucleo-Functional Polymer

The compositions or formulations for forming an extended-release hydrogel for extended-release of a drug for treatment of various disorders, including ocular disorders, can be characterized according to features of the nucleo-functional polymer. Accordingly, in certain embodiments, the nucleo-functional polymer is a biocompatible polymer comprising poly(vinyl alcohol) containing a plurality of thio-functional groups —$R^1$—SH where, $R^1$ is an ester-containing linker. In certain embodiments, the nucleo-functional polymer is a biocompatible, partially hydrolyzed poly(vinyl alcohol) polymer substituted by a plurality of thio-functional groups —$R^1$—SH. In certain embodiments, the nucleo-functional polymer is a biocompatible, partially hydrolyzed poly(vinyl alcohol) polymer substituted by a plurality of thio-functional groups —$R^1$—SH, wherein the degree of hydrolysis of the partially hydrolyzed poly(vinyl alcohol) polymer is at least 85%. In certain embodiments, the thio-functional group —$R^1$—SH is —OC(O)—($C_1$-$C_6$ alkylene)-SH. In certain embodiments, the thio-functional group —$R^1$—SH is —OC(O)—($CH_2CH_2$)—SH.

In certain embodiments, the nucleo-functional polymer is a biocompatible poly(vinyl alcohol) polymer comprising:

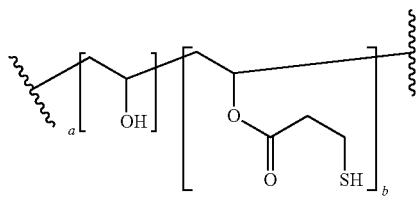

wherein a is an integer from 1 to about 20 and b is an integer from 1 to about 20.

In certain embodiments, the nucleo-functional polymer is a biocompatible poly(vinyl alcohol) polymer comprising:

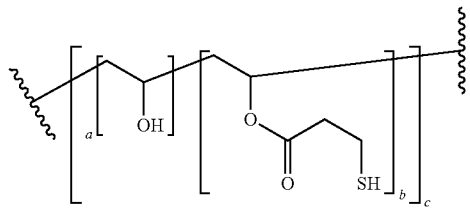

wherein a is an integer from 1 to about 20, b is an integer from 1 to about 20, and c is an integer from about 20 to about 500.

The nucleo-functional polymer may be further characterized according to its molecular weight, such as the weight-average molecular weight of the polymer. In certain embodiments, the nucleo-functional polymer has a weight-average molecular weight in the range of from about 4,000 g/mol to about 100,000 g/mol. In certain embodiments, the nucleo-functional polymer has a weight-average molecular weight less than about 75,000 g/mol. In certain embodiments, the nucleo-functional polymer has a weight-average molecular weight in the range of from about 15,000 g/mol to about 25,000 g/mol. In certain embodiments, the nucleo-functional polymer has a weight-average molecular weight of about 19,000 g/mol.

In certain embodiments, the nucleo-functional polymer is a thiolated poly(vinyl alcohol) that has been at least partially hydrolyzed (e.g., hydrolysis of about 75% or more, including all values and ranges from about 75% to about 99.9%). The thiolated poly(vinyl alcohol) may be provided in a solution, dissolved in water or other solvents (including, but not limited to, dimethyl sulfoxide (DMSO) or dimethylformamide (DMF)) at any viable concentration, including at a concentration in the range of about 0.5 wt % to about 25 wt %, including all values and increments therein.

The thiolated poly(vinyl alcohol) can be prepared by reacting a range of thiol containing functional groups with poly(vinyl alcohol), for example, as further described in U.S. Patent Application Publication No. 2016/0009872, which is hereby incorporated by reference herein in its entirety. In certain embodiments, thiolated poly(vinyl alcohol) is prepared by reacting (a) a compound having a thiol functionality and at least one hydroxyl-reactive group, such as, for example, a carboxyl group, represented by HS—R—CO$_2$H, where R may include an alkane, unsaturated ether, or ester group, and R includes from 1 to about 20 carbons, with (b) a poly(vinyl alcohol).

In other more specific embodiments, the thiolated poly (vinyl alcohol) comprises the following fragment:

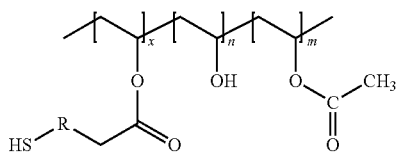

wherein R includes from 1 to about 20 carbons and may be an alkane, saturated ether or ester, and the individual units are randomly distributed along the length of the poly(vinyl alcohol) chain. X is in the range of about 0.1 to about 10%, n is in the range of about 80 to about 99.9%, indicating the level of hydrolysis of the poly(vinyl alcohol) polymer and allowing for water solubility of the polymer and m, the amount of non-hydrolyzed acetate groups, is in the range from about 0.1 to about 20%.

The amount of thiol groups on the poly(vinyl alcohol) can be controlled by the number of hydroxyl groups on the poly(vinyl alcohol) that undergo reaction with the thiolating agent to generate the thiolated poly(vinyl alcohol). In certain embodiments, the amount of thiol functional groups on the poly(vinyl alcohol) may be characterized according to the molar ratio of thiol functional groups to poly(vinyl alcohol) polymer, such as from about 0.1:1 to about 10.0:1, including all values and ranges therein. In certain embodiments, the amount of thiol functional groups is from about 5.0:1 to about 7.0:1, including all values and ranges therein.

More generally, the nucleo-functional polymer containing a plurality of thio-functional groups can be prepared based on procedures described in the literature, such as U.S. Patent Application 2016/0009872, which is hereby incorporated by reference in its entirety, in which a polymer having nucleophilic groups (e.g., hydroxyl groups) is reacted with a thiol-containing compound so that resulting polymer contains a thiol group bound to the polymer backbone via a linker.

Features of the Electro-Functional Polymer

The compositions or formulations for forming an extended-release hydrogel for extended-release of a drug for treatment of various disorders, including ocular disorders, can be characterized according to the features of the electro-functional polymer. Accordingly, in certain embodiments, the electro-functional polymer is a biocompatible poly(ethylene glycol) polymer substituted by at least one thiol-reactive group.

In certain embodiments, the thiol-reactive group is an alpha-beta unsaturated ester, maleimidyl, or sulfone, each of which is optionally substituted by one or more occurrences of alkyl, aryl, or aralkyl. In certain embodiments, the thiol-reactive group is an alpha-beta unsaturated ester optionally substituted by one or more occurrences of alkyl, aryl, or aralkyl. In certain embodiments, the thiol-reactive group is acrylate

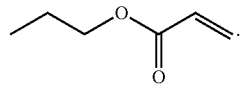

In certain embodiments, the thiol-reactive group is maleimide

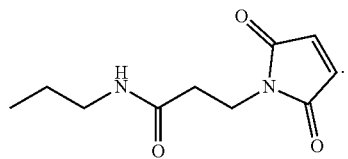

In certain embodiments, the the thiol-reactive group is vinyl sulfone

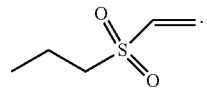

The electro-functional polymer may be further characterized according to its molecular weight, such as the weight-average molecular weight of the polymer. Accordingly, in certain embodiments, the electro-functional polymer has a weight-average molecular weight in the range of from about 500 g/mol to about 100,000 g/mol. In certain embodiments, the electro-functional polymer has a weight-average molecular weight in the range of from about 1,000 g/mol to about 50,000 g/mol. In certain embodiments, the electro-functional polymer has a weight-average molecular weight in the range of from about 2,000 g/mol to about 20,000 g/mol. In certain embodiments, the electro-functional polymer has a weight-average molecular weight less than about 100,000 g/mol. In certain embodiments, the electro-functional polymer has a weight-average molecular weight in the range of from about 2,700 g/mol to about 3,300 g/mol. In certain embodiments, the electro-functional polymer has a weight-average molecular weight in the range of from about 9,000 g/mol to about 11,000 g/mol. In certain embodiments, the electro-functional polymer has a weight-average molecular weight in the range of from about 18,000 g/mol to about 22,000 g/mol.

The electro-functional polymer may be a straight-chain polymer or a branched chain polymer. In yet other embodiments, the electro-functional polymer may be a multi-arm polymer, such as 4-arm polyethylene glycol maleimide, 4-arm polyethylene glycol acrylate, 4-arm polyethylene glycol vinyl sulfone, 8-arm polyethylene glycol maleimide, 8-arm polyethylene glycol acrylate, or 8-arm polyethylene glycol vinyl sulfone or combinations thereof.

In another embodiment, the electro-functional polymer may be a poly(ethylene glycol) end-capped with at least two thiol-reactive groups. The poly(ethylene glycol) may be linear, branched, a dendrimer, or multi-armed. The thiol reactive group may be, for example, an acrylate, methacrylate, maleimidyl, vinyl sulfone, haloacetyl, pyridyldithiol, N-hydroxysuccinimidyl. An exemplary poly(ethylene glycol) end-capped with thiol-reactive groups may be represented by the formula Y—[—O—$CH_2CH_2$-]$_n$—O—Y wherein each Y is a thiol-reactive group, and n is, for example, in the range of about 200 to about 20,000. In another embodiment, the electro-functional polymer may be $CH_2$=CHC(O)O—[—$CH_2CH_2$—O-]b-C(O)CH=$CH_2$, wherein b is, for example, in the range of about 200 to about 20,000. Alternatively or additionally to the linear embodiments depicted above, the poly(ethylene glycol) may be a dendrimer. For example, the poly(ethylene glycol) may be a 4 to 32 hydroxyl dendron. In further embodiments, the poly(ethylene glycol) may be multi-armed. In such embodiments, the poly(ethylene glycol) may be, for example, 4, 6 or 8 arm and hydroxy-terminated. The molecular weight of the poly(ethylene glycol) may be varied, and in some cases one of the thiol-reactive groups may be replaced with other structures to form dangling chains, rather than crosslinks. In certain embodiments, the molecular weight (Mw) is less than about 25,000, including all values and ranges from about 200 to about 20,000, such as about 200 to about 1,000, about 1,000 to about 10,000, etc. In addition, the degree of functionality may be varied, meaning that the poly(ethylene glycol) may be mono-functional, di-functional or multi-functional.

More generally, the electro-functional polymer can be purchased from commercial sources or prepared based on procedures described in the literature, such as by treating a nucleo-functional polymer with reagent(s) to install one or more electrophilic groups (e.g., by reacting polyethylene glycol with acrylic acid in an esterification reaction to form polyethylene glycol diacrylate, using procedures described in U.S. Pat. No. 6,828,401, which is incorporated by reference herein in its entirety, to form polyethylene glycol-maleimide, and using methods described in Lutolf, et al., "Synthetic matrix metalloproteinase-sensitive hydrogels for the conduction of tissue regeneration: engineering cell-invasion characteristics," *Proc. Natl. Acad. Sci. U.S.A* (2003), which is incorporated by reference herein in its entirety, to form polyethylene glycol-vinyl sulfone by coupling PEG-OH with an excess of divinyl sulfone).

Relative Amount of Nucleo-Functional Polymer and Electro-Functional Polymer

The compositions or formulations for forming an extended-release hydrogel for extended-release of a drug for treatment of various disorders, including ocular disorders, can be characterized according to the relative amount of nucleo-functional polymer and electro-functional polymer used. Accordingly, in certain embodiments, the mole ratio of (i) thio-functional groups —$R^1$—SH to (ii) thiol-reactive group is in the range of about 10:1 to about 1:10. In certain embodiments, the mole ratio of (i) thio-functional groups —$R^1$—SH to (ii) thiol-reactive groups is in the range of about 2:1 to about 1:2. In some embodiments the mole ratio of (i) thio-functional groups —$R^1$—SH to (ii) thiol-reactive groups is in the range of about 0.8:1 to about 1.2:1.

Once combined, the combination of the nucleo-functional polymer and the electro-functional polymer in certain embodiments are present in solution in the range of about 25 mg/mL to about 150 mg/mL, including all values and ranges therein, and in some embodiments are present in solution in the range of about 25 mg/mL to about 100 mg/mL, and in certain embodiments about 90 mg/mL.

Features of the Extended-Release Hydrogel System
Administration of the Formulations to Form an Extended-Release Hydrogel The compositions or formulations for forming an extended-release hydrogel for extended-release of a drug for treatment of various disorders, including ocular disorders, can be characterized according to the features of administration. Accordingly, in certain embodiments, the nucleo-functional polymer, electro-functional polymer and pharmaceutical agent may be administered through topical, epidermal, subdermal, intra-adipose, intramuscular, intraperitoneal, intravenous, intra-arterial, intracranial, intranasal, and/or intrauterine administration. In some embodiments, the nucleo-functional polymer, electro-functional polymer and pharmaceutical agent may be administered through injection. The nucleo-functional polymer, electro-functional polymer and pharmaceutical agent may be administered to any site of a subject where it is desired and appropriate to provide an extended-release hydrogel. In certain embodiments, the nucleo-functional polymer, electro-functional polymer and pharmaceutical agent may be administered to the eye of a subject (e.g., by injection). In some embodiments, the nucleo-functional polymer, electro-functional polymer and pharmaceutical agent may be administered into the air-filled void within the posterior cavity of the eye of a subject following a vitrectomy. In certain embodiments, the nucleo-functional polymer, electro-functional polymer and pharmaceutical agent may be administered in a manner as to fill or partially fill the air-filled void remaining in the eye of a subject following a complete or partial vitrectomy. In either case the amount of formulation that is delivered could be, for example, in a range between about 1 mL to about 6 mL, including all values and ranges therein.

In some embodiments, the nucleo-functional polymer, electro-functional polymer and pharmaceutical agent may be administered as a single formulation (e.g., the nucleo-functional polymer, electro-functional polymer and pharmaceutical agent are mixed prior to administration). In certain embodiments, the nucleo-functional polymer, electro-functional polymer and pharmaceutical agent may be administered as two or more separate formulations that can mix at the target site of the subject to form the hydrogel. In certain embodiments, the nucleo-functional polymer, electro-functional polymer and pharmaceutical agent may be administered as two or more separate formulations that mix within the delivery device to form the extended-release hydrogel as the mixture exits the device. In some embodiments, the pharmaceutical agent is included in a formulation comprising the nucleo-functional polymer prior to administration. In certain embodiment the pharmaceutical agent is included in a formulation comprising the electro-functional polymer prior to administration. In certain embodiment the pharmaceutical agent is included in a formulation comprising the electro-functional polymer and in a formulation comprising the nucleo-functional polymer prior to administration. In certain embodiments, the pharmaceutical agent is included in a formulation comprising both the nucleo-functional polymer and the electro-functional polymer prior to administration.

Transmittance of the Extended-Release Hydrogel

The extended-release hydrogel can be characterized by the transmittance of the hydrogel. Hydrogels to be used in various sites of a subject, for example in the eye, for extended release of drugs may require that the hydrogel be optically clear with transparency of at least about 80% for light in the visible spectrum when measured through a hydrogel having a thickness of 2 cm. In certain embodiments, the hydrogel has a transparency of at least about 85% for light in the visible spectrum when measured through hydrogel having a thickness of 2 cm. In certain embodiments, the hydrogel has a transparency of at least about 90% for light in the visible spectrum when measured through hydrogel having a thickness of 2 cm.

Generally, in order to reduce scattering and increase transmittance of light, the size of the particles in the hydrogel must be less than about the wavelength of visible light, therefore in certain embodiments the size of any particle form of a pharmaceutical agent in the hydrogel should be less than about 400 nm. In certain embodiments, the size of the particle form of a pharmaceutical agent in the hydrogel is between about 25 nm and about 200 nm including all ranges therein. In some embodiments the size is between about 50 nm and about 100 nm.

For use in the eye it is important to ensure adequate transmittance, for example, greater than about 80%, and the concentration of pharmaceutical agent particles and their size can impact transmittance. In certain embodiments for use in the eye, the concentration of 50 nM pharmaceutical agent particles is between about 0.025% and about 0.001%, including all ranges therein.

Crosslink Time of the Polymers to Form the Extended-Release Hydrogel

The compositions or formulations for delivery of an extended-release hydrogel to a target site of a subject, for example the eye, can be characterized by the crosslink time of the polymers in the formulation (i.e., how long it takes for the hydrogel to form once the nucleo-functional polymer has been combined with the electro-functional polymer). For delivery to various target sites in a subject, for example the eye following vitrectomy, crosslink time should be less than about 10 minutes so that the patient does not need to remain in the surgical position for too long after administration. In certain embodiments, the crosslink time of the disclosed extended-release hydrogels is less than about 7 minutes, when measured at 37° C., and in some embodiments is less than about 5 minutes, when measured at 37° C. In certain embodiments, the crosslink time of the disclosed extended-release hydrogels is less than about 3 minutes, when measured at 37° C., and in some embodiments is less than about 1 minute.

Administration of the Formulation to the Eye

The compositions or formulations for forming an extended-release hydrogel for treatment of ocular disorders can be further characterized according to the features of administration. Accordingly, in certain embodiments, the nucleo-functional polymer, electro-functional polymer and pharmaceutical agent may be administered as an injection into the eye (e.g., the vitreous) without performing a vitrectomy. In certain embodiments, the nucleo-functional polymer, electro-functional polymer and pharmaceutical agent may be administered as an intravitreal injection. In the case of intravitreal injection, the amount of formulation that is delivered in certain embodiments is between about 25 μL to about 500 μL, including all values and ranges therein and in certain embodiments between about 50 μL and 200 μL. In some embodiments, the nucleo-functional polymer, electro-functional polymer and pharmaceutical agent may be administered as a single formulation to the eye. In certain embodiments, the nucleo-functional polymer, electro-functional polymer and pharmaceutical agent may be administered as two or more separate formulations that can mix at the target site (e.g., the vitreous cavity of the eye) to form the extended-release hydrogel. In certain embodiments, the nucleo-functional polymer, electro-functional polymer and pharmaceutical agent may be administered as two or more separate formulations that mix within the delivery device to form the extended-release hydrogel as the mixture exits the device. In certain embodiments, the two separate formulations combine and mix within the injection cannula of a delivery device. The injection cannula device may have a mixing chamber that tapers into a small gauge needle that allows for entry into the eye. In some embodiments, the pharmaceutical agent is included in a formulation comprising the nucleo-functional polymer prior to administration. In certain embodiment the pharmaceutical agent is included in a formulation comprising the electro-functional polymer prior to administration. In some embodiments, the pharmaceutical agent is included in a formulation comprising the nucleo-functional polymer and in a formulation comprising the electro-functional polymer prior to administration. In certain embodiments, the pharmaceutical agent is included in a formulation comprising both the nucleo-functional polymer and the electro-functional polymer prior to administration.

Crosslink Time of the Polymers for Forming an Extended-Release Hydrogel in the Eye The compositions or formulations for delivery to the eye (e.g., as an intravitreal injection) can also be characterized by the crosslink time of the polymers to form the extended-release hydrogel. For delivery to the eye (e.g., as an intravitreal injection), in certain embodiments it is desirable for composition to form a solid hydrogel quickly to avoid diffusion from the site of injection and to ensure a consistent shape/form factor of the extended-release hydrogel. In certain embodiments, the crosslink time of the extended-release hydrogels described herein is less than about 30 seconds after combining the nucleo-functional polymer with the electro-functional polymer, when measured at 37° C. In certain embodiments the crosslink time is less than about 20 seconds after combining the nucleo-functional polymer with the electro-functional polymer, when measured at 37° C., and in some embodiments the crosslink time is less than about 10 seconds after combining the nucleo-functional polymer with the electro-functional polymer, when measured at 37° C. In certain embodiments, the crosslink time of the hydrogels described herein is less than about 5 seconds, less than about 3 seconds, less than about 2 seconds, or less than about 1 second after combining the nucleo-functional polymer with the electro-functional polymer, when measured at 37° C.

Ocular-Specific Formulation Considerations

A major risk with the use of products administered to the eye (e.g., intravitreally-administered products) is the risk of a sterile inflammatory reaction due to unacceptably high levels of endotoxin. (Wang, et al., "Acute intraocular inflammation caused by endotoxin after intravitreal injection of counterfeit bevacizumab in Shanghai, China," Ophthalmology 120(2):355-61 (2013)) The ocular environment is particularly sensitive to endotoxins and sterile inflammatory reactions can be seen with formulations not specifically developed for intravitreal use. (Marticorena, et al., "Sterile endophthalmitis after intravitreal injections," *Mediators Inflamm.* 2012:928123 (2012)) In certain embodiments, the compositions and formulations described herein comprise less than or equal to about 0.2 endotoxin units (EU)/mL, a limit even lower than ISO standards 15798 & 11979-8 which recommend no more than (NMT) 0.5 EU/ml. In some embodiments, the compositions and formulations described herein comprises less than or equal to about 0.5 endotoxin units (EU)/mL. In addition, safety concerns of using unbuffered saline as a vehicle for intravitreal injection have been raised in the literature. Intravitreal injection of normal saline has been observed to induce vacuoles in the photoreceptor outer segments and RPE cells, as well as upregulation of inflammatory mediators including TNF-α, IL-1β, IL-6, and VEGF. These histopathological and cytokine markers have not been observed in mouse eyes that were injected with phosphate buffered vehicle (PBS) (Hombrebueno, et al., "Intravitreal Injection of Normal Saline Induces Retinal Degeneration in the C57BL/6J Mouse," *Trans Vis Sc Technol.* 3(2):3 (2014)), which in certain embodiments is the vehicle used for administration of the formulations described herein.

Features of the Pharmaceutical Agent

The extended-release hydrogel formed by the formulations described herein may act as a drug depot that may be used to deliver various pharmaceutical agents over an extended period of time. The pharmaceutical agents that may be use in the formulations and extended-release hydrogels described herein include anti-inflammatory agents, steroids, NSAIDS, intraocular pressure lowering drugs, antibiotics, pain relievers, inhibitors of vascular endothelial growth factor (VEGF), inhibitors of abnormal vascular growth or vascular leakage, inhibitors of abnormal cell proliferation, chemotherapeutics, anti-viral drugs, gene therapy viral vectors, etc., and combinations thereof. The pharmaceutical agents may be small molecules, proteins, DNA/RNA fragments, glycosaminoglycans, carbohydrates, nucleic acid, inorganic and organic biologically active compounds or other configurations, active portions of any of the proceeding molecules, and combinations thereof. The pharmaceutical agent may be soluble or non-soluble, or combinations thereof in the pharmaceutically acceptable carrier. The pharmaceutical agent may be dissolved in the composition or formulation, suspended as particles or encapsulated in particles (e.g., liposomes, amphiphilic polymer or solid polymer particles) and suspended, and combinations thereof. In some embodiments, the formulations and/or extended-release hydrogel comprises more than one pharmaceutical agent. In certain embodiments, one or more pharmaceutical agent is included in the formulation comprising the nucleo-functional polymer. In certain embodiments, one or more pharmaceutical agent is included in the formulation comprising the electro-functional polymer. In certain embodiments, one or more pharmaceutical agent is included in the formulation comprising the nucleo-functional polymer and in the formulation comprising the electro-functional polymer. In some embodiments, one or more pharmaceutical agents is included in a formulation comprising both the nucleo-functional polymer and the electro-functional polymer.

Features of the Extended-Release Hydrogel for Controlling Drug-Delivery

The compositions or formulations for forming an extended-release hydrogel for extended-release of a drug for the treatment of various disorders, including ocular disorders, can be further characterized according to the features of the extended-release hydrogel that control the release of the pharmaceutical agent into the local environment. Features of the extended-release hydrogel formulation for controlling the release of the pharmaceutical agent include: crosslink density or porosity, biodegradation rate, and a combination thereof.

Crosslink Density or Porosity of the Extended-Release Hydrogel

Following the administration of the composition or formulation comprising a nucleo-functional polymer, an electro-functional polymer and one or more pharmaceutical agents within the target site (e.g., the eye), the one or more pharmaceutical agents will diffuse out of the extended-release hydrogel into the surrounding environment. The crosslink density of the resultant extended-release hydrogel acts as a barrier to the diffusion of the one or more pharmaceutical agents within the hydrogel. A higher crosslink density results in a smaller pore size (i.e., distance between crosslinks). If the pore size is close to or less than the hydrodynamic radius of the pharmaceutical agent, then diffusion of the agent will be impeded and release from the hydrogel will be delayed. The crosslinking density of the extended-release hydrogel can be controlled by the molecular weight of the nucleo-functional and electro-functional polymers and the number of functional groups present on each polymer. A lower molecular weight between crosslinks will yield a higher crosslinking density as compared to a higher molecular weight. As previously described, in certain embodiments, the nucleo-functional polymer has a weight-average molecular weight in the range of from about 4,000 g/mol to about 100,000 g/mol and the electro-functional polymer has a molecular weight in the range of from about 500 g/mol to about 100,000 g/mol. Similarly, the molecular weight of each arm in a multi-arm electro-functional polymer has an impact on the porosity of the extended-release hydrogel. Therefore, a multi-arm electro-functional polymer with a lower molecular weight has a higher crosslink density and smaller pore size than a higher molecular weight multi-arm polymer.

The crosslinking density may also be controlled by the concentrations of the nucleo-functional polymer and the electro-functional polymer. Increasing the total concentration increases the cross-linking density as the likelihood or probability that an electro-functional group will combine with a nucleo-functional group and form a crosslink increases. Crosslink density may also be controlled by adjusting the relative amount of nucleo-functional polymer and electro-functional polymer used. A molar ratio of thio-functional groups to thiol-reactive groups of about 1:1 leads to the highest crosslink density.

Degradation Rate of the Extended-Release Hydrogel

The length of time over which the one or more pharmaceutical agents can be delivered within the target site (e.g., the eye) and surrounding environment is also a function of the length of time the extended-release hydrogel is present within the site, i.e., degradation rate or degradation time of the extended-release hydrogel. Degradation rate or time can be thought of as the rate or length of time it takes for the extended-release hydrogel to be completely in solution, i.e., for no solid mass to remain or be observed. In certain embodiments, degradation rate or time can be measured by placing the extended-release hydrogel in a solution of PBS and assaying for the presence of the extended-release hydrogel (solid mass) over time. Degradation rate or time may also be measured at different temperatures (e.g., 37° C. or 60° C.) with higher temperature leading to a faster degradation rate and faster time to complete degradation. In certain embodiments, the degradation time of the extended-release hydrogels described herein is greater than or equal to about 20, 40, 60, 69, 80, 90, 94, 100, 120, 140, or 158 days at 37° C. In some embodiments, the degradation time of the extended-release hydrogels described herein is greater than or equal to about 3, 5, 8, 10, 14, 19, 20, 25, 30, or 32 days at 60° C.

Pharmaceutical Compositions or Formulations

One aspect of the invention provides pharmaceutical compositions or formulations. In certain embodiments, the pharmaceutical composition or formulation comprises (i) a nucleo-functional polymer; (ii) a pharmaceutical agent; and (iii) a pharmaceutically acceptable carrier for administration to the desired target site. In some embodiments, the pharmaceutical composition or formulation comprises (i) an electro-functional polymer; (ii) a pharmaceutical agent; and (iii) a pharmaceutically acceptable carrier for administration to the desired target site. In certain embodiments, the pharmaceutical composition or formulation comprises (i) a nucleo-functional polymer; (ii) an electro-functional polymer; (iii) a pharmaceutical agent; and (iv) a pharmaceutically acceptable carrier for administration to the desired target site. In some embodiments, the target site is the eye of a subject. In certain embodiments, the target site is the eye of a human. In some embodiments, the pharmaceutical composition or formulation is a liquid pharmaceutical composition or composition. In certain embodiments, the pharmaceutical composition or formulation is a lyophilized pharmaceutical composition or formulation. In some embodiments, the pharmaceutically acceptable carrier is PBS, water, or a combination thereof. In some embodiments the PBS is 1×PBS and in certain embodiments the PBS is 5×PBS. In certain embodiments, the PBS comprises about 50 mM to about 90 mM sodium chloride, about 2.5 mM to about 3 mM potassium chloride, about 50 mM sodium phosphate, about 9 nM potassium phosphate, or combinations thereof.

In certain embodiments, the pharmaceutical composition or formulation is sterile and may optionally comprise a preservative, antioxidant, and/or other excipients. Exemplary excipients include, for example, acacia, agar, alginic acid, bentonite, carbomers, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, glyceryl behenate, guar gum, hectorite, hydrogenated vegetable oil type I, hydroxyethyl cellulose, hydroxyethylmethyl cellulose, hydroxypropyl cellulose, hydroxypropyl starch, hypromellose, magnesium aluminum silicate, maltodextrin, methylcellulose, polydextrose, polyethylene glycol, poly (methylvinyl ether/maleic anhydride), polyvinyl acetate phthalate, polyvinyl alcohol, potassium chloride, povidone, propylene glycol alginate, saponite, sodium alginate, sodium chloride, stearyl alcohol, sucrose, sulfobutylether (3-cyclodextrin, tragacanth, xanthan gum, and derivatives and mixtures thereof. In some embodiments, the excipient is a bioadhesive or comprises a bioadhesive polymer.

In some embodiments, the concentration of the excipient in the pharmaceutical composition or formulation ranges from about 0.1 to about 20% by weight. In certain embodiments, the concentration of the excipient in the pharmaceutical composition or formulation ranges from about 5 to about 20% by weight. In certain embodiments, the concentration of the excipient in the pharmaceutical composition or formulation is less than about 20%, less than about 15%, less than about 10%, less than about 9%, less than about 8%, less than about 7%, less than about 6%, less than about 5%), less than about 4%, less than about 3%, less than about 2%, less than about 1.8%, less than about 1.6%, less than about 1.5%, less than about 1.4%, less than about 1.2%, less than about 1%, less than about 0.9%, less than about 0.8%, less than about 0.7%, less than about 0.6%, less than about 0.5%, less than about 0.4%, less than about 0.3%, less than about 0.2%, or less than about 0.1% by weight.

The pharmaceutical composition or formulation may be further characterized according to its viscosity. In certain embodiments, the viscosity of the pharmaceutical composition is less than about 4000 cP, less than about 2000 cP, less than about 1000 cP, less than about 800 cP, less than about 600 cP, less than about 500 cP, less than about 400 cP, less than about 200 cP, less than about 100 cP, less than about 80 cP, less than about 60 cP, less than about 50 cP, less than about 40 cP, less than about 20 cP, less than about 10 cP, less than about 8 cP, less than about 6 cP, less than about 5 cP, less than about 4 cP, less than about 3 cP, less than about 2 cP, less than about 1 cP. In some embodiments, the viscosity of the pharmaceutical composition or formulation is at least about 4,000 cP, at least about 2,000 cP, at least about 1,000 cP, at least about 800 cP, at least about 600 cP, at least about 500 cP, at least about 400 cP, at least about 200 cP, at least about 100 cP, at least about 80 cP, at least about 60 cP, at least about 50 cP, at least about 40 cP, at least about 20 cP, at least about 10 cP, at least about 8 cP, at least about 6 cP, at least about 5 cP, at least about 4 cP, at least about 3 cP, at least about 2 cP, at least about 1 cP. In certain embodiments, the viscosity of the pharmaceutical composition or formulation is about 4,000 cP, about 2,000 cP, about 1,000 cP, about 800 cP, about 600 cP, about 500 cP, about 400 cP, about 200 cP, about 100 cP, about 80 cP, about 60 cP, about 50 cP, about 40 cP, about 20 cP, about 10 cP, about 8 cP, about 6 cP, about 5 cP, about 4 cP, about 3 cP, about 2 cP, about 1 cP. In some embodiments, the viscosity of the viscosity of the pharmaceutical composition or formulation is between about 5 cP and about 50 cP.

In some embodiments, the pharmaceutical composition or formulation may be further characterized according to its pH. In certain embodiments, the pharmaceutical composition or formulation has a pH in the range of from about 5 to about 9, or about 6 to about 8. In certain embodiments, the pharmaceutical composition or formulation has a pH in the range of from about 6.5 to about 7.5. In certain embodiments, the pharmaceutical composition or formulation has a pH of about 7.

In certain embodiments, the pharmaceutical composition or formulation comprises water, and the composition or formulation has a pH in the range of about 7.1 to about 7.7. In certain embodiments, the pharmaceutical composition or formulation comprises water, and the composition or formulation has a pH in the range of about 7.1 to about 7.6, about 7.1 to about 7.5, about 7.1 to about 7.4, about 7.2 to about 7.6, about 7.2 to about 7.5, about 7.2 to about 7.4, about 7.2 to about 7.3, about 7.3 to about 7.7, about 7.3 to about 7.6, about 7.3 to about 7.5, about 7.3 to about 7.4, about 7.4 to about 7.7, about 7.4 to about 7.6, or about 7.4 to about 7.5. In certain embodiments, the pharmaceutical composition or formulation comprises water, and the composition or formulation has a pH in the range of about 7.3 to about 7.5. In certain embodiments, the pharmaceutical composition or formulation comprises water, and the composition or formulation has a pH of about 7.4.

The pharmaceutical composition or formulation may be further characterized according to its osmolality and the presence and/or identity of salts. For example, in certain embodiments, the pharmaceutical composition or formulation has an osmolality in the range of about 200 mOsm/kg to about 400 mOsm/kg. In certain embodiments, the pharmaceutical composition or formulation has an osmolality in the range of about 250 mOsm/kg to about 350 mOsm/kg. In certain embodiments, the pharmaceutical composition or formulation has an osmolality in the range of about 280 mOsm/kg to about 320 mOsm/kg. In certain embodiments, the pharmaceutical composition or formulation has an osmolality of about 300 mOsm/kg. In certain embodiments, the pharmaceutical composition or formulation further comprises an alkali metal salt. In certain embodiments, the pharmaceutical composition or formulation further comprises an alkali metal halide salt, an alkaline earth metal halide salt, or a combination thereof. In certain embodiments, the pharmaceutical composition or formulation further comprises sodium chloride. In certain embodiments, the pharmaceutical composition or formulation further comprises sodium chloride, potassium chloride, calcium chloride, magnesium chloride, or a combination of two or more of the foregoing. In certain embodiments, the pharmaceutical composition or formulation comprises phosphate buffered saline (PBS). In some embodiments, the PBS comprises one or more of sodium chloride, potassium chloride, sodium phosphate and potassium phosphate. In some embodiments the PBS is 1×PBS and in certain embodiments the PBS is 5×PBS. In certain embodiments, the PBS comprises about 50 mM to about 90 mM sodium chloride, about 2.5 mM to about 3 mM potassium chloride, about 50 mM sodium phosphate, about 9 nM potassium phosphate, or combinations thereof.

The pharmaceutical composition or formulation may be further characterized according to the level of endotoxins present in the composition or formulation. In certain embodiments, the composition or formulation has an endotoxin level of less than about 20 endotoxin units/ml, less than about 15 endotoxin units/ml, less than about 10 endotoxin units/ml, less than about 5 endotoxin units/ml, less than about 2.5 endotoxin units/ml, less than about 1.0 endotoxin units/ml, less than about 0.8 endotoxin units/ml, less than about 0.5 endotoxin units/ml, less than about 0.2 endotoxin units/ml, or less than about 0.1 endotoxin units/ml.

The pharmaceutical composition or formulation may also be characterized by the size and number of any particles, including any drug particles, present in the composition or formulation. In certain embodiments, the composition or formulation has less than about 50 particles per mL with a size of ≥10 μm. In some embodiments, the composition or formulation has less than about 5 particles per mL with a size of ≥25 μm.

Kits for Use in Medical Applications

Another aspect of the invention provides a kit for treating a disorder. In certain embodiments, the kit comprises: i) a formulation comprising a nucleo-functional polymer and a pharmaceutical agent and ii) a formulation comprising an electro-functional polymer. In some embodiments, the kit comprises: i) a formulation comprising a nucleo-functional polymer and ii) a formulation comprising an electro-functional polymer and a pharmaceutical agent. In some embodiments, the kit comprises: i) a formulation comprising a nucleo-functional polymer and a pharmaceutical agent and ii) a formulation comprising an electro-functional polymer and a pharmaceutical agent. In certain embodiments, the kit comprises: i) a formulation comprising a nucleo-functional polymer; ii) a formulation comprising a pharmaceutical agent, and iii) a formulation comprising an electro-functional polymer. In some embodiments one or more the formulations provided in the kit comprises a pharmaceutically acceptable carrier. In certain embodiments, the pharmaceutically acceptable carrier comprises PBS. In some embodiments the PBS is 1×PBS and in certain embodiments the PBS is 5×PBS. In certain embodiments, the PBS comprises about 50 mM to about 90 mM sodium chloride, about 2.5 mM to about 3 mM potassium chloride, about 50 mM sodium phosphate, about 9 nM potassium phosphate, or combinations thereof. In some embodiments, the kit further comprises instructions for administering the formulations to a target site of interest in a subject, for example, the eye of a subject. In some embodiments, the kit further comprises the components and/or accessories required to prepare and administer the formulations to a target site of interest in a subject, for example the eye of a subject.

The description above describes multiple aspects and embodiments of the invention. The patent application specifically contemplates all combinations and permutations of the aspects and embodiments.

Medical Devices and Methods for Focal Delivery of Hydrogel-Forming Formulations and Compositions Certain embodiments for forming a hydrogel in a tissue of interest, for example, forming a hydrogel that acts as a retinal tamponade in the vitreous cavity of the eye comprise forming the hydrogel by filling the majority of the air-filled posterior chamber cavity of the eye with the polymer composition or formulation that forms that hydrogel. In such embodiments, the air-filled vitreous cavity becomes a largely hydrogel-filled area with a small layer of air or saline above the gel line in the posterior chamber of the eye. For such embodiments, pre-clinical work was conducted and determined that the gel is well tolerated and does not result in adverse events in an animal vitrectomy model.

Figure 5:
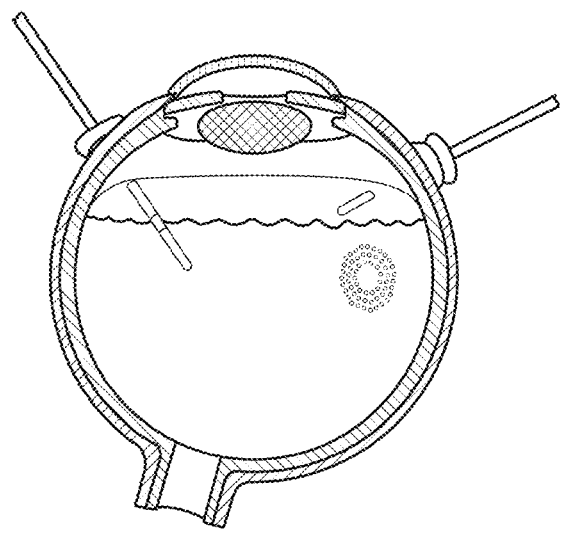
FIG. 5 shows a complete fill of the eye with a hydrogel, covering a retinal break

In some embodiments, however, large volumes of hydrogel may result in certain adverse events, namely elevated intraocular pressure as the large amount of hydrogel breaks down and is cleared from the eye. In some embodiments, these adverse events appear to correlate with the large volume of polymer composition or formulation introduced in the eye and the large amount of resulting hydrogel in the eye in order for the gel to fill the posterior chamber and seal all the retinal breaks; retinal breaks typically occur on the edges of the retina, therefore one has to use a significant amount of hydrogel to cover the breaks completely (FIG. 5).

In certain embodiments, mitigation efforts to reduce the risk of elevated intraocular pressure in the design of the hydrogel may be implemented at a molecular level and/or in the surgical technique employed to deliver the gel intraoperatively. Molecular level changes may include the length and weight of the polymer backbones described herein, percent thiolation, percent of solids, and degree of cross linking density that may be used as described herein. In certain embodiments, surgical technique and intraoperative considerations to reduce these adverse events may include not filling the eye completely with the hydrogel-forming polymer or hydrogel itself to the pars plana (the anatomical structure at the edge of the retina), thereby reducing the volume of the formulations and compositions disclosed herein injected and subsequently cleared from the eye. However, these mitigation efforts may not be enough to control elevated intraocular pressure from the hydrogel in certain circumstances and, as described further below, different and new approaches may be required for developer a more clinically useful product.

In certain embodiments, to mitigate the potential risk of intraocular pressure rise, that the inventors determined that one may need to inject less foreign material (e.g., the disclosed polymer formulations and compositions) into the eye. Thus, in certain embodiments in order to target only the site of hydrogel deposition, for example, the sited of a retinal tear in the eye, it was necessary to invent a novel method of sealing retinal breaks that would involve the use of minimal amounts of the hydrogel material formed by the polymer compositions and formulations described herein. Therefore, another aspect of the invention is a delivery device that allows for focal administration of the hydrogel formed by the polymer compositions and formulations described herein, to specific areas of interest. Such areas include the vitreous cavity and formation of a retinal tamponade at a target site in order to minimize the amount of hydrogel injected into the target tissue, such as the eye. In certain embodiments, specialized applicators are used to provide the polymer compositions described herein at a target site, including devices to mist or spray, atomize, brush on, roll on, or any other mechanism by which the hydrogel-forming compositions and formulations are mechanically directed to a specific area of the target tissue (e.g., vitreous cavity).

The inventors therefore created novel devices and methods for focally applying the polymers and hydrogels described herein to tissue target sites of interest, including the vitreous cavity, just to the areas requiring the hydrogel, such as the formation of a retinal tamponade at a target site of pathology. The unique features of the herein described polymer formulations and compositions and hydrogels may prevent the application of the hydogel "as-is" in a focal manner to a target site, such as a retinal break. In certain embodiments, the hydrogel-forming polymer compositions and formulations described herein at time of initial application are a non-viscous liquid and retinal breaks are almost always at the anterior aspect of the retina (vertically, on the sides of the eye wall). Application of any appreciable volume of a non-viscous liquid to a retinal break would then result in the composition and/or resulting hydrogel running down the eye wall posteriorly. This would result in a failure to apply the gel to the site of pathology and would not satisfy the requirement, in certain embodiments, of introducing a minimal amount of polymer formulation or composition or hydrogel to ensure improved clinical safety. Although the hydrogel-forming compositions or formulations described herein could be made to be viscous by increasing the molecular weight of the individual components, or by increasing the percent solids, in certain embodiments this would be undesired as it would increase the overall amount of solid material in the eye and increase the risk of an intraocular pressure rise. Thus, in certain embodiments there is a need to transform the flow properties of the polymer formulations and compositions described herein without changings its chemical constituents.

In the specific example of the eye, others have recognized that retinal breaks may be sealed by applying a "patch" to the retinal break. (See Ren 2019, Teruya 2009, Schwartz 2000, Medicus 2017). The unique features of the polymers and hydrogel system described herein, however, generally do not allow for application as a patch and therefore, the inventors created novel methods and devises. In certain embodiments, using the herein described polymer and hydrogel systems as a patch may have undesirable results. For example, in certain embodiments due to the non-viscous nature of the polymer compositions and hydrogel prior to cross-linking, a jet stream may emerge when attempting to gently "patch" retinal breaks. Such a jet stream could potentially damage the very sensitive retina or underlying structures. In certain embodiments, even single drops of the polymer formulation or hydrogel system may be too heavy, causing the formulation to roll down the side of the peripheral retinal wall down to the posterior pole of the eye rendering it ineffective at providing any sealant effect at the site of the peripheral retinal wall. In certain embodiments, to make the product more similar to a "patch" as described above, long-chain polymers could be added to enhance the viscosity of the product. However, in certain embodiments a key objective is for the polymer formulations and compositions and/or hydrogel to be non-viscous at time of injection to more readily allow for effective administration at target sites. Thus, in certain embodiments the addition of additives to enhance the viscosity of the polymer compositions and formulations and/or hydrogels described herein would be contrary to the performance requirement to be a non-viscous liquid for focal administration.

Figure 6:
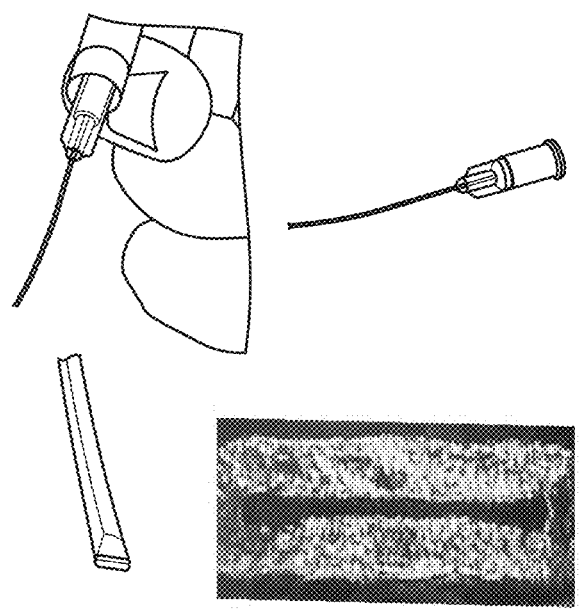
FIG. 6 shows a cannula of the invention with a fabricated 20 micron aperture to permit emergence of polymer formulation of hydrogel as a mist when injected under high pressure.

Through the course of experimentation, the inventors have devised several approaches to focally apply the polymer formulations and compositions and hydrogels described herein, for example to act as a retinal tamponade at specific areas of the vitreal cavity. Certain embodiments include a unique cannula device with tapered and micron sized holes at the distal tip of the cannula, to allow for non-viscous hydrogel-forming polymer formulations and compositions and/or hydrogels described herein to emerge from the cannula as a very fine mist. In some embodiments, the cannula device is designed specifically for intraocular administration. Various tapered tips to form narrow channels could also be used and in certain embodiments the cannula, acting as an "mister" or "atomizer" producing droplets which result in a focal application of the formulation or hydrogel to a specific area of the tissues, such as to form a tamponade at a specific area of the vitreal cavity. In some embodiments, multiple applications of the fine mist can be re-applied in one or more layers to provide the desired sealant effect as the hydrogel solidifies in place, but while using an injection volume on the micro-liter scale, as opposed to the multiple milliliters used in certain embodiments to fill the tissue, such as filling the vitreous cavity. The inventors have created the cannulas described above as no such device exists, in particular in ophthalmic surgery at the present time. Various cannula designs can be used in this unique application technique including curved and un-curved cannulas with various manipulations to the distal portion to create precise channels, grooves, and/or apertures that would allow for the formulations and/or gel to emerge as a mist. (FIG. 6). In certain embodiments, pressure for delivery of the gel solution may be created by applying firm pressure to the syringe, or through the use of a Viscous Fluid Injector on a vitrectomy machine or other controlled pressure injection systems. Other embodiments of the invention include various tapered tips or a matrix of small holes in the distal tip of a closed end cannula to create similarly narrow channels that allow for differing droplet sizes to emerge from the cannula tip. Other embodiments may include the use of pressured air to achieve an optimal spray pattern or droplet size.

Figure 7:
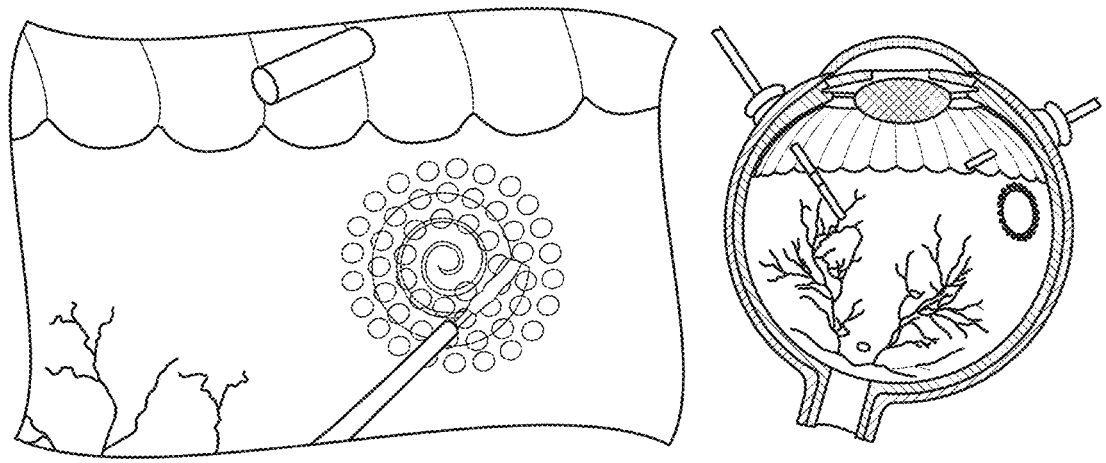
FIG. 7 shows a viscous tamponade agent that remains in place when applied to the retinal surface.
Figure 8:
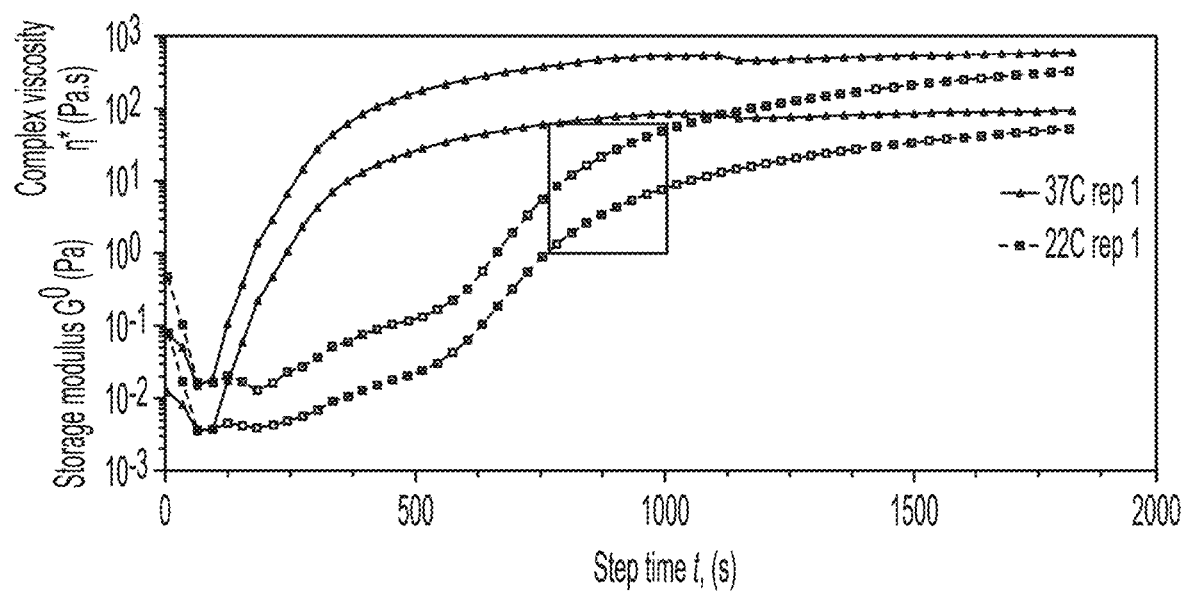
FIG. 8 shows desired viscosity range in certain embodiments for application of dynamically cross-linking hydrogel to the retinal surface, allowing for adhesion without loss down the surface of the retinal wall.

In another embodiment, the unique features of the polymers and hydrogels described herein may be employed in a method to focally apply the formulations and/or hydrogel to a retinal break by gently brushing the polymer formulation or composition, or the hydrogel, onto the site while the material is in its viscous phase, but before it becomes a semi-solid gel. As described above, in certain embodiments the gel solution is initially a non-viscous liquid immediately after mixing. However, in some embodiments as the solution begins to crosslink, the viscosity begins to increase. Based on the particular formulation employed as described herein (percent polymer in the solution, molecular weight of the polymers, number of reactive side groups, etc.) the change in viscosity at room temperature, the temperature under which the solution is being applied, occurs over ~10-20 minutes. In certain embodiments, once the viscosity of the formulation or gel solution reaches a certain level, in the range of 500-1000cps, the formulation or gel solution will stay where placed on the retina and not run down the eye wall posteriorly (FIG. 7). This is referred to as the "injection window." (FIG. 8).

Figure 9:
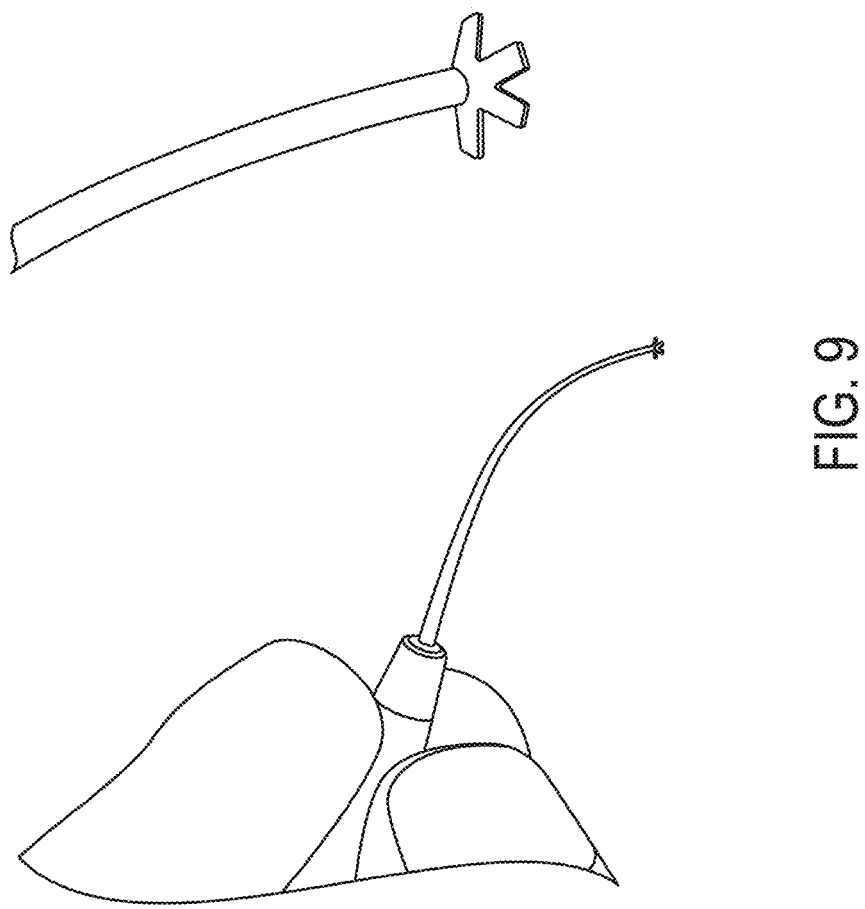
FIG. 9 shows an exemplary curved, brush-tip cannula for intraocular manipulation of a polymer formulation or hydrogel on the retinal surface.

In some embodiments, once the formulation or gel solution reaches a viscosity of greater than ~5000-10,000cps, it becomes too viscous to apply in a smooth layer and will not adhere to the site of application. The formulation or hydrogel in this manner may be applied by using a soft-tip cannula with or without slits in the soft-tip acting as brush bristles, thus applying the formulation or hydrogel by brushing it into place, to allow for a targeted and precise application. (FIG. 9). Alternatively, in certain embodiments the distal tip may be comprised of a soft porous foam through which the viscous formulation or hydrogel solution may be injected and brushed onto the surface of the target site, such as the retina.

In certain embodiments, the cannula may be straight or curved. In some embodiments, a curved cannula may be desirable for directing the tip towards the target site, such as the side wall without striking the natural crystalline lens, which would result in a cataract forming if inadvertently struck. In some embodiments, certain cannulas may be made of pliable metals, such as nitinol, to allow for the comfortable passage through valved entry cannula in the target site, such as the pars plana. In certain embodiments, the formulation or hydrogel may be applied through a cannula by hand force with a syringe or through an automated system, such as a viscous fluid injector. Other embodiments of the cannula may be used to deliver precise amounts of polymer formulation and/or hydrogel comprising a therapeutic agent, such as an active pharmaceutical ingredient in the form of a small molecule, peptide, oligonucleatirde, viral vector, or even a dye, or other agent to a specific part of the tissue, such as the eye or other organ. In certain embodiments, such agents may be used to provide protection against infection, inflammation, anti-proliferation, malignancy, amongst other uses.

Methods of application need not be limited to focal areas where retinal breaks are present. Such a cannula could be used to apply any liquid substance focally into the eye or any other tissue where a focal sealant or hydrogel is clinically desirable. Examples in the eye include, but are not limited to, applying to macular holes, retinal lesions, membranes, or other vitreoretinal indications.

Citations are made to the following references, each of which is incorporated by reference herein in its entirety: U.S. Pat. Nos. 10,874,767; 6,149,931; 9,623,144; and 9,072,809; Ren, X. J., Bu, S. C., Wu, D., Liu, B. S., Yang, F. H., Hu, B. J., et al. (2019). PATCHING RETINAL BREAKS WITH HEALAFLOW IN 27-GAUGE VITRECTOMY FOR THE TREATMENT OF RHEGMATOGENOUS RETINAL DETACHMENT. Retina (Philadelphia, Pa.), Publish Ahead of Print. http://doi.org/10.1097/IAE.0000000000002701; and K Teruyal, J Suedal, M Arail, N Tsurumarul, R Yamakawal, A Hirata2 and T Hirose3. Patching retinal breaks with Seprafilms in experimental rhegmatogenous retinal detachment of rabbit eyes Eye (2009) 23, 2256-2259

EXAMPLES

The following examples are included merely for purposes of illustration of certain aspects and embodiments of the present invention, and are not intended to limit the invention.

Example 1A—Effect of Tihiol-Reactive Group on Degradation and Crosslink Time of Hydrogels Hydrogels were prepared from formulations that resulted from combining thiolated poly(vinyl alcohol) (tPVA), with polyethylene glycol polymers having varying thiol-reactive groups and structures. The tPVA and PEG-based thiol reactive polymers were separately dissolved in phosphate buffered saline (PBS) at a concentration of 6%. Equal volumes of the tPVA and PEG solutions were combined into a formulation and allowed to react at ambient temperatures (20-22° C.). Crosslink time of the polymers was measured by the time required for a 1.9 mm×8 mm magnetic stir bar spinning at 100 rpm immersed within the formulation to stop spinning. Degradation time of the hydrogel was determined by placing 1 mg hydrogel samples in 10 mL of PBS at either 60° C. or 37° C. Samples were observed and PBS was changed daily. Degradation time was defined as the day that the hydrogel sample was completely in solution, i.e., no solid mass was observed. Results are summarized in Table 1A.

TABLE 1A

Crosslink Time and Degradation Time for Hydrogels Formed from Formulations with Varying Thiol-reactive End-groups

| Thiol Reactive Polymer | Crosslink Time at 20-22° C. | Degradation Time (Days) 60° C. | 37° C. |
|---|---|---|---|
| PEG Diacrylate | ~4 minutes | ~3 | ~21 |
| 4-arm PEG acrylate | ~3 Minutes | 5-6 | ~40 |
| PEG Divinyl sulfone | ~5 Minutes | 8-9 | ~60 |
| 4-arm PEG vinyl sulfone | ~3-4 Minutes | 13 | ~80 |
| 4-arm PEG maleimide | Almost instantaneous, <2 seconds | >14 | >100 (Estimated) |

Example 1B—Effect of Thiol-Reactive Group on Hydrogel Degradation

Hydrogels were prepared by combining a formulation comprising thiolated poly (vinyl alcohol) (tPVA) with formulations comprising polyethylene glycol polymers having varying thiol-reactive groups and structures. The tPVA and PEG-based thiol reactive polymers were separately dissolved in phosphate buffered saline (PBS) at a concentration of 6% (tPVA) and 12% (thiol-reactive polymer). Equal volumes of the tPVA and PEG solutions were combined into a formulation and allowed to react at ambient temperature (20-22° C.). Degradation time was determined by placing 1 mg hydrogel samples in 10 mL of PBS at 60° C. Samples were observed and PBS was changed daily. Degradation time was defined as the day that the hydrogel sample was completely in solution, i.e., no solid mass was observed. Degradation time at 37° C. was calculated as follows: $t_r/t_a = 2^{((T_a-T_r)/10)}$ $t_r$: degradation time at real temperature
$t_a$: degradation time at accelerated test temperature
$T_r$: real temperature
$T_a$: accelerated test temperature Results are summarized in Table 1B.

TABLE 1B

Degradation Time for Hydrogels Formed from Formulations with Varying Thiol-reactive End-groups

| | Degradation Time (Days) | |
|---|---|---|
| Thiol Reactive Polymer | 60° C. | 37° C. (Calculated) |
| 4-arm PEG vinyl sulfone | 14 | 69 |
| 8-arm PEG vinyl sulfone | 19 | 94 |
| 4-arm PEG maleimide | 32 | 158 |

Hydrogels were prepared from a formulation comprising thiolated poly(vinyl alcohol) (tPVA) and polyethylene glycol acrylate polymers having varying molecular weights and structures (i.e., single and multi-arm). The tPVA and PEG-acrylate polymers were separately dissolved in phosphate buffered saline (PBS) at varying concentrations. Equal volumes of the tPVA and PEG-acrylate solutions were combined into a formulation and allowed to react at ambient temperatures (20-22° C.).

The amount of fluorescently labeled Dextran released from the hydrogels over 24 hours was determined. (Liao, et. al., "Influence of hydrogel mechanical properties and mesh size on vocal fold fibroblast extracellular matrix production and phenotype," Acta *Biomaterialia* 4:1161-1171 (2008)) Dextrans (Molecular weight 20 kDa, 40 kDa, 75 kDa and 150 kDa) labeled with fluorescein isothiocyanate (FITC-Dextran) were dissolved in water at 10 mg/mL. Hydrogel samples were placed in test tubes and a FITC-Dextran solution was added to the tubes. The FITC-Dextran was allowed to diffuse into the hydrogels for 24 hours at 37° C. The FITC-Dextran-containing hydrogels were removed and placed in test tubes with fresh PBS to allow the FITC-Dextran to diffuse out of the hydrogel. After 24 hours, the fluorescence of the PBS solution was measured and the amount of dextran released was calculated. Results are summarized in Table 2.

TABLE 2

Diffused FITC-Dextran for Hydrogels with Varying Composition

| | Diffused FITC-Dextran (µg/g hydrogel) | | | | | | |
|---|---|---|---|---|---|---|---|
| | 6% tPVA | | | | | 9% tPVA | |
| FITC-Dextran (MW) | 4.8% PEG Diacrylate (600 Da) | 6.0% PEG Diacrylate (1000 Da) | 6.0% PEG Diacrylate (2000 Da) | 6.0% PEG Diacrylate (3400 Da) | 12.0% 4-arm PEG Acrylate (10 kDa) | 9.0% PEG Diacrylate (3400 Da) | 9% 4-arm PEG Acrylate (10 kDa) |
| 20 kDa | 7.58 | 8.82 | 7.07 | 5.44 | 1.93 | 3.53 | 2.38 |
| 40 kDa | 5.44 | 5.49 | 4.52 | 4.38 | 1.14 | 1.83 | 1.31 |
| 70 kDa | 5.68 | 5.37 | 4.50 | 3.10 | 0.80 | 1.50 | 1.02 |
| 150 kDa | 4.59 | 4.82 | 3.73 | 2.75 | 0.75 | 1.37 | 0.95 |

Example 2—Effect of Varying Hydrogel Composition on Crosslink Density/Pore Size For extended-release of a large molecule such as a protein, the pore size of the extended-release hydrogel should be close to or smaller than the hydrodynamic radius of the molecule. The pore size of the hydrogel is determined by the distance between crosslinks or the crosslink density; the higher the crosslink density, the smaller the pore size. The pore size of a hydrogel can be evaluated by measuring the diffusion of dextran having varying hydrodynamic radii within the hydrogel.

In this example, the amount of diffused FITC-Dextran is lowest for the hydrogel formed using the 1:1 ratio of 6% tPVA:12% 4-arm PEG Acrylate formulation. Therefore, this formulation has the smallest hydrogel pore size of those shown in Table 2.

Example 3—FITC-Dextran Incorporation and Release from Hydrogels

Hydrogels were prepared from formulations comprising thiolated poly(vinyl alcohol) (tPVA) and polyethylene glycol polymers having varying thiol-reactive groups and structures. tPVA was dissolved in 1 mL phosphate buffered saline (PBS) at a concentration of 6%. FITC-Dextran (70 kDa) was dissolved in 1 mL PBS at a concentration of 22.5 mg/mL. The PEG-thiol reactive polymer was dissolved in the FITC-Dextran/PBS solution at a concentration of 12%. Equal 1 mL volumes of the tPVA and PEG/Dextran solutions were combined and allowed to react at ambient temperatures (20-22° C.). After suitable reaction time, a 1.2 g sample of each Dextran-loaded hydrogel (~13.5 mg FITC Dextran/sample) was placed in a dialysis tube. 2 mL of PBS was added to the inside of the tube and the tube placed in a container with 30 mL of PBS. Containers were placed in an incubator at 37° C. The PBS in the container was sampled periodically and its florescence measured to determine the amount of FITC-Dextran released from the hydrogel. The PBS in the container was replaced after sampling to ensure sink conditions were maintained throughout the study.

Three hydrogel formulations were evaluated: 6% tPVA: 6% PEG Diacrylate (6% PEGDA), 6% tPVA:12% 4-arm PEG Acrylate (12% PEGTA), and 6% tPVA:12% 4-arm PEG Vinyl sulfone (12% PEG-4VS). The results of the release studies are shown in FIG. 1. Complete release of the Dextran was observed at ~21 days for the 6% PEGDA hydrogel, ~44 days for the 12% PEGTA hydrogel, and ~80 Days for the 12% PEG-4VS hydrogel.

Example 4—Dextran Incorporation and Release from tPVA: Peg-Maleimide Hydrogel

Hydrogels were prepared from formulations containing thiolated poly(vinyl alcohol) (tPVA), with 4-arm polyethylene glycol maleimide. tPVA was dissolved in 1 mL phosphate buffered saline (PBS) at a concentration of 6%. FITC-Dextran (70 kDa) was dissolved in 1 mL PBS at a concentration of 22.5 mg/mL. The 4-arm PEG maleimide polymer was dissolved in the FITC-Dextran/PBS solution at a concentration of 12%. Equal 1 mL volumes of the tPVA and PEG/Dextran solutions were placed in separate barrels of a dual barrel syringe. A mixing tip was attached to the end of the dual barrel syringe and the two solutions were injected through the mixing tip simultaneously. The polymers crosslinked as they combined within the mixing tip (i.e., within seconds) forming a firm hydrogel exiting the mixing tip. A 1.2 g sample of each Dextran-loaded hydrogel was placed in a dialysis tube. 2 mL of PBS was added to the inside of the tube and the tube placed in a container with 30 mL of PBS. Containers were placed in an incubator at 37° C. The PBS in the container was sampled periodically and its fluorescence measured to determine the amount of FITC-Dextran released from the hydrogel. The PBS in the container was replaced after sampling to ensure sink conditions were maintained throughout the study.

Figure 2:
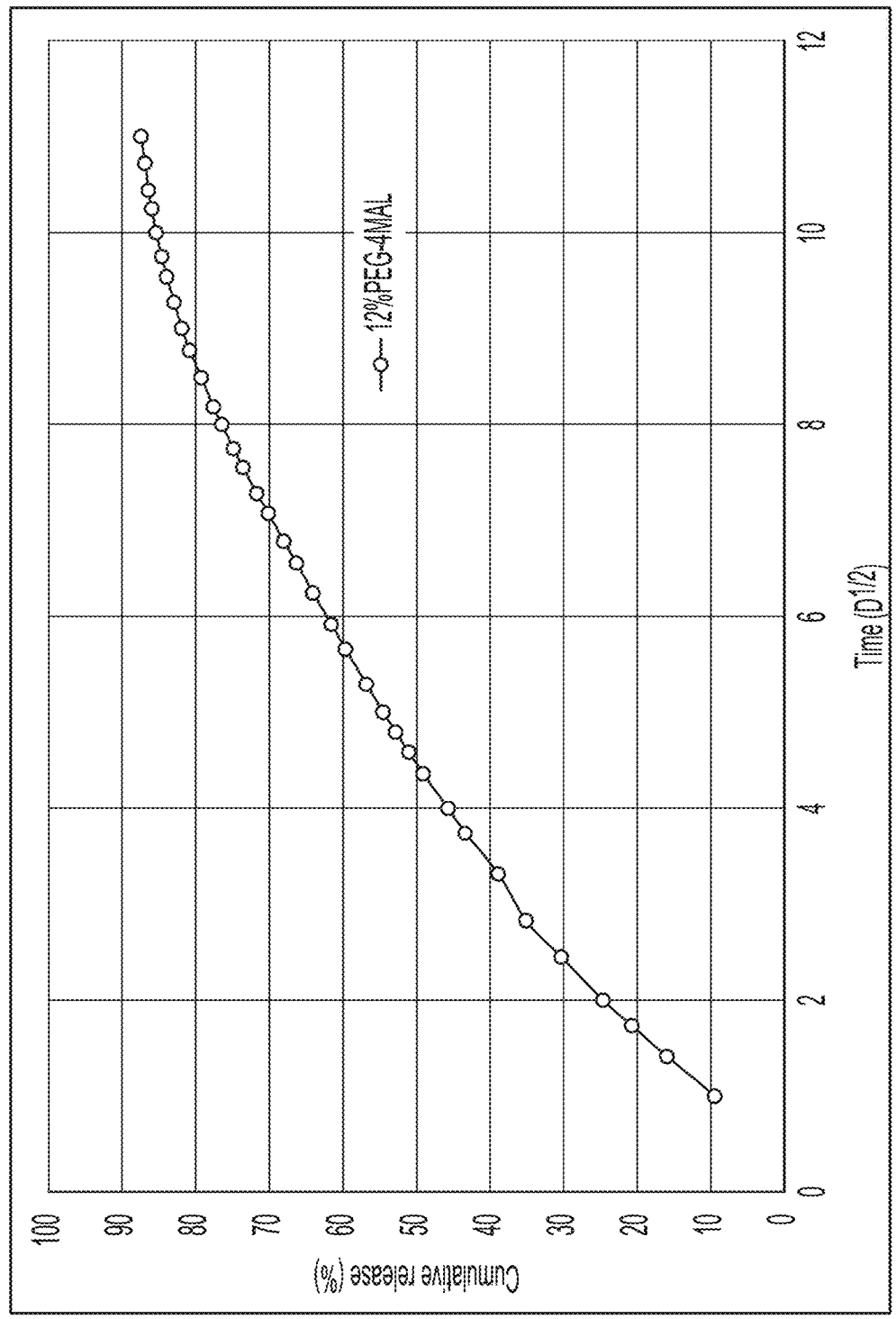
FIG. 2 shows the release of FITC-Dextran over time from an exemplary extended-release hydrogel described herein.

The results of the release study are shown in FIG. 2 as cumulative % release vs. days$^{1/2}$. The results show a nearly first-order release of the 70 kDa FITC-Dextran from the hydrogel over >60 days. The results were fit to the equation y=7.8276x+14.985 with an $R^2$=0.9982. Complete release was calculated from the linear equation to be ~120 days.

Example 5: Bevacizumab Incorporation into and Release from Extended-Release Hydrogels Bevacizumab is an anti-VEGF monoclonal antibody (large protein) with a molecular weight of ~150 kD that has been found to be a very effective treatment for several back-of-the-eye diseases including age-related macular degeneration (AMD), proliferative diabetic retinopathy, diabetic macular edema, macular edema from retinal vein occlusions and choroidal neovascularization, among others. Intravitreal injection of bevacizumab at a dose of 1.25 mg has been well tolerated and shown to provide improvement in visual acuity, decreased retinal thickness and reduction in vascular leakage in many patients. To maintain the improvement in vision, monthly repetitive injections are required to maintain the effective dose of ~1 µg/mL in the vitreous. However, when repeated injections are required, there is a high risk of complications such as endophthalmitis, as well as the pain, apprehension and distress associated with inserting needles into eyes. Therefore a delivery method that reduces the need for repetitive injections and extends the therapeutic dose in the vitreous would provide a significant improvement.

Bevacizumab was loaded into tPVA:4-arm PEG vinyl sulfone (PEG-4VS-1, PEG-4VS-2) and tPVA:4-arm PEG maleimide (PEG-4MAL) hydrogels as described in Examples 3 and 4, respectively. Release studies were performed as described previously. 0.5 g samples with ~6 mg bevacizumab were loaded into the dialysis tubes. 1 mL of PBS was added to the tubes and the tubes were placed in a container with 30 mL of PBS at 370° C. The amount of bevacizumab released at each time point was determined by measuring the auto-florescence of the protein in the release solutions at 280 nm.

Figure 3A:
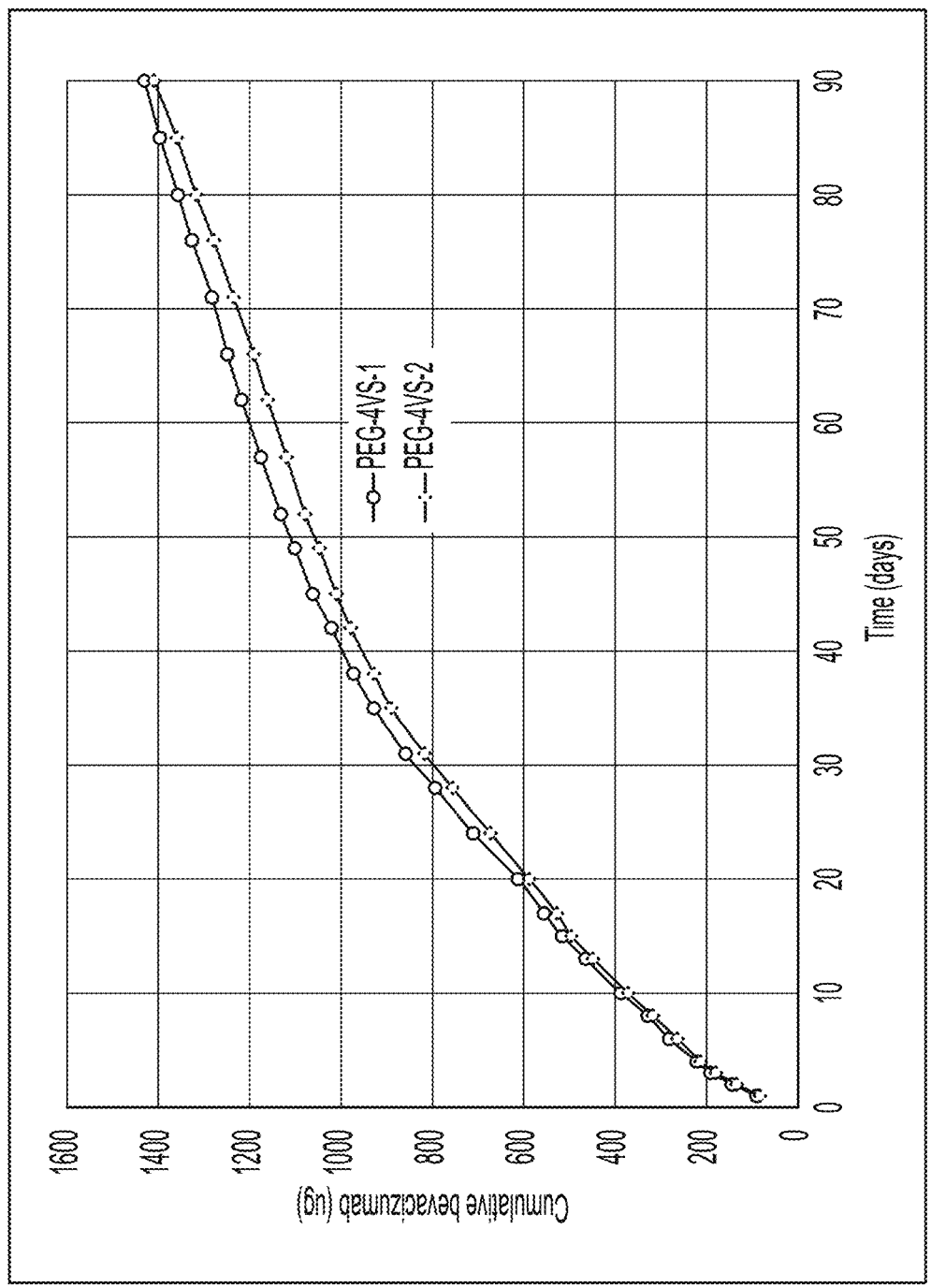
FIGS. 3A and 3B shows the release of a large protein, Bevacizumab, from exemplary extended-release hydrogels described herein.
Figure 3B:
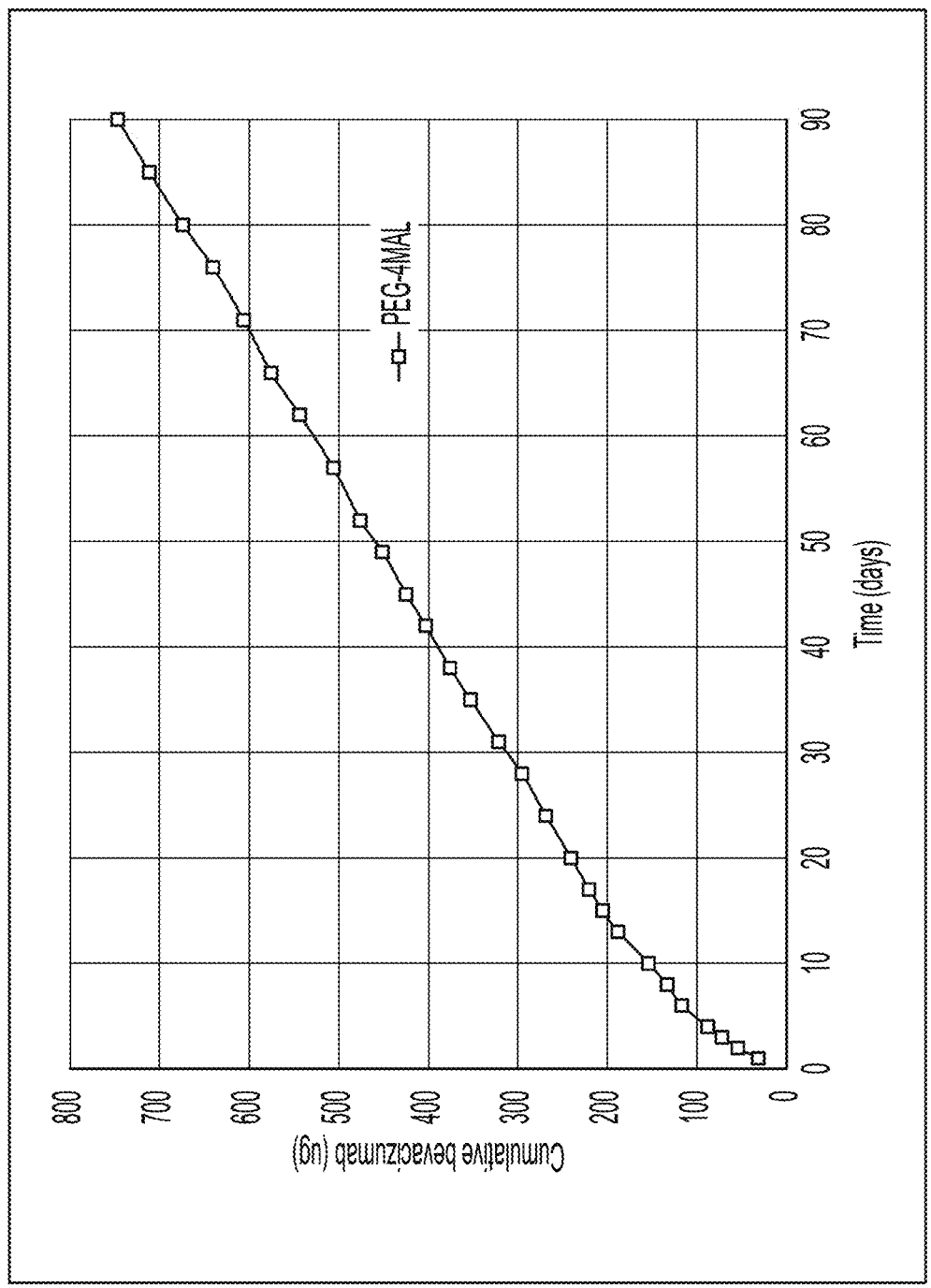

Results of the release studies are shown in FIGS. 3A and 3B. The concentration of bevacizumab observed in the release media was found to be ~2 µg/mL for the tPVA:4-arm PEG vinyl sulfone hydrogel and ~1 µg/mL for the tPVA:4-arm PEG maleimide hydrogel.

To confirm that the bevacizumab released from the extended-release hydrogel was still active and able to bind to VEGF, samples from the release solutions for the tPVA: 4-arm PEG vinyl sulfone hydrogels were evaluated by an ELISA assay. (Sinapis et. al, "Pharmacokinetics of intravitreal bevacizumab (Avastin®) in rabbits" *Clin Ophthalmol.* 5:697-704 (2011)). Table 3 shows the results of the ELISA assay compared to the auto-fluorescence results at various time points. Results of both assays were similar at all time points indicating that the bevacizumab was still an active protein after incorporation and release from the extended-release hydrogel.

TABLE 3

Bevacizumab Concentration After Release From tPVA:4 Arm PEG Vinyl sulfone Extended-Release Hydrogel

| Day | Bevacizumab by Fluorescence (ug/mL) | Bevacizumab by ELISA (ug/mL) |
|---|---|---|
| 1 | 3.04 | 2.70 |
| 2 | 1.80 | 2.55 |
| 3 | 1.56 | 1.48 |
| 4 | 1.02 | 0.82 |
| 6 | 2.00 | 1.71 |
| 8 | 1.58 | 1.55 |
| 10 | 1.98 | 1.76 |
| 13 | 2.59 | 2.39 |
| 15 | 1.72 | 2.41 |
| 17 | 1.32 | 1.35 |
| 20 | 1.90 | 2.15 |
| 24 | 3.30 | 3.92 |
| 28 | 2.84 | 3.26 |
| 31 | 2.17 | 2.04 |
| 35 | 2.33 | 2.19 |
| 38 | 1.48 | 1.07 |
| 42 | 1.62 | 1.39 |
| 45 | 1.36 | 1.64 |

Example 6—Tacrolimus Encapsulation into and Release from a Hydrogel

Tacrolimus is a small molecule drug (~800 Da) with low solubility in water (~1 μg/mL). It is an anti-inflammatory drug that may be useful in treating various conditions, including uveitis or other inflammatory conditions of the eye.

Tacrolimus was encapsulated in Soluplus®, a graft copolymer of polycaprolactam-polyvinyl aetate-polyethylene glycol. Soluplus® is an amphiphilic polymer that self-assembles into nanomicelles in water. Tacrolimus was encapsulated within the hydrophobic core of the nanomicelles as described in Wu, et al., "Novel self-assembled tacrolimus nanoparticles cross-linking thermosensitive hydrogels for local rheumatoid arthritis therapy" *Colloids and Surfaces B: Biointerfaces* 149 97-104 (2017). Nanoparticles with a size of 70±20 nm incorporating ~12% tacrolimus by weight were obtained.

Figure 4:
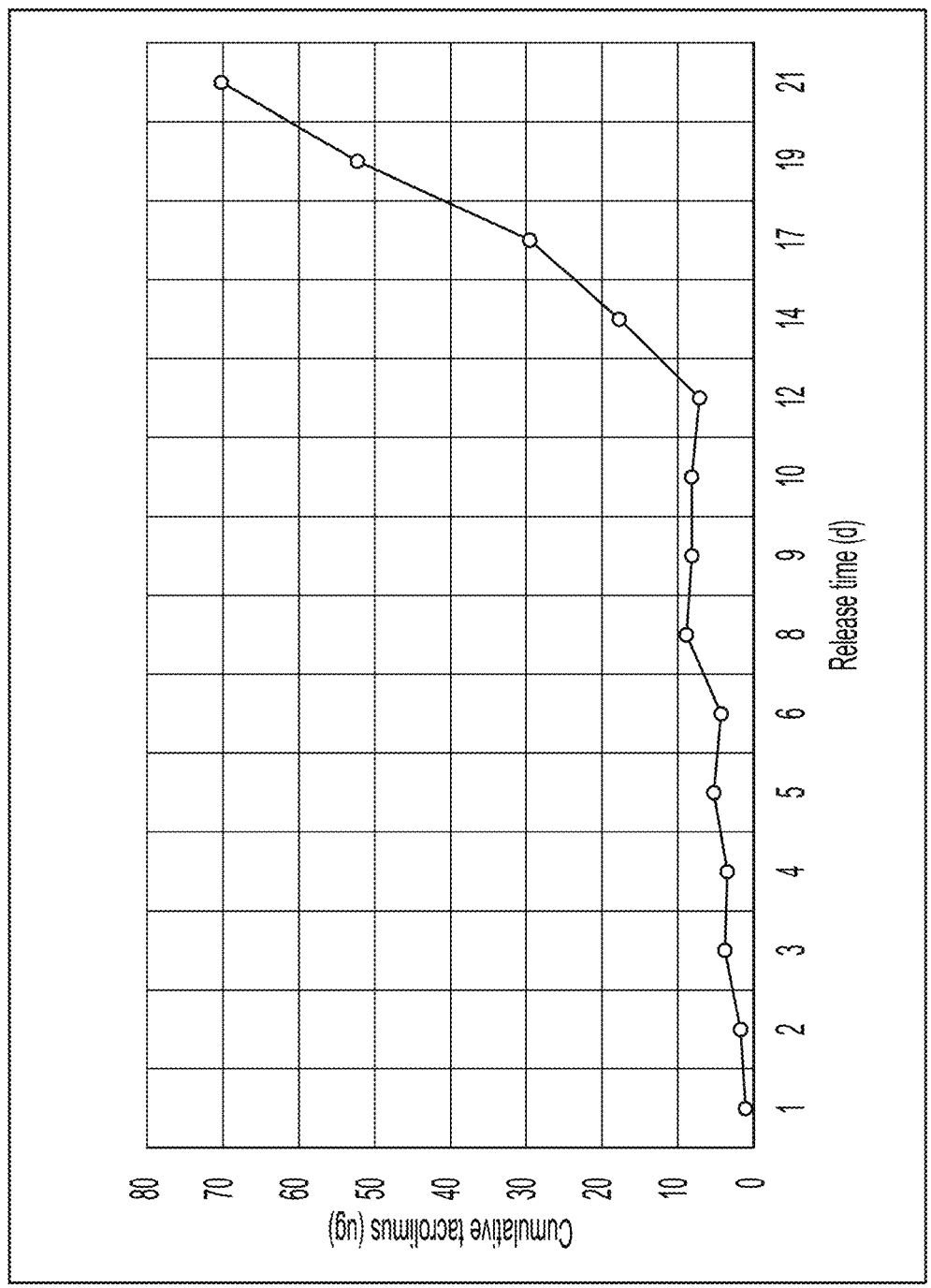
FIG. 4 shows the release of an encapsulated small molecule, tacrolimus, from an exemplary extended-release hydrogel described herein.

Hydrogels were prepared from thiolated poly(vinyl alcohol) (tPVA) and polyethylene glycol diacrylate (PEGDA). tPVA was dissolved in 1 mL phosphate buffered saline (PBS) at a concentration of 6%. 0.25 mL of tacrolimus loaded nanoparticles in deionized water at a concentration of ~8 mg/mL was added to 0.75 mL of PBS. The PEGDA was then dissolved in the 1 mL tacrolimus nanoparticle solution at a concentration of 6%. Equal 1 mL volumes of the tPVA and PEG/tacrolimus solutions were combined and allowed to react at ambient temperatures (20-22° C.). The resulting hydrogels were visibly transparent. After suitable reaction time, a 1.25 g sample of each tacrolimus-loaded hydrogel (~135 μg tacrolimus/sample) was placed in a dialysis tube. 3 mL of PBS with 0.5% sorbate was added to the inside of the tube and the tube placed in a container with 27 mL of PB with 0.5% sorbate as the release solution. Containers were placed in an incubator at 37° C. The release solution in the container was sampled periodically to determine the amount of tacrolimus released from the hydrogel. The concentration of tacrolimus in the sample was measured using a commercially available ELISA assay. The release solution in the container was replaced after sampling to ensure sink conditions were maintained throughout the study. Results of the release study are shown in FIG. 4. The hydrogel was completely degraded by day 21. Encapsulation of active pharmaceutical ingredients into nanoparticles, prior to embedding the nanoparticle within a hydrogel, may extend the in vivo kinetics of the active pharmaceutical ingredient. Such embedment may also reduce the possibility of nanoparticles obstructing the visual axis, a common problem observed with other particle mediated drug delivery systems.

Example 7—Application of a Thin Film During the Viscous Phase of Crosslinking Thin films from formulations comprised of thiolated polyvinyl alcohol (tPVA) and polyethylene glycol diacrylate (PEGDA) were deposited in a test substrate and evaluated for performance. Test surfaces were prepared by placing 5 mm holes on a first surface which was then placed on a second surface without holes. The test surfaces were then mounted with the test surface vertical (at 90 degrees) to a table.

Ten (10) mL of 1×phosphate buffered saline (PBS) was added to 0.24 g of lyophilized tPVA to obtain a 2.4% tPVA solution and 5.6 mL of 1×PBS was added to 0.24 g of lyophilized PEGDA to obtain a 4.3% PEGDA solution. 2 mL each of tPVA and PEGDA solution were individually drawn and then mixed. 1 mL of the mixed hydrogel solution was then filtered through a 1 μm syringe filter into a 1 mL syringe. A 25 G stainless steel cannula with a 1 mm long silicone soft brush tip (FIG. 9) was then attached to the 1 mL syringe.

Beginning twelve (12) minutes after mixing and every 30 seconds thereafter through 19 minutes 30 seconds, using the brush tip cannula, hydrogel solution was applied to the test surface to cover the hole and extending at least 1 mm from the edge of the hole.

The consistency of the solution was observed and recorded as runny, viscous or too viscous. The hydrogel solution was labeled as "runny" if the material, when applied to the vertical test surface, would sag and begin to run off. The solution was labeled as "viscous" if the material could be applied as a smooth layer that remained in place on the vertical surface. The solution was labeled as "too viscous" if the hydrogel was difficult to inject and/or could not be applied as a smooth layer. The start time and end time under which the hydrogel solution was viscous (neither runny not too viscous) was recorded and defined as the application window. The test was performed at room temperature (~22° C.) and repeated three times.

The start time ranged from 12 to 13 minutes and the end time from 17 to 18 minutes after mixing. The application window was 5 minutes for each run as summarized below in Table 4.

TABLE 4

Application window of thin film during viscous phase of crosslinking

| Run | Start Viscous (mins) | End Viscous (mins) | Window (mins) |
|---|---|---|---|
| 1 | 12 | 17 | 5 |
| 2 | 13 | 18 | 5 |
| 3 | 13 | 18 | 5 |
| Mean | 13 | 18 | 5 |

The application of the material during the viscous phase may have certain unique advantages, as less material is used. An alternative approach to achieving a viscous gel to allow for application of a thick solution that does not run would be to use a higher concentration of nucleophile and electrophile polymers, or to use a high amount of long, inactive polymer chains, as a thickening agent, to create a viscous material. However, the advantage of applying a retinal tamponade sealant to the site of a retinal break during its dynamic viscous phase is that when used intraocularly, the low percentage of solids may reduce the risk of an intraocular pressure elevation when the material degrades. In other applications, it may reduce the risk of foreign body reaction. The application of the material strictly during its "dynamically viscous phase" has unique and unexpected advantages, as opposed to simply thickening it, and may be extended to other polymer systems which could be used for intraocular retinal tamponade or drug delivery.

Example 8—Viscosity of the Hydrogel Solution During the Application Window

Samples of hydrogel solution were prepared for viscosity testing using rotational rheometry. Ten (10) mL of 1×phosphate buffered saline (PBS) was added to 0.24 g of lyophilized tPVA to obtain a 2.4% tPVA solution and 5.6 mL of 1×PBS was added to 0.24 g of lyophilized PEGDA to obtain a 4.3% PEGDA solution. 2 mL each of tPVA and PEGDA solution were individually drawn and then mixed. 1 mL of the mixed hydrogel solution was then injected between the top and bottom plates of a TA Instruments DHR1 rheometer (60 mm 2° stainless steel cone, 0.057 mm truncation gap, 0.006 mm trim gap). Complex viscosity and storage module were continuously recorded for 30 minutes (1800 seconds) at an angular frequency of 6.283 rad/sec and a strain of 0.1%. The test was performed at 22° C.

The plot of complex viscosity vs time is shown in FIG. 8. From 12 to 13 minutes (start of the "viscous phase" from Example 7), the complex viscosity of the hydrogel solution was between 550 cP and 1350 cP. The viscosity increased to between 8900 cP and 11,600 cP after 17-18 minutes (end of the "viscous phase" form Example 7) respectively.

Other, alternative methods of creating a viscous solution, from a "runny substrate", may include the addition of certain excipients, especially high molecular weight solids, or using larger molecular weight polymer components to increase the viscosity of the solution. In this clinical context, increasing the total number of solids or the molecular weight of the functional polymers would be undesirable, as they would increase the risk of an intra-ocular pressure (IOP) elevation, as the higher percentage of solids in the solution may cause an obstruction of the trabecular meshwork and lead to devastating elevations of eye pressure. The application of a runny polymer solution during the dynamically changing "viscous phase" as in Example 7, could be extended to other systems which may be non-viscous initially but become viscous over time.

Example 9—Time to Reach Viscous Phase can be Reduced by Heating the Hydrogel Solution after Mixing Test surfaces were prepared as in Example 7. Ten (10) mL of 1×phosphate buffered saline (PBS) was added to 0.24 g of lyophilized tPVA to obtain a 2.4% tPVA solution and 5.6 mL of 1×PBS was added to 0.24 g of lyophilized PEGDA to obtain a 4.3% PEGDA solution. 2 mL each of tPVA and PEGDA solution were individually drawn and then mixed. 1 mL of the mixed hydrogel solution was then filtered through a 1 µm syringe filter into a 1 mL syringe. The 1 mL syringe was then placed in a dry bath set at different temperatures ranging from about 22° C. to about 50° C. At specified times the 1 mL syringe was removed and the temperature of the solution was measured. A brush tip cannula was then attached to the syringe and the hydrogel solution deposited on the test surface. The consistency of the solution was observed and recorded as runny, viscous, or too viscous as in Example 7. For each temperature condition the start and end time for the viscous phase was recorded from the time of mixing. The time to reach the viscous phase (gelation time) is an important feature of the hydrogel system as it represents the time that the clinician will have to wait after mixing the two solutions before it is ready to be applied to the tissue.

Figure 10:
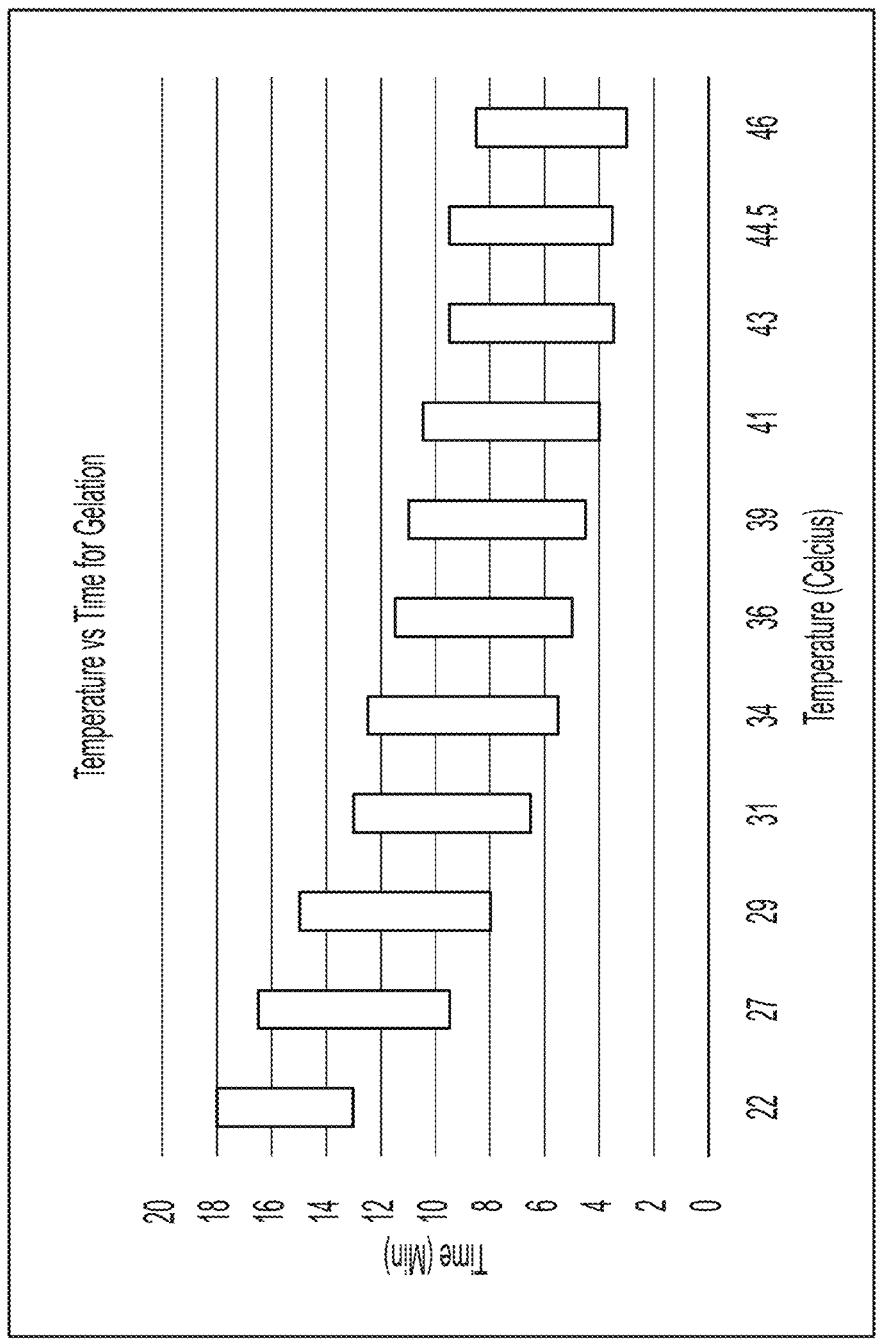
FIG. 10 shows the time for hydrogel gelation as a function of temperature for exemplary hydrogel solutions described herein.

Results are presented in FIG. 10. The time for the hydrogel solution to reach the viscous phase (time for gelation) was reduced from 13 minutes at 22° C. to 3 minutes at 46° C. The application window remained ~5-6 minutes for each condition tested.

Example 10—Hydrogel Solution Warming Device

Figure 11:
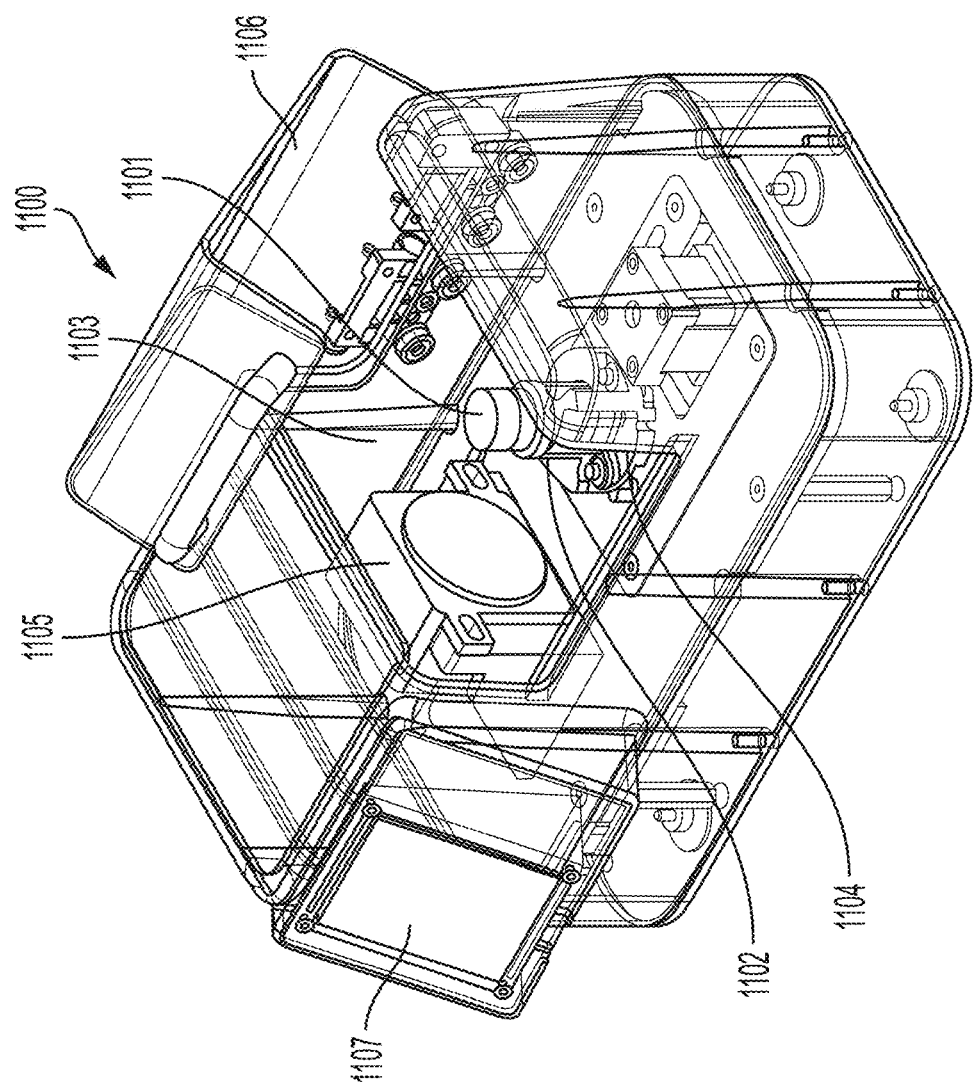
FIG. 11 shows a schematic of a device that can be used to heat and mix various solutions, including the hydrogel solutions or formulations disclosed herein.

A device was designed to improve the consistency of the mixing and heating of the hydrogel solution (FIG. 11). The warming device 1100 heats the solution to a specified temperature over a specified time while constantly shaking the solution to provide mixing and even distribution of solution temperature.

The nucleo-functional polymer (e.g., tPVA) and electro-functional polymer (e.g., PEGDA) solutions are combined in a vial 1101 (e.g., glass vial) to form a hydrogel solution. The vial 1101 is inserted into a holder 1102 within the heating chamber 1103 of the warming device 1100. The holder 1102 is attached to a platform 1104 that is capable of rotating (e.g., with an orbital motion) to provide a constant "swirling" motion for the hydrogel solution within the vial 1101. A heater 1105 with a fan directs warm air at the vial 1101 while it is rotating. Thermocouples measure the temperature of the heater 1105 output and monitor the temperature of the hydrogel solution. After placing the vial 1101 in the holder 1102 and closing the door 1106, the operator will initiate a warming cycle using controls provided on a display 1107 at which time the vial 1101 begins to rotate, and the heater 1105 starts. Once the specified solution temperature (for example 37° C.) and time (for example 3 minutes) is reached the heater 1105 shuts off and the vial 1101 stops rotating. The door 1106 is then opened, the vial 1101 removed, and the warmed hydrogel solution withdrawn from the vial for application. The display 1107 also provides information on the status of the warming cycle to the user and informs them when the cycle is completed, and the vial is ready to be removed.

Example 11—tPVA Solution pH Affects Gelation Time

The pH of lyophilized tPVA reconstituted with 1×PBS has been observed to be variable and reduced from 7.5 to 6.9 when stored for longer than about 12-15 months. The impact of a lower pH on gelation time was evaluated. Hydrogel solutions were prepared for gelation time testing as follows. Ten (10) mL 1×phosphate buffered saline (1×PBS) was added to 0.24 g of lyophilized tPVA to obtain a 2.4% tPVA solution and 5.6 mL of 1×PBS was added to 0.24 g of lyophilized PEGDA to obtain a 4.3% PEGDA solution. The pH of the tPVA solution was measured. 2 mL each of tPVA and PEGDA solution were individually drawn and then mixed. 1 mL of the mixed hydrogel solution was then filtered through a 1 µm syringe filter into a 1 mL syringe. A 25 G stainless steel cannula with a 1 mm long silicone soft brush tip (FIG. 9) was then attached to the 1 mL syringe.

For each preparation the gelation time was assessed by expressing a small volume of the hydrogel solution onto a vertical test surface. Gelation time was defined as the time form mixing when the solution becomes viscous as described in Example 7.

Figure 12:
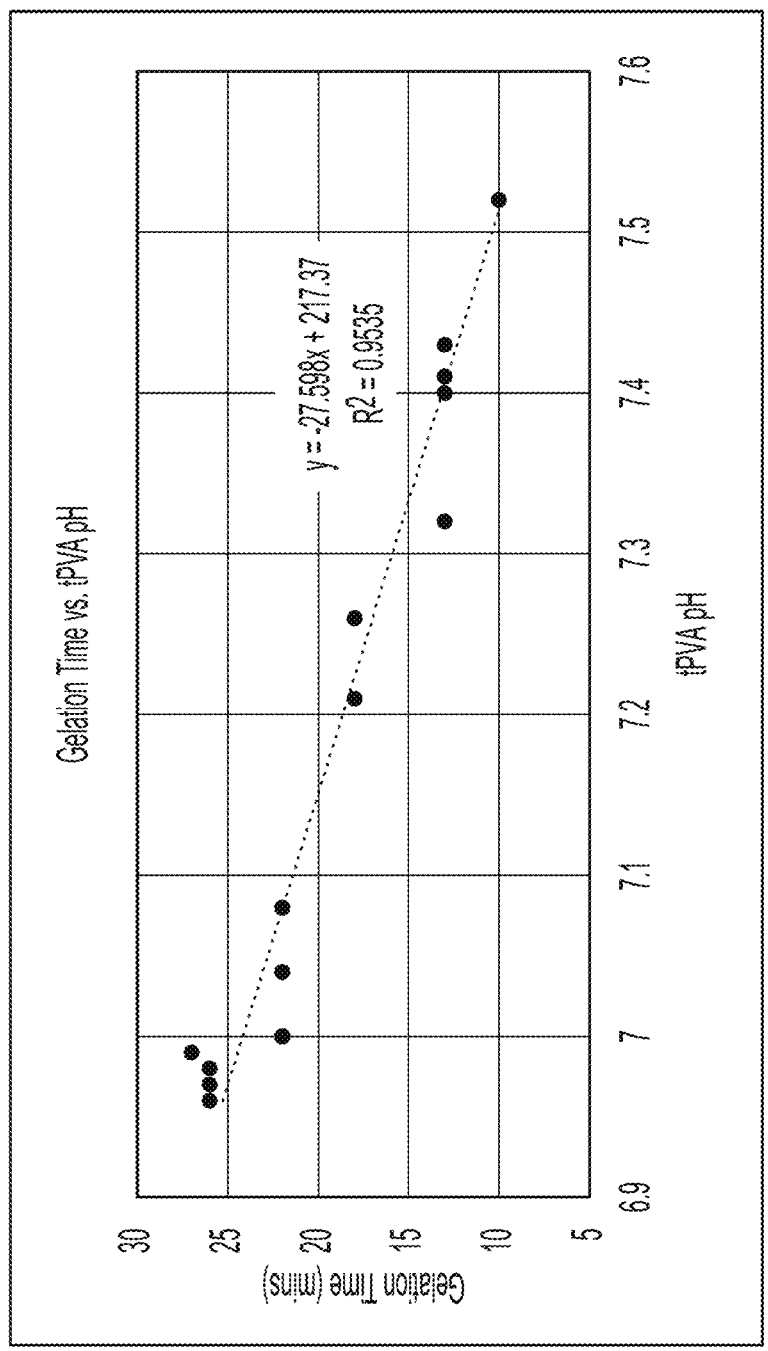
FIG. 12 shows the time to gelation for hydrogel formulations made from tPVA solutions at various pHs.

The pH of reconstituted tPVA ranged from 6.96 to 7.52. The relationship between pH and gelation time was generally linear with a correlation coefficient of 0.95. When the pH of the tPVA was low, gelation time was longest. When pH of the reconstituted tPVA was near 7.4, the gelation time was around 12-13 minutes at room temperature (22°). Results are summarized in FIG. 12.

Example 12—tPVA Solution pH Affects Size of Degradation Materials

Hydrogel samples were prepared and placed in 1×PBS at 37° C. for evaluation of degradation. Samples of the degraded hydrogel/PBS solution were pulled periodically and assessed for particle size of the degraded hydrogel using Dynamic Light Scattering (DLS). Particle size of the degrading hydrogel is important because large particles (greater than about 200 nm, the smallest size of the pores within the trabecular meshwork of the eye) could become lodged in the trabecular meshwork of the drainage system in the eye leading to an undesirable increase in ocular pressure.

Ten (10) mL 1×phosphate buffered saline (1×PBS) was added to 0.24 g of lyophilized tPVA to obtain a 2.4% tPVA solution and 5.6 mL of 1×PBS was added to 0.24 g of lyophilized PEGDA to obtain a 4.3% PEGDA solution. The pH of the tPVA solution was measured. 2 mL each of tPVA and PEGDA solution were individually drawn and then mixed. A 2 mL volume of hydrogel solution was deposited in a petri dish and allowed to crosslink. 20 mL of 1×PBS was added to the petri dish and the dish placed in an incubator shaker set at 37° C. Samples of the degraded hydrogel/PBS solution were taken at 1 week, 2 weeks, 3 weeks, and 4 weeks (fully degraded) and particle size distribution was evaluated using DLS (Horiba SZ-100) for each sample.

As shown in Table 5, the particle size observed for hydrogels formed from tPVA with a lower pH (6.9) were larger at all time points and much larger at the interim degradation time points of 1 and 2 weeks. Similar results were observed for hydrogel samples placed in 60° C. 1×PBS to accelerate the degradation when assessed at 1.5 and 2 days. The particle sizes of hydrogels formed from the lower pH tPVA material are significantly higher than expected when compared to the initial, "fresh" tPVA material is used. The mean particle size, approaching the one micron (1 μm) range, would be of a sufficient size to obstruct the trabecular meshwork in the eye. The trending of lower pH over time, and therefore trabecular meshwork obstructions, was unexpected based on the design of the system and its storage conditions. Therefore a mitigation strategy to ensure that particle size remains low is required.

TABLE 5

Particle size of degraded hydrogels with normal (7.4) and low (6.9) pH at 37° C.

| | pH | |
|---|---|---|
| | 7.4 | 6.9 |
| | Mean Particle Size (nm) | |
| Week 1 | 126 | 406 |
| Week 2 | 225 | 920 |
| Week 3 | 157 | 227 |
| Week 4 | 31 | 111 |

Example 13—Using a Customized Formulation of PBS (mPBS, 5×) Diluent to Reconstitute tPVA Normalizes the pH and Restores Gelation Time and Degradation Particle Size Using 1×PBS to reconstitute the tPVA that is then used to form the hydrogel has been observed in the clinical setting to lead to concerning increases in intra-ocular pressure when the tPVA has been stored for more than about 12 months. Unexpectedly, the named inventors found that use of a customized PBS formulation to reconstitute tPVA that is then used to form the hydrogel results in normalized pH of the tPVA solution and maintenance of desired gelation time and hydrogel degradation particle size.

A modified PBS solution with 5×phosphate was prepared by first reconstituting a 10×powdered PBS (Fisher Scientific CN:BP665-1) with deionized water (DI) according to the manufacturer's instructions and then further diluting 2:1 with additional DI water. Vials of lyophilized tPVA from a batch exhibiting low pH were reconstituted with either 1×PBS or 5×PBS to obtain a 2.4% solution and the pH was measured. Similarly, 4.3% PEGDA solutions were prepared with either 1×PBS or 5×PBS. 2 mL each of tPVA and PEGDA solution were individually drawn and then mixed. 1 mL of the mixed hydrogel solution was then filtered through a 1 μm syringe filter into a 1 mL syringe. A brush tip cannula was then attached to the syringe and the hydrogel solution deposited on the test surface. The gelation time (time to become viscous) was then measured as described in Example 7, and is provided below in Table 6.

tPVA solutions reconstituted with 1×PBS had a pH between 6.87 and 6.99 and a gelation time of 22-26 minutes whereas the pH increased to 7.30 to 7.46 and the gelation time was reduced to 12-15 minutes when reconstituted with 5×PBS. Further modifications were made to reduce the total number of solutes (e.g., reducing the sodium chloride (to 50-90 mM) and/or potassium chloride (to 2.5-3 mM) concentrations without changing the sodium phosphate(50 mM) or potassium phosphate (9 nM) concentrations) to keep the osmolality within the desire range required for intraocular use (e.g., 280 mOsm/kg to about 320 mOsm), with no impact on ability to appropriately buffer the solution or effect cross-linking time, thus resulting in a unique custom formulation to permit longer shelf life while maintaining degradation in the desire range for ophthalmic use.

TABLE 6

Gelation time of hydrogel solutions reconstituted with 1X PBS vs 5X PBS

| | 1X PBS | | 5X PBS | |
|---|---|---|---|---|
| Sample | pH | Gelation Time (Mins) | pH | Gelation Time (Mins) |
| 1 | 6.90 | 26 | 7.35 | 14 |
| 2 | 6.92 | 24 | 7.30 | 15 |
| 3 | 6.97 | 22 | 7.30 | 15 |
| 4 | 7.38 | | 7.35 | 15 |
| 5 | 6.87 | | 7.46 | 12 |
| 6 | 6.90 | | 7.36 | |
| 7 | 6.99 | | 7.30 | |
| 8 | 6.91 | | 7.31 | |
| 9 | | | 7.37 | |
| 10 | | | 7.38 | |
| Average | 6.98 | 24 | 7.35 | 14 |
| Std. Dev. | 0.17 | 2 | 0.05 | 1 |

Similarly, a hydrogel sample was prepared for degradation particle size as in Example 11. A vial of lyophilized tPVA from a batch exhibiting low pH when reconstituted with 1×PBS was prepared with 5×PBS at a concentration of 2.4% tPVA. The pH was measured and the solution was combined 1:1 with a 4.3% PEGDA solution also prepared with 5×PBS. The hydrogel was placed in 1×PBS at 37° C., and samples were taken at 1, 2, 3 and 4 weeks for DLS particle size measurement. As shown below in Table 7, the particle size at all time points was reduced and consistent with what was observed for samples prepared with tPVA reconstituted with 1×PBS at pH 7.4.

TABLE 7

Particle size of degraded hydrogels made from tPVA
and PEGDA solutions reconstituted in 5X PBS

| | pH 7.52<br>Mean Particle Size (nm) |
|---|---|
| Week 1 | 200 |
| Week 2 | 213 |
| Week 3 | 201 |
| Week 4 | — |

Without being bound by any particular theory, it is believed that the phosphate in the 5×PBS may act as a unique stabilizer that helps maintain the desired pH range in the nucleo-functional polymer and electro-functional polymer solutions, even when those solutions are made from reconstituted polymer that has been stored for extended periods of time.

INCORPORATION BY REFERENCE

All of the references cited herein are hereby incorporated by reference in their entireties.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. An injectable, ocular formulation for forming a hydrogel in an eye of a subject, the formulation comprising:
   a. a nucleo-functional polymer that is a biocompatible polymer comprising poly(vinyl alcohol) containing a plurality of thio-functional groups —$R^1$—SH, wherein —$R^1$—SH is —OC(O)—($C_1$-$C_6$ alkylene)—SH;
   b. an electro-functional polymer that is a biocompatible polymer comprising poly(ethylene glycol) containing at least one thiol-reactive group; and
   c. a liquid pharmaceutically acceptable carrier comprising 5×phosphate buffered saline (PBS) that is suitable for administration of the ocular formulation to the eye of the subject;
   wherein the ocular formulation has a pH in the range of about 7.1 to about 7.7, an osmolality in the range of about 280 mOsm/kg to about 320 mOsm/kg and the formulation forms a hydrogel in the eye of the subject.

2. The formulation of claim 1, wherein a first solution comprising the nucleo-functional polymer and a second solution comprising the electro-functional polymer are mixed to form the formulation.

3. The formulation of claim 1, wherein the 5×PBS comprises about 50 mM to about 90 mM sodium chloride, about 2.5 mM to about 3 mM potassium, about 50 mM sodium phosphate, about 9 nM potassium phosphate, or combinations thereof.

4. The formulation of claim 1, wherein the formulation has an osmolality in the range of about 280 mOsm/kg to about 300 mOsm/kg.

5. The formulation of claim 1, wherein the formulation has an osmolality in the range of about 300 mOsm/kg to about 320 mOsm/kg.

6. The formulation of claim 2, wherein the formulation has a viscosity of between about 550 cP and about 1350 cP at around 12-13 minutes after mixing the first and second solutions to form the formulation, or after about 30 seconds to about 120 seconds after mixing when heat is applied to the formulation.

7. The formulation of claim 2, wherein the formulation has a viscosity of between about 8900 cP and about 11,600 cP at around 17-18 minutes after mixing the first and second solutions to form the formulation, or after about 30 seconds to about 120 seconds after mixing when heat is applied to the formulation.

8. The formulation of claim 2, wherein the formulation has an initial, low viscosity after mixing the first and second solutions to form the formulation such that the formulation can be administered through a needle having a gauge of less than or equal to 23 using a force of no more than 5 N.

9. The formulation of claim 1, wherein the formulation is formed following separate injection of the nucleo-functional polymer and the electro-functional polymer into the vitreous cavity of the eye of the subject.

10. The formulation of claim 1, wherein the nucleo-functional polymer, the electro-functional polymer, or both, are reconstituted in 5×PBS.

11. The formulation of claim 10, wherein the reconstituted nucleo-functional polymer, the reconstituted electro-functional polymer, or both, has a pH between about 7.1 to about 7.7.

12. The formulation of claim 10, wherein the nucleo-functional polymer, the electro-functional polymer, or both, are reconstituted after having been stored for at least 1 week, at least 1 month, at least 2 months, at least 6 months, at least 12 months, at least 15 months, at least 18 months, at least 20 months, or at least 24 months.

13. The formulation of claim 1, wherein the poly(ethylene glycol) is linear, branched, a dendrimer, or multi-armed.

14. The formulation of claim 1, wherein the hydrogel formed in the eye of the subject undergoes complete biodegradation from the eye of the subject within about 3 days to about 7 days, about 2 weeks to about 8 weeks, about 4 months to about 6 months, or within 12 months or 24 months.

15. The formulation of claim 1, wherein the hydrogel formed in the eye of the subject results in a pressure within the eye of less than about 30 mmHg.

* * * * *